(12) United States Patent
Mizumura et al.

(10) Patent No.: US 9,481,829 B2
(45) Date of Patent: Nov. 1, 2016

(54) COMPOUND, HAZE-LOWERING AGENT, LIQUID CRYSTAL COMPOSITION, POLYMER MATERIAL, AND FILM

(71) Applicant: FUJIFILM Corporation, Tokyo (JP)

(72) Inventors: Masatoshi Mizumura, Ashigarakami-gun (JP); Shunya Katoh, Ashigarakami-gun (JP); Minoru Uemura, Ashigarakami-gun (JP); Yasuhiro Ishiwata, Ashigarakami-gun (JP); Masaru Yoshikawa, Ashigarakami-gun (JP); Hiroshi Matsuyama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 149 days.

(21) Appl. No.: 14/163,901

(22) Filed: Jan. 24, 2014

(65) Prior Publication Data
US 2014/0138580 A1   May 22, 2014

Related U.S. Application Data

(63) Continuation of application No. PCT/JP2012/066957, filed on Jul. 3, 2012.

(30) Foreign Application Priority Data

Jul. 27, 2011  (JP) .................................. 2011-164777
Feb. 22, 2012  (JP) .................................. 2012-036512

(51) Int. Cl.
| | | |
|---|---|---|
| *C07C 69/62* | (2006.01) | |
| *C09K 19/20* | (2006.01) | |
| *C09K 19/54* | (2006.01) | |
| *C07C 69/92* | (2006.01) | |
| *C09K 19/32* | (2006.01) | |
| *C09K 19/34* | (2006.01) | |
| *C09K 19/58* | (2006.01) | |
| *C09K 19/04* | (2006.01) | |

(52) U.S. Cl.
CPC ............... *C09K 19/54* (2013.01); *C07C 69/92* (2013.01); *C09K 19/2007* (2013.01); *C09K 19/322* (2013.01); *C09K 19/3475* (2013.01); *C09K 19/588* (2013.01); *C09K 2019/044* (2013.01); *C09K 2019/0429* (2013.01); *C09K 2019/2078* (2013.01)

(58) Field of Classification Search
CPC ... C07C 69/62; C07C 22/08; C09K 19/2007; C09K 19/322; C09K 19/3422; C09K 19/54; C09K 19/38; C09K 2019/2078; C09K 2219/03; C09K 19/588; C09K 2019/044
See application file for complete search history.

(56) References Cited

U.S. PATENT DOCUMENTS

| | | |
|---|---|---|
| 2,367,661 A | 1/1945 | Agre |
| 2,367,670 A | 1/1945 | Christ |
| 2,448,828 A | 9/1948 | Renfrew et al. |
| 2,722,512 A | 11/1955 | Crandall |
| 2,951,758 A | 9/1960 | Notley |
| 3,046,127 A | 7/1962 | Barney et al. |
| 3,549,367 A | 12/1970 | Chang et al. |
| 4,212,970 A | 7/1980 | Iwasaki |
| 4,239,850 A | 12/1980 | Kita et al. |
| 4,292,152 A | 9/1981 | Lechtken et al. |
| 4,298,738 A | 11/1981 | Lechtken et al. |
| 4,324,744 A | 4/1982 | Lechtken et al. |
| 4,385,109 A | 5/1983 | Lechtken et al. |
| 4,619,998 A | 10/1986 | Buhr |

(Continued)

FOREIGN PATENT DOCUMENTS

| | | |
|---|---|---|
| EP | 0911656 A2 | 4/1999 |
| EP | 1174411 A2 | 1/2002 |

(Continued)

OTHER PUBLICATIONS

Destrade et al., "Disc-Like Mesogens: A Classification," Molecular Crystals and Liquid Crystals, vol. 71, Nos. 1 and 2, 1981, pp. 111-135.

(Continued)

*Primary Examiner* — Shean C Wu
(74) *Attorney, Agent, or Firm* — Birch, Stewart, Kolasch & Birch, LLP

(57) ABSTRACT

A compound represented by the following formula (1) has sufficient solubility, a wide usable concentration range, and excellent haze-lowering performance. In the formula, $L^1$ to $L^6$ represent a single bond, —O—, —CO—, —COO—, etc; $Sp^1$ to $Sp^4$ represent a single bond or alkylene of 1 to 10 carbon atoms; $A^1$ and $A^2$ represent trivalent or tetravalent aromatic hydrocarbon or heterocyclic; T represents the following formulae, etc; Hb represent perfluoroalkyl of 2 to 30 carbon atoms; m and n are 2 or 3; and o and p are an integer of 0 or more.

(1)

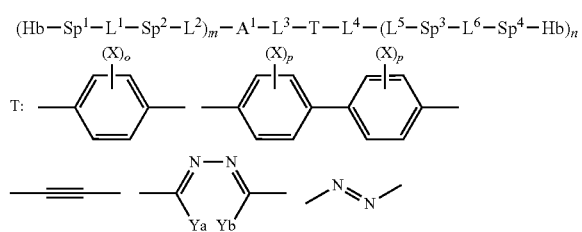

13 Claims, 1 Drawing Sheet

(56) References Cited

U.S. PATENT DOCUMENTS

| | | |
|---|---|---|
| 4,696,888 A | 9/1987 | Buhr |
| 4,710,523 A | 12/1987 | Lechtken et al. |
| 4,737,593 A | 4/1988 | Ellrich et al. |
| 4,792,632 A | 12/1988 | Ellrich et al. |
| 5,635,105 A | 6/1997 | Kawata et al. |
| 5,747,121 A | 5/1998 | Okazaki et al. |
| 5,942,290 A | 8/1999 | Leppard et al. |
| 6,020,528 A | 2/2000 | Leppard et al. |
| 6,284,813 B1 | 9/2001 | Leppard et al. |
| 6,338,808 B1 | 1/2002 | Kawata et al. |
| 6,361,925 B1 | 3/2002 | Leppard et al. |
| 6,485,798 B1 | 11/2002 | Aminaka et al. |
| 6,875,483 B2 | 4/2005 | Ichihashi et al. |
| 2002/0039627 A1 | 4/2002 | Ichihashi et al. |
| 2002/0042022 A1 | 4/2002 | Leppard et al. |
| 2014/0339470 A1* | 11/2014 | Katoh .................... C07C 65/21 252/299.5 |

FOREIGN PATENT DOCUMENTS

| | | |
|---|---|---|
| EP | 1174411 A3 | 3/2002 |
| EP | 1174411 B1 | 10/2003 |
| JP | 60-105667 A | 6/1985 |
| JP | 63-40799 B2 | 8/1988 |
| JP | 5-29234 B2 | 4/1993 |
| JP | 7-333433 A | 12/1995 |
| JP | 8-27284 A | 1/1996 |
| JP | 9-152509 A | 6/1997 |
| JP | 10-29997 A | 2/1998 |
| JP | 10-95788 A | 4/1998 |
| JP | 2000-345164 A | 12/2000 |
| JP | 2002-97170 A | 4/2002 |
| JP | 2002-129162 A | 5/2002 |

OTHER PUBLICATIONS

International Preliminary Report on Patentability (Forms PCT/IB/373 and PCT/ISA/237) for International Application No. PCT/JP2012/066957, dated Feb. 6, 2014, with an English translation.

International Search Report and Written Opinion of the International Searching Authority (Forms PCT/ISA/210, PCT/ISA/220, and PCT/ISA/237) for International Application No. PCT/JP2012/066957, dated Oct. 2, 2012, with an English translation of the International Search Report.

Kikan Kagaku Sosetsu, "Liquid Crystal Chemistry," The Chemical Society of Japan, No. 22, Chapter 5, Chapter 10, Section 2, 1994, 29 pages.

Lehn et al., "Tubular Mesophases: Liquid Crystals consisting of Macrocyclic Molecules," Journal of the Chemical Society, Chemical Communication, No. 24, Dec. 15, 1985, pp. 1794-1796.

Zhang et al., "Liquid Crystals Based on Shape-Persistent Macrocyclic Mesogens," Journal of American Chemical Society, vol. 116, No. 6, 1994, pp. 2655-2656.

* cited by examiner

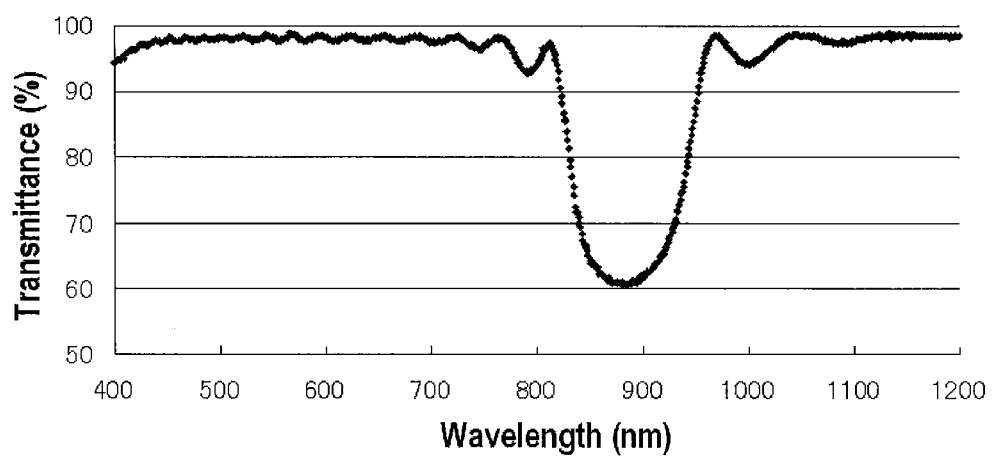

COMPOUND, HAZE-LOWERING AGENT, LIQUID CRYSTAL COMPOSITION, POLYMER MATERIAL, AND FILM

CROSS-REFERENCE TO RELATED APPLICATIONS

This application is a continuation application of International Application No. PCT/JP2012/066957, filed Jul. 3, 2012, which in turn claims the benefit of priority from Japanese Application No. 2011-164777, filed Jul. 27, 2011, and Japanese Application No. 2012-036512, filed Feb. 22, 2012, the disclosures of which applications are incorporated by reference herein in their entirety.

BACKGROUND OF THE INVENTION

1. Field of the Invention

The present invention relates to compounds and haze-lowering agents useful in a variety of applications, including materials of various types of optical members such as optically anisotropic films and heat shield films, and to liquid crystal compositions and polymer materials containing such compounds and haze-lowering agents. The invention also relates to films that use such materials.

2. Background Art

Liquid crystals orderly align themselves upon being applied onto a film subjected to an alignment process (alignment film). The alignment state of liquid crystal can be controlled with the use of two alignment films disposed on the both sides of the liquid crystal. An example of such a structure is a liquid crystal display device that includes a liquid crystal cell constructed from rod-like liquid crystal molecules and a pair of substrates sealing the liquid crystal molecules, and an electrode layer provided to apply voltage to the rod-like liquid crystal molecules. In such a liquid crystal display device, the rod-like liquid crystal molecules are injected into the gap between the alignment films formed on the two substrates, and the alignment state of the rod-like liquid crystal molecules can be controlled relatively easily.

On the other hand, it has been proposed to dispose an optical compensation sheet (retardation plate) between a liquid crystal cell and a polarizing plate for the purpose of increasing the viewing angle or preventing coloring of a liquid crystal display device. In this case, an optically anisotropic element having an optically anisotropic layer formed from liquid crystal molecules is used as an optical compensation sheet on a transparent support. The optically anisotropic layer is formed by aligning liquid crystal molecules, and fixing the alignment state. Here, the liquid crystal molecules are aligned with a single alignment film provided between the transparent support and the optically anisotropic layer. However, it is difficult with a single alignment film to uniformly align (monodomain alignment) the liquid crystal molecules from the alignment film interface to the air interface. This is because of the disturbed liquid crystal alignment due to the lack of alignment regulation on the side of the interface (air interface) not subjected to an alignment process. Non-uniform alignment of liquid crystal molecules causes scattering of light due to disclination, and a nontransparent film is formed. Such a film is not desirable from the standpoint of improving the viewability of the liquid crystal display device.

Out of these needs, techniques are developed that regulate alignment of a liquid crystal and uniformly align the liquid crystal also on the side of the interface (air interface) not subjected to an alignment process, without using an alignment film (Patent Documents 1 and 2). In these techniques, alignment of the liquid crystal molecules is controlled by adding a liquid crystal alignment promoting agent. By using a liquid crystal alignment promoting agent, a liquid crystal composition is provided that allows liquid crystal molecules to uniformly align themselves with ease.

CITATION LIST

Patent Documents

Patent Document 1: JP-A-2002-129162
Patent Document 2: JP-A-2000-345164

SUMMARY OF THE INVENTION

However, the liquid crystal alignment promoting agents described in Patent Documents 1 and 2 are not necessarily sufficient in terms of usable concentration range and solubility, and need further improvements. There is accordingly a need for a material that has a liquid crystal alignment promoting effect at least comparable to that of the liquid crystal alignment promoting agents described in Patent Documents 1 and 2, and that can lower the haze of the product film. It is accordingly an object of the present invention to solve the foregoing problems of related art, and provide a compound having sufficient solubility, a wide usable concentration range, and excellent haze-lowering performance. Another object is to provide a novel liquid crystal composition that can lower the haze of the product film by allowing liquid crystal molecules to uniformly align themselves with ease or the like. Specifically, the present invention is intended to provide a compound useful for a variety of applications, including materials of various types of optical members such as optically anisotropic films and heat shield films. The invention is also intended to provide a liquid crystal composition and a polymer material containing such a compound, and a film that uses such materials.

The foregoing problems are solved by the following means.

[1] A compound represented by the following formula (I):

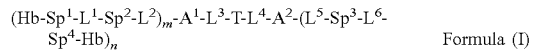

wherein $L^1$, $L^2$, $L^3$, $L^4$, $L^5$, and $L^6$ each independently represent a single bond, —O—, —S—, —CO—, —COO—, —COO—, —COS—, —SCO—, —NRCO—, or —CONR—, R in the formula (I) each independently represent a hydrogen atom or an alkyl group of 1 to 6 carbon atoms, $Sp^1$, $Sp^2$, $Sp^3$, and $Sp^4$ each independently represent a single bond or an alkylene group of 1 to 10 carbon atoms in which each of the hydrogen atoms of the alkylene group may be substituted with a fluorine atom, $A^1$ and $A^2$ represent a trivalent or tetravalent aromatic hydrocarbon group, T represents a divalent group or a divalent aromatic heterocyclic group of the following formulae:

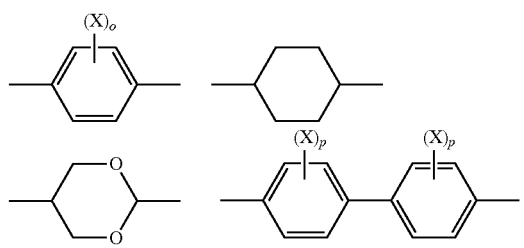

-continued

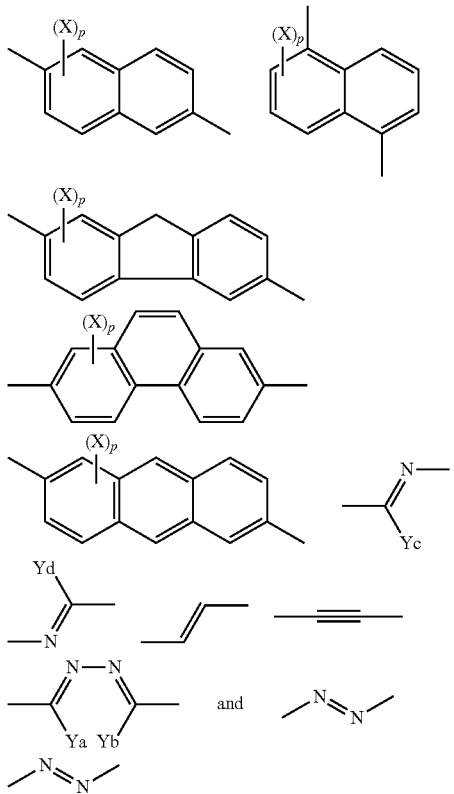

wherein X represents an alkyl group of 1 to 8 carbon atoms, an alkoxy group, a halogen atom, a cyano group, or —COOR⁰ in which R⁰ represents a hydrogen atom, an alkyl or fluoroalkyl group in which each of the linking CH₂ may be substituted with O or S, or -Sp⁵-P in which Sp⁵ represents a single bond or an alkylene group of 1 to 10 carbon atoms in which each of the hydrogen atoms of the alkylene group may be substituted with a fluorine atom, and P represents a polymerizable group, Ya, Yb, Yc, and Yd each independently represent a hydrogen atom or an alkyl group of 1 to 4 carbon atoms, Hb's each independently represent a perfluoroalkyl or fluoroalkyl group of 2 to 30 carbon atoms, m and n are each independently 2 or 3, and the structures in a plurality of parentheses may be the same or different, o and p are each independently an integer of 0 or more, and a plurality of X when o and p are 2 or more may be the same or different.

[2] It is preferable in the compound of [1] that T in the formula (I) is

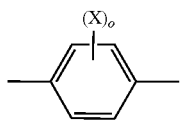

wherein o represents an integer of 0 or more, and X may be the same or different when o is 2 or more.

[3] It is preferable in the compound of [1] or [2] that, in the formula (I), L³ is —COO—, L⁴ is —OCO—, and A¹ and A² are each independently any one of the following:

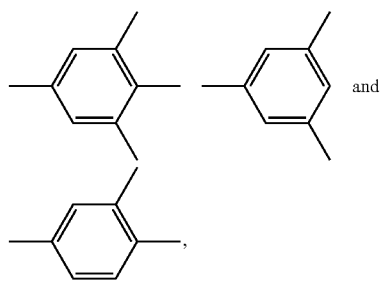

and

L² and L⁵ are —O—.

[4] It is preferable in the compound of any one of [1] to [3] that Hb's in the formula (I) are independently perfluoroalkyl of 2 to 30 carbon atoms.

[5] A haze-lowering agent that uses the compound of any one of [1] to [4].

[6] A liquid crystal composition that comprises a polymerizable liquid crystal molecule, and a compound represented by the following formula (I):

$$(Hb-Sp^1-L^1-Sp^2-L^2)_m-A^1-L^3-T-L^4-A^2-(L^5-Sp^3-L^6-Sp^4-Hb)_n \qquad \text{Formula (I)}$$

wherein L¹, L², L³, L⁴, L⁵, and L⁶ each independently represent a single bond, —O—, —S—, —CO—, —COO—, —OCO—, —COS—, —SCO—, —NRCO—, or —CONR—, R in the formula (I) each independently represent a hydrogen atom or an alkyl group of 1 to 6 carbon atoms, Sp¹, Sp², Sp³, and Sp⁴ each independently represent a single bond or an alkylene group of 1 to 10 carbon atoms in which each of the hydrogen atoms of the alkylene group may be substituted with a fluorine atom, A¹ and A² represent a trivalent or tetravalent aromatic hydrocarbon group, T represents a divalent group or a divalent aromatic heterocyclic group of the following formulae:

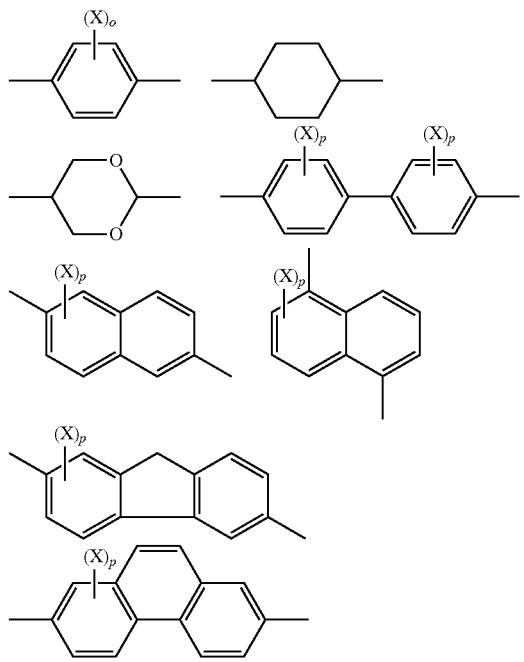

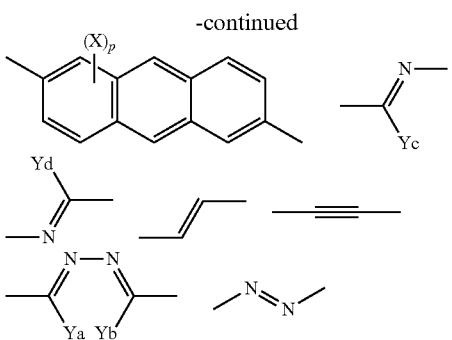

wherein X represents an alkyl group of 1 to 8 carbon atoms, an alkoxy group, a halogen atom, a cyano group, or —COOR⁰ in which R⁰ represents a hydrogen atom, an alkyl or fluoroalkyl group in which each of the linking $CH_2$ may be substituted with O or S, or -Sp⁵-P in which $Sp^5$ represents a single bond or an alkylene group of 1 to 10 carbon atoms in which each of the hydrogen atoms of the alkylene group may be substituted with a fluorine atom, and P represents a polymerizable group, Ya, Yb, Yc, and Yd each independently represent a hydrogen atom or an alkyl group of 1 to 4 carbon atoms, Hb's each independently represent a perfluoroalkyl or fluoroalkyl group of 2 to 30 carbon atoms, m and n are each independently 2 or 3, and the structures in a plurality of parentheses may be the same or different, o and p are each independently an integer of 0 or more, and a plurality of X when o and p are 2 or more may be the same or different.

[7] It is preferable in the liquid crystal composition of [6] that the polymerizable liquid crystal molecule is a rod-like liquid crystal molecule.

[8] It is preferable that the liquid crystal composition of [6] or [7] contain at least one chiral compound.

[9] A polymer material produced by polymerizing the liquid crystal composition of any one of [6] to [8].

[10] A film that contains at least one polymer material of [9].

[11] A film with a fixed cholesteric liquid crystal phase of the liquid crystal composition of any one of [6] to [8].

[12] It is preferable that the film of [10] or [11] have optical anisotropy.

[13] It is preferable that film of any one of [10] to [12] have a selective reflection property.

[14] It is preferable that the film of [13] has a selective reflection property in an infrared wavelength region.

The present invention uses a compound of formula (I) having a wide usable concentration range, high solvent solubility, and high haze lowering effect, and can provide a liquid crystal composition and a polymer material useful for a variety of applications, including materials of various types of optical members such as optically anisotropic films and heat shield films. The invention also can provide a film that uses such materials.

BRIEF DESCRIPTION OF THE DRAWINGS

FIG. 1 represents a transmission spectrum of a film produced with compound (2) used as a haze-lowering agent in Example 25.

MODE FOR CARRYING OUT THE INVENTION

The present invention is described below in detail. The descriptions of the constituting elements below, including the representative embodiments and concrete examples thereof according to the present invention, serve solely to illustrate the present invention, and the present invention is not limited by such embodiments and concrete examples. As used herein, the numerical ranges defined with "to" are intended to be inclusive of the numbers specified by "to" as the lower limit and the upper limit.

[Compound of Formula (I), and Haze-Lowering Agent]

The compound of the present invention is represented by the formula (I) below. The compound of the formula (I) has a center divalent group, and terminal alkyl. Compounds with terminal fluoroalkyl are effective as alignment promoting agents. However, conventional alignment promoting agents are limited to certain uses because of the narrow usable concentration range and low solubility. The compound represented by the formula (I) below has comparable or even greater alignment performance in a wider concentration range with more desirable solubility, and can desirably be used as a haze-lowering agent. The compound represented by the formula (I) also can be desirably used as a liquid crystal alignment promoting agent. One of the advantages of a composition containing the compound represented by the following formula (I) is that it is easy to use for production. Further, because the compound is curable through polymerization, it is useful in a variety of applications, including optical members.

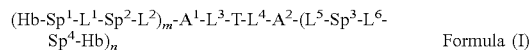

Formula (I)

In the formula (I), $L^1$, $L^2$, $L^3$, $L^4$, $L^5$, and $L^6$ each independently represent a single bond, —O—, —S—, —CO—, —COO—, —OCO—, —COS—, —SCO—, —NRCO—, or —CONR— (R in the formula (I) represents a hydrogen atom, or an alkyl group of 1 to 6 carbon atoms), more preferably —O—, —S—, —CO—, —COO—, —OCO—, —COS—, —SCO— because —NRCO— and —CONR— have the effect to lower solubility, and tend to increase haze value during film production, and further preferably —O—, —CO—, —COO—, —OCO— from the standpoint of compound stability. The alkyl group represented by R may be linear or branched, and has preferably 1 to 3 carbon atoms. Examples include a methyl group, an ethyl group, and a n-propyl group.

$Sp^1$, $Sp^2$, $Sp^3$, and $Sp^4$ each independently represent a single bond or an alkylene group of 1 to 10 carbon atoms, more preferably a single bond or an alkylene group of 1 to 7 carbon atoms, further preferably a single bond or an alkylene group of 1 to 4 carbon atoms. Each of the hydrogen atoms of the alkylene group may be substituted with a fluorine atoms. The alkylene group may be branched or unbranched, and is preferably unbranched linear alkylene. From the standpoint of synthesis, preferably, $Sp^1$ and $Sp^4$ are the same, and $Sp^2$ and $Sp^3$ are the same.

$A^1$ and $A^2$ represent a trivalent or tetravalent aromatic hydrocarbon group. The trivalent or tetravalent aromatic hydrocarbon group has preferably 6 to 22 carbon atoms, more preferably 6 to 14 carbon atoms, further preferably 6 to 10 carbon atoms, even more preferably 6 carbon atoms. The trivalent or tetravalent aromatic hydrocarbon group represented by $A^1$ and $A^2$ may have optional substituents. Examples of such substituents include an alkyl group of 1 to 8 carbon atoms, an alkoxy group, a halogen atom, a cyano group, and an ester group. The corresponding descriptions for T below should be referred to for explanations and the preferred ranges of these groups. Examples of the substituents for the trivalent or tetravalent aromatic hydrocarbon group represented by $A^1$ and $A^2$ include a methyl group, an ethyl group, a methoxy group, an ethoxy group, a bromine atom, a chlorine atom, and a cyano group. Preferably, $A^1$ and $A^2$ are tetravalent to contain more perfluoroalkyl moieties within the molecule, because molecules containing larger numbers of perfluoroalkyl moieties within the molecule can align a liquid crystal with less addition amounts, and can thus lower the haze. From the standpoint of synthesis, $A^1$ and $A^2$ are the same.

T represents a divalent group or a divalent aromatic heterocyclic group of the following formulae:

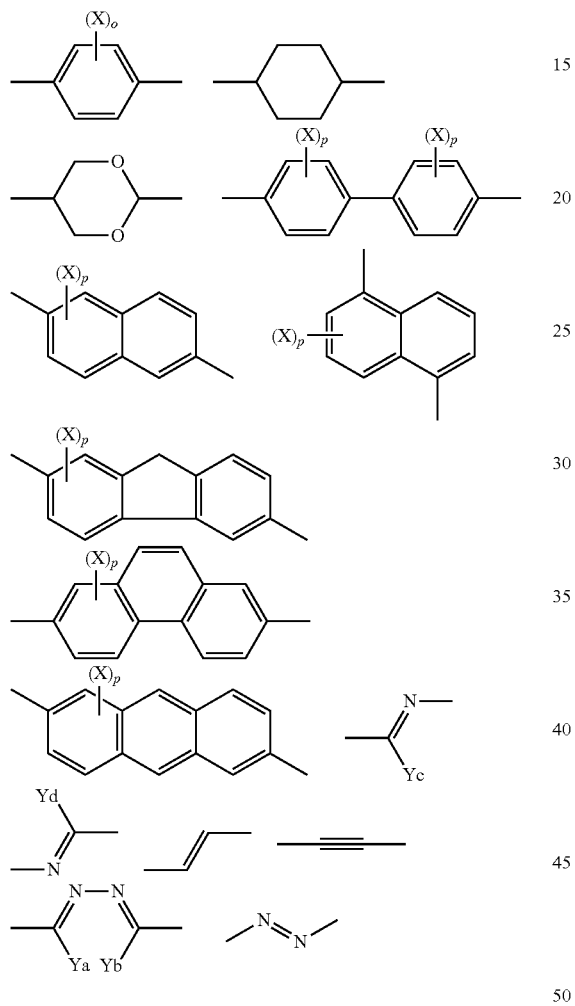

wherein X represents alkyl of 1 to 8 carbon atoms, alkoxy, a halogen atom, cyano, or R'COO— (R' represents a hydrogen atom; alkyl or fluoroalkyl in which linking $CH_2$ may be substituted with O or S; or $Sp^5$-P, wherein $Sp^5$ represents a single bond or alkylene of 1 to 10 carbon atoms (the hydrogen atoms of the alkylene may be substituted with fluorine atoms), and P represents a polymerizable group), Ya, Yb, Yc, and Yd each independently represent a hydrogen atom or alkyl of 1 to 4 carbon atoms; more preferably:

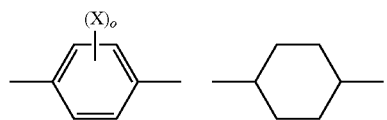

-continued

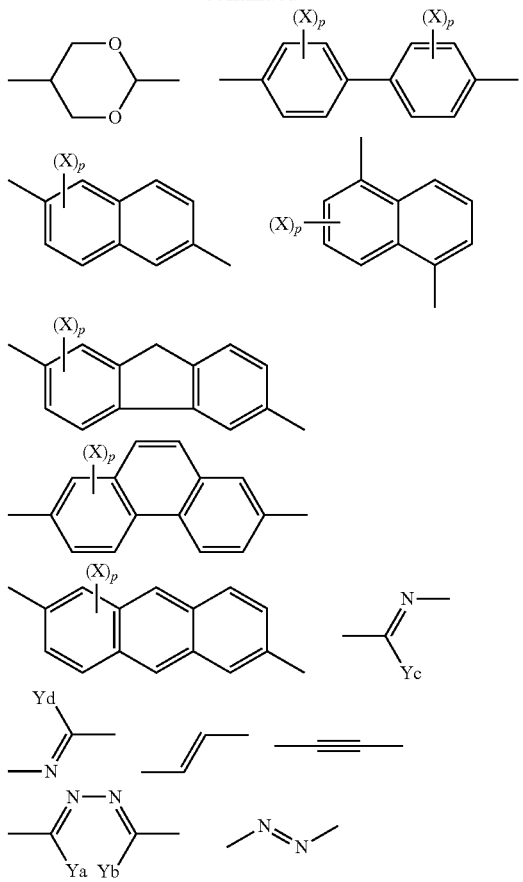

further preferably:

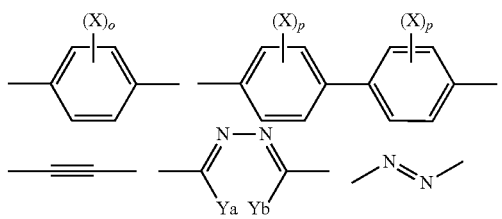

even more preferably:

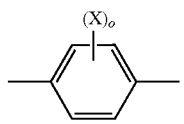

The alkyl group represented by X has 1 to 8 carbon atoms, preferably 1 to 5 carbon atoms, more preferably 1 to 3 carbon atoms. The alkyl group may be linear, branched, or cyclic, and is preferably linear or branched. Preferred examples of the alkyl group include a methyl group, an ethyl group, a n-propyl group, and an isopropyl group, of which methyl is more preferred. The descriptions and the preferred ranges of the alkyl represented by X should be referred to for the alkyl moiety of the alkoxy group represented by X.

Examples of the halogen atom represented by X include a fluorine atom, a chlorine atom, a bromine atom, and an iodine atom, of which a chlorine atom and a bromine atom are preferred.

The —$COOR^O$ represented by X may be one in which $R^O$ represents a hydrogen atom; an alkyl or fluoroalkyl group in which linking $CH_2$ may be substituted with O or S; or -$Sp^5$-P.

When $R^O$ represents an alkyl or fluoroalkyl group in which linking $CH_2$ may be substituted with O or S, the group is preferably one represented by -$Sp^6$-($L^7$-$Sp^7$)$_q$-$CH_3$ or -$Sp^8$-($L^8$-$Sp^9$)$_r$-$Hb^0$.

$Sp^6$, $Sp^7$, $Sp^8$, and $Sp^9$ each independently represent a single bond or an alkylene group of 1 to 10 carbon atoms, preferably a single bond or an alkylene group of 1 to 7 carbon atoms, more preferably a single bond or an alkylene group of 1 to 4 carbon atoms. Each of the hydrogen atoms of the alkylene group represented by $Sp^6$, $Sp^7$, $Sp^8$, and $Sp^9$ may be substituted with a fluorine atom, and is preferably not substituted with a fluorine atom. The alkylene group may be branched or unbranched, and is preferably unbranched linear alkylene group.

$L^7$ and $L^8$ each independently represent a single bond, —O—, —S—, —CO—, —COO—, —OCO—, —COS—, —SCO—, —NRCO—, —CONR— (R in $L^7$ and $L^8$ represents a hydrogen atom or an alkyl group of 1 to 6 carbon atoms), more preferably —O—, —S—, —CO—, —OCO—, —OCO—, —COS—, or —SCO— because —NRCO— and —CONR— have the effect to lower solubility, and tend to increase the haze value during film production, further preferably —O—, —CO—, —COO—, —OCO—, even more preferably —O— from the standpoint of compound stability.

q represents an integer of 1 to 4, preferably an integer of 1 to 3, more preferably 2 or 3, particularly preferably 3. r represents an integer of 1 to 4, preferably an integer of 1 to 3, more preferably 1 or 2, particularly preferably 1. When q and r are integers of 2 or more, a plurality of $L^7$, $L^8$, $Sp^7$, and $Sp^9$ may be independent or different from each other.

$Hb^0$ represents a perfluoroalkyl or fluoroalkyl group of 2 to 30 carbon atoms, more preferably a perfluoroalkyl or fluoroalkyl group of 3 to 20 carbon atoms, further preferably a perfluoroalkyl or fluoroalkyl group of 3 to 10 carbon atoms. The perfluoroalkyl or fluoroalkyl group may be linear, branched, or cyclic, and are preferably linear or branched, more preferably linear. $Hb^0$ representing a perfluoroalkyl group of 2 to 30 carbon atoms, or a fluoroalkyl group of 2 to 30 carbon atoms is preferably a perfluoroalkyl group of 2 to 30 carbon atoms.

When $R^O$ represents -$Sp^5$-P, $Sp^5$ represents a single bond or an alkylene group of 1 to 10 carbon atoms, preferably a single bond or an alkylene group of 1 to 7 carbon atoms, more preferably an alkylene group of 1 to 4 carbon atoms. Each of the hydrogen atoms of the alkylene group represented by $Sp^5$ may be substituted with a fluorine atom. The alkylene group may be branched or unbranched, and is preferably an unbranched linear alkylene.

P represents a polymerizable group. The polymerizable group is not particularly limited, and is preferably an ethylenic unsaturated double bond group, more preferably a methacryloyl group or an acryloyl group, particularly preferably an acryloyl group.

The alkyl of 1 to 4 carbon atoms represented by Ya, Yb, Yc, and Yd may be linear or branched. Examples include a methyl group, an ethyl group, a n-propyl group, and an isopropyl group.

The divalent aromatic heterocyclic group preferably has a five-membered, six-membered, or seven-membered heterocyclic ring, preferably a five-membered ring or a six-membered ring, most preferably a six-membered ring. The heteroatom forming the heterocyclic ring is preferably a nitrogen atom, an oxygen atom, or a sulfur atom. The heterocyclic ring is preferably an aromatic heterocyclic ring. The aromatic heterocyclic ring is typically an unsaturated heterocyclic ring, preferably an unsaturated heterocyclic ring having the maximum number of double bonds. Examples of the heterocyclic ring include a furan ring, a thiophene ring, a pyrrole ring, a pyrroline ring, a pyrrolidine ring, an oxazole ring, an isooxazole ring, a thiazole ring, an isothiazole ring, an imidazole ring, an imidazoline ring, an imidazolysine ring, a pyrazole ring, a pyrazoline ring, a pyrazolidine ring, a triazole ring, a furazan ring, a tetrazole ring, a pyran ring, a thiin ring, a pyridine ring, a piperidine ring, an oxazine ring, a morpholine ring, a triazine ring, a pyridazine ring, a pyrimidine ring, a pyrazine ring, a piperazine ring, and a triazine ring. The divalent heterocyclic group may have optional substituents.

The explanations and the descriptions of the possible substituents of the trivalent or tetravalent aromatic hydrocarbon group represented by $A^1$ and $A^2$ should be referred to for explanations and the preferred ranges of these exemplary substituents.

Hb represents a perfluoroalkyl or fluoroalkyl group of 2 to 30 carbon atoms, more preferably a perfluoroalkyl or fluoroalkyl group of 3 to 20 carbon atoms, further preferably a perfluoroalkyl or fluoroalkyl group of 3 to 10 carbon atoms. The perfluoroalkyl or fluoroalkyl group may be linear, branched, or cyclic, preferably linear or branched, more preferably linear.

The fluoroalkyl group represented by Hb is preferably a fluoroalkyl group with terminal —$CF_2$—H, more preferably a fluoroalkyl group with —$CF_2$—H joined to one of the terminals of perfluoroalkylene moiety.

Hb representing a perfluoroalkyl group of 2 to 30 carbon atoms, or a fluoroalkyl group of 2 to 30 carbon atoms is preferably a perfluoroalkyl group of 2 to 30 carbon atoms.

m and n are each independently 2 or 3. The structures in a plurality of parentheses may be the same or different, and are preferably the same. m and n in the formula (I) are determined by the valency of $A^1$ and $A^2$, and the preferred ranges are also determined by the preferred valency ranges of $A^1$ and $A^2$. Though not bound by any theory, the greatly improved haze-lowering performance achieved despite small addition amounts of the compounds of the present invention in which m and n are 2 or 3 compared to conventional compounds in which n is 1 is considered to be due to the fluorine content in the compound.

o and p are each independently an integer of 0 or more, and a plurality of X when o and p are 2 or more may be the same or different. Preferably, o is 1 or 2. p is preferably an integer of 1 to 4, more preferably 1 or 2.

The compound represented by formula (I) may be one having a symmetric molecular structure, or may be a compound with no symmetry. As used herein, "symmetry" is intended to mean point symmetry, line symmetry, or rotational symmetry, and "asymmetry" means anything that is not classified into point symmetry, line symmetry, or rotational symmetry.

The compound represented by formula (I) is a compound that combines the perfluoroalkyl group (Hb), the linking groups -(-Sp-L-$Sp^2$-$L^1$-$Sp^2L^2$)$_m$-$A^1$-$L^3$- and -$L^4$-$A^2$-($L^5$-$Sp^3$-$L^6$-$Sp^4$-)$_n$-, and preferably the bivalent group T having an excluded volume effect. The two perfluoroalkyls (Hb)

that exist within the molecule are preferably the same, and the linking groups $-(-Sp-L-Sp^2-L^1-Sp^2L^2)_m-A^1-L^3-$ and $-L^4-A^2-(L^5-Sp^3-L^6-Sp^4-)_n-$ that exist within the molecule are preferably the same. The terminal $Hb-Sp^1-L^1-Sp^2-$ and $-Sp^3-L^6-Sp^4-Hb$ are preferably groups represented by any of the following formulae.

$(C_aF_{2a+1})-(C_bH_{2b})-$ $(C_aF_{2a+1})-(C_bH_{2b})-O-(C_rH_{2r})-$ $(C_aF_{2a+1})-(C_bH_{2b})-COO-(C_rH_{2r})-$ $(C_aF_{2a+1})-(C_bH_{2b})-OCO-(C_rH_{2r})-$

In the formulae, a is preferably 2 to 30, more preferably 3 to 20, further preferably 3 to 10. b is preferably 0 to 20, more preferably 0 to 10, further preferably 0 to 5. a+b is 3 to 30. r is preferably 1 to 10, more preferably 1 to 4.

The terminal $Hb-Sp^1-L^1-Sp^2-L^2-$ and $-L^5-Sp^3-L^6-Sp^4-Hb$ in formula (I) are preferably groups represented by any of the following formulae.

$(C_aF_{2a+1})-(C_bH_{2b})-O$ $(C_aF_{2a+1})-(C_bH_{2b})-COO-$ $(C_aF_{2a+1})-(C_bH_{2b})-O-(C_rH_{2r})-O-$ $(C_aF_{2a+1})-(C_bH_{2b})-COO-(C_rH_{2r})-COO-$ $(C_aF_{2a+1})-(C_bH_{2b})-OCO-(C_rH_{2r})-COO-$

The definitions of a, b, and r in these formulae are the same as above.

Specific examples of the compounds represented by formula (I) are given below. It should be noted, however, that the compounds of formula (I) usable in the present invention should not be narrowly interpreted within the limits of the following specific examples.

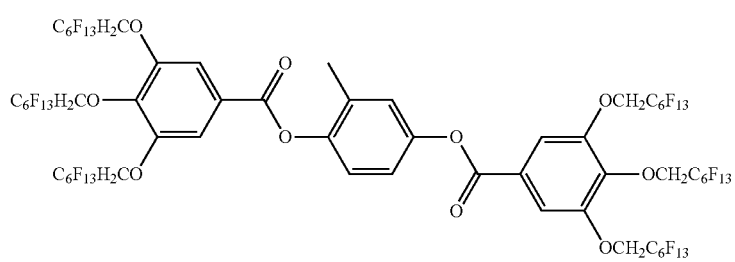

(1)

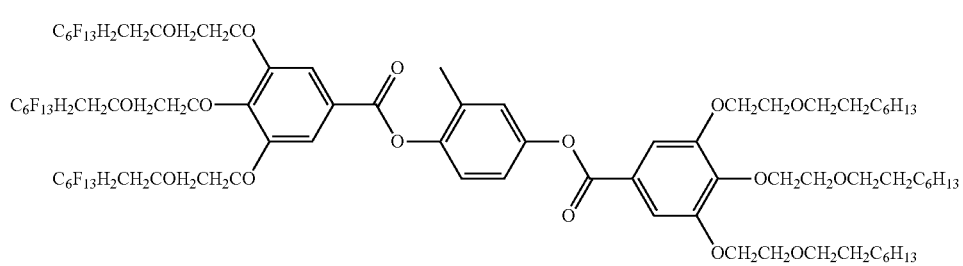

(2)

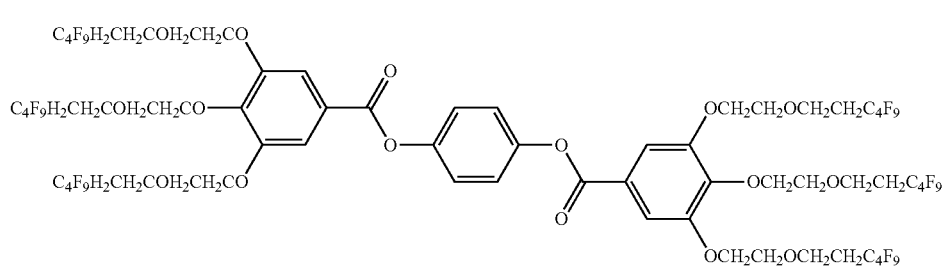

(3)

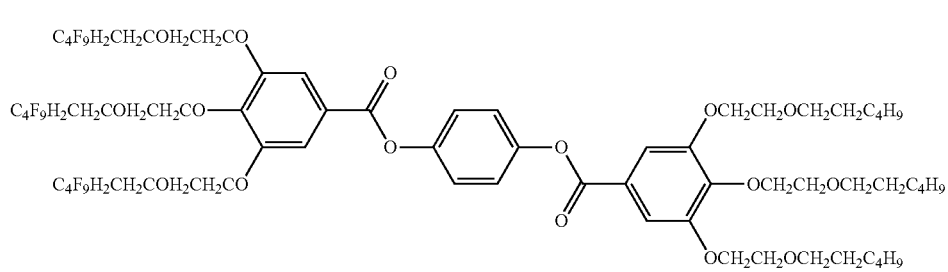

(4)

-continued
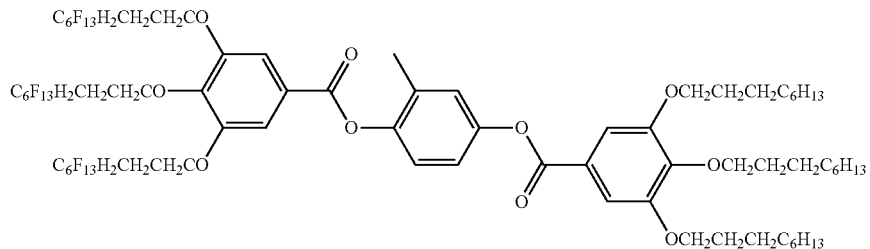
(5)
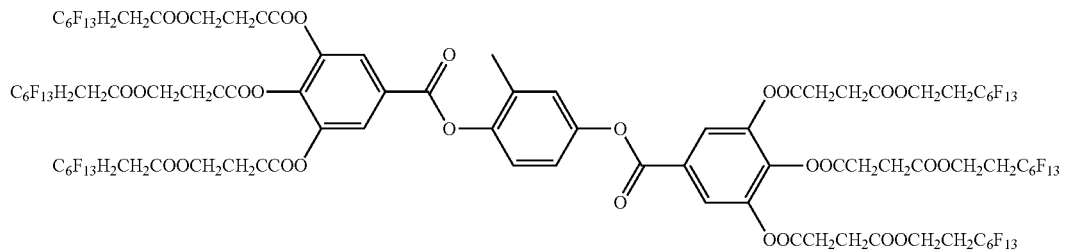
(6)
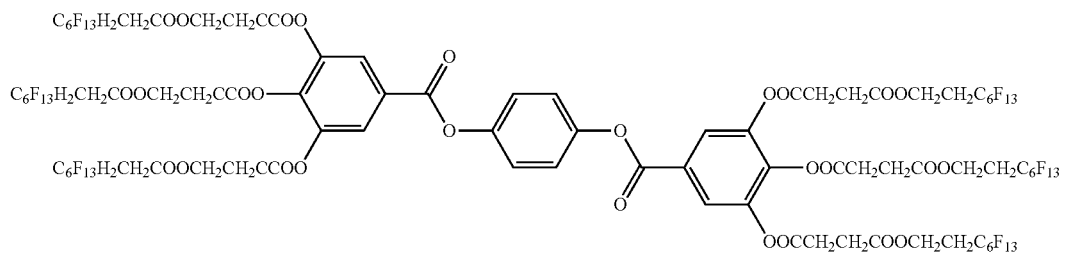
(7)
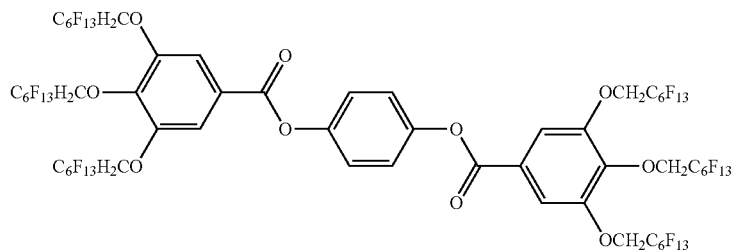
(8)
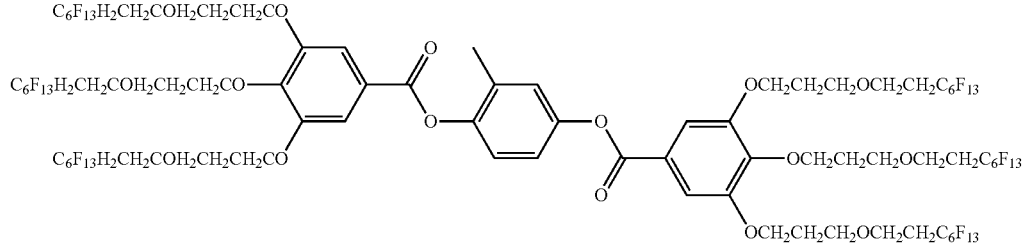
(9)
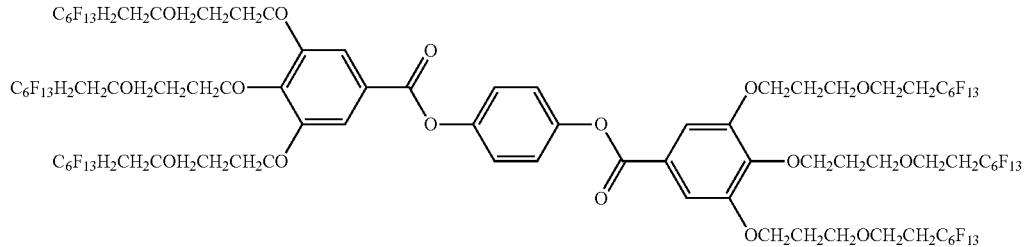
(10)

-continued
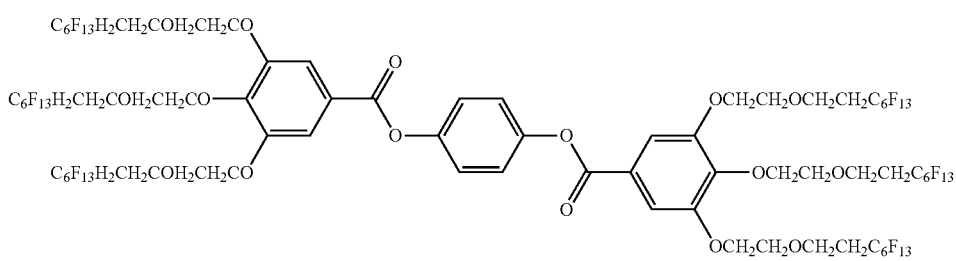
(11)
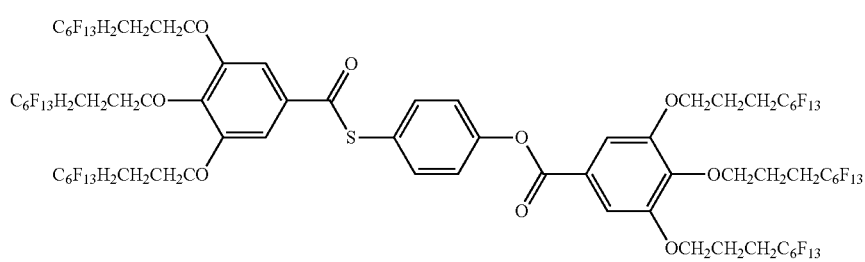
(12)
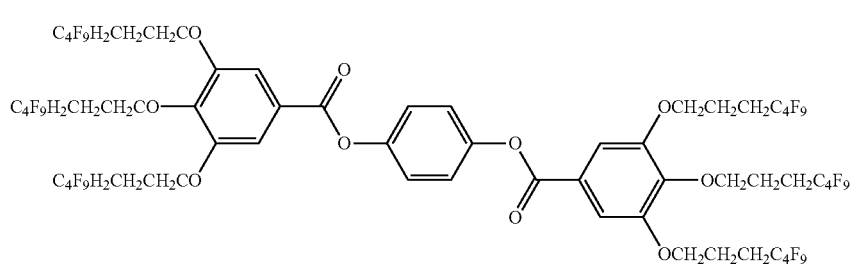
(13)
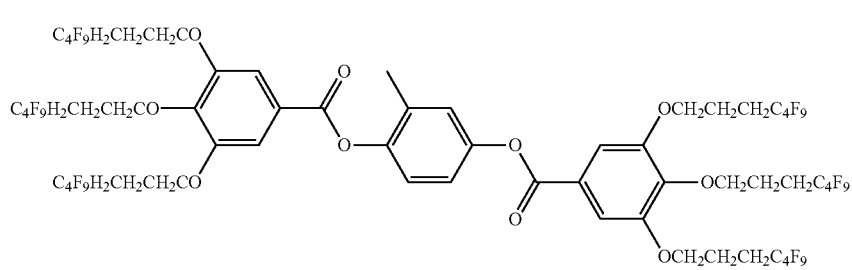
(14)
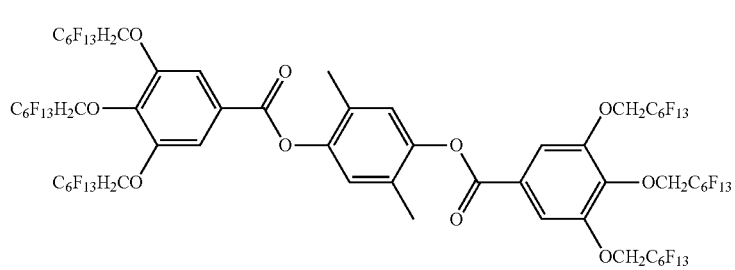
(15)
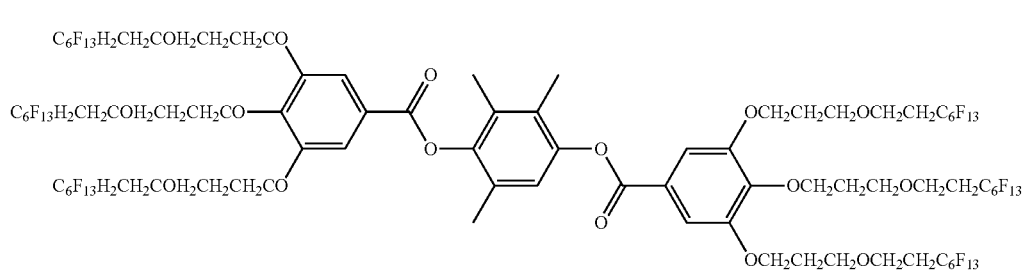
(16)

-continued
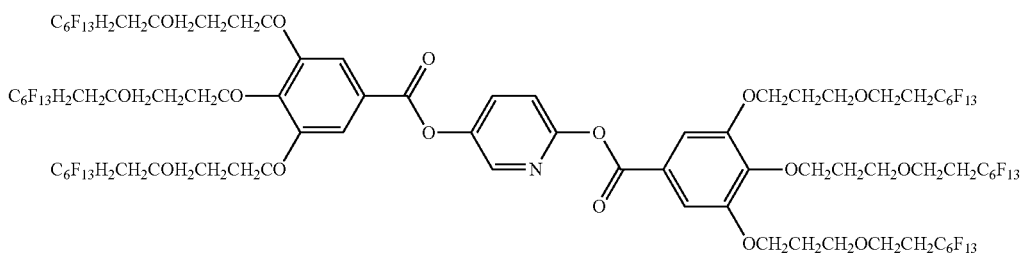
(17)
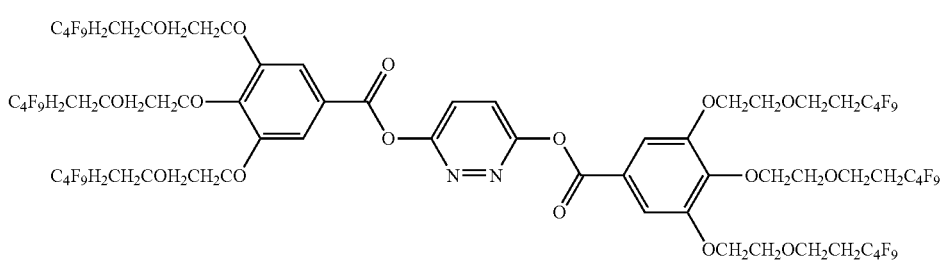
(18)
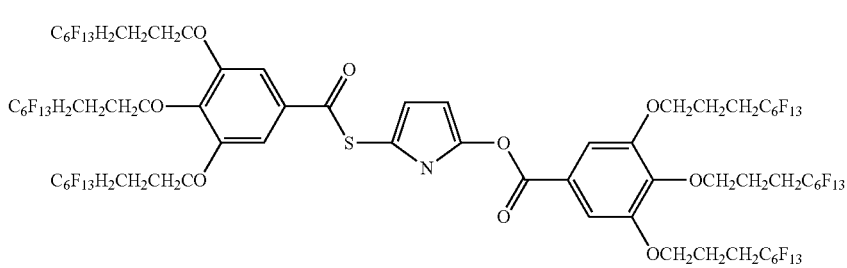
(19)
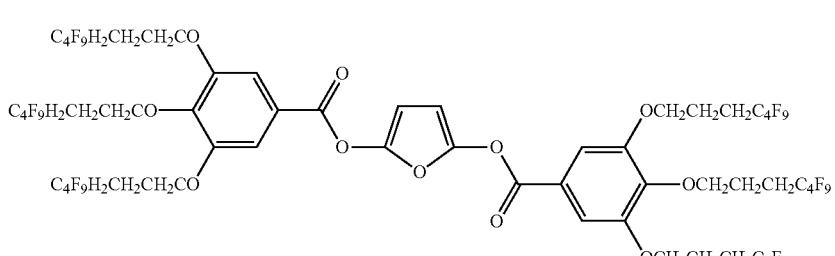
(20)
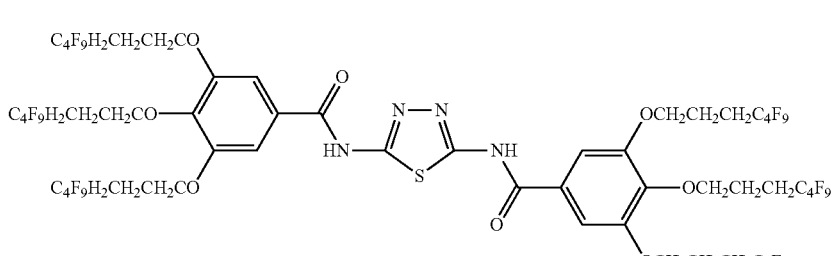
(21)
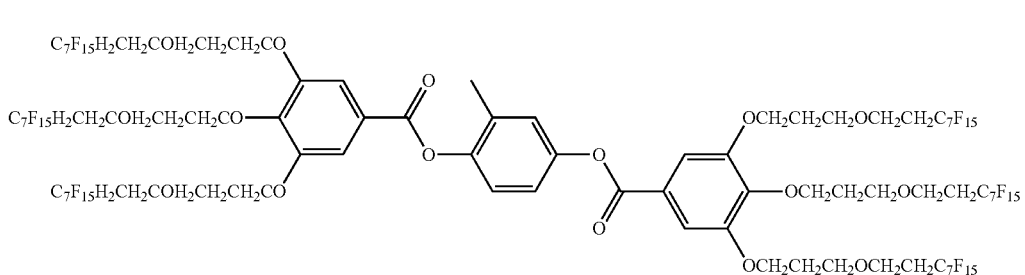
(22)

-continued
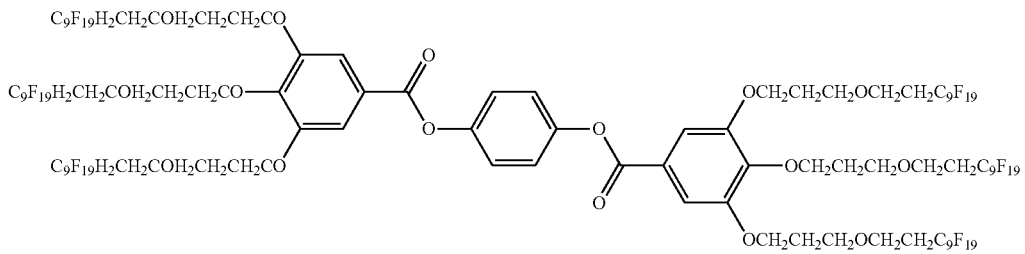
(23)
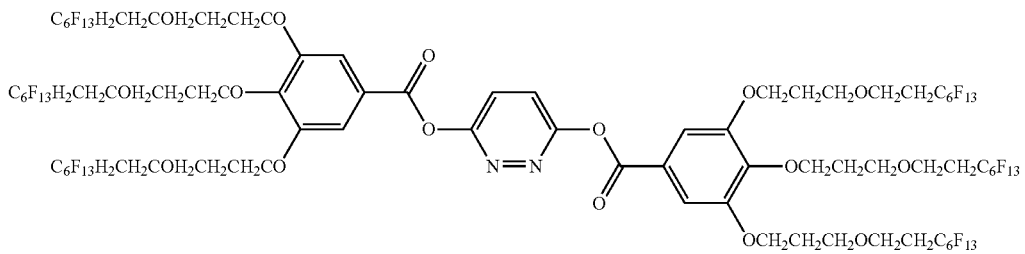
(24)
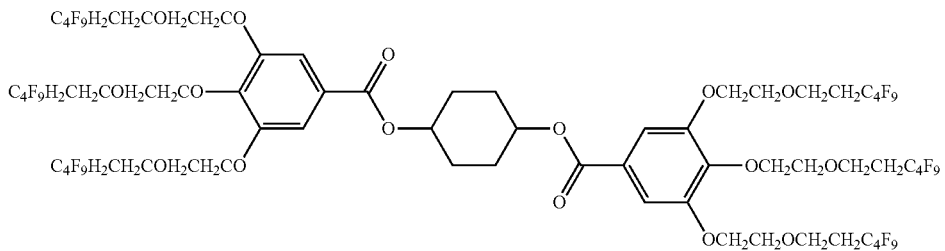
(25)
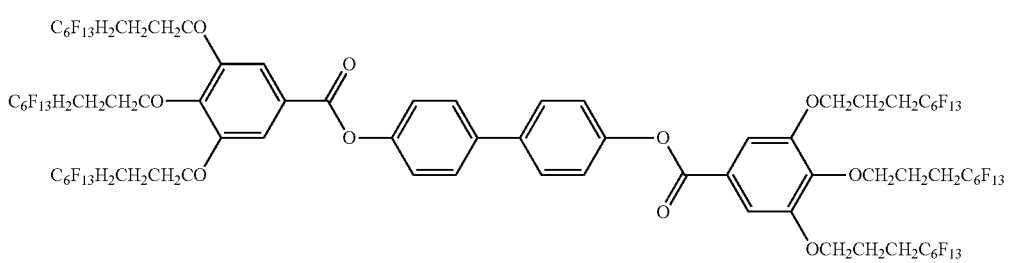
(26)
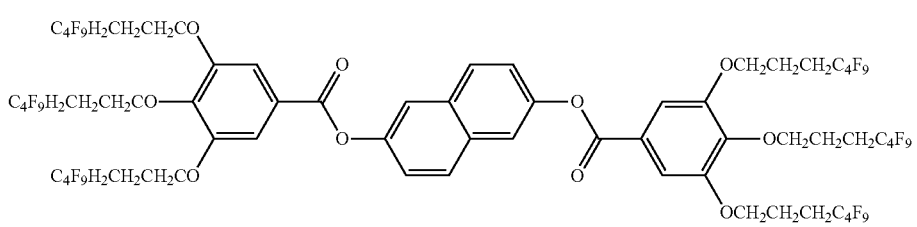
(27)
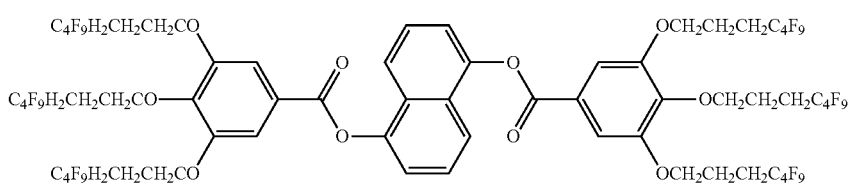
(28)

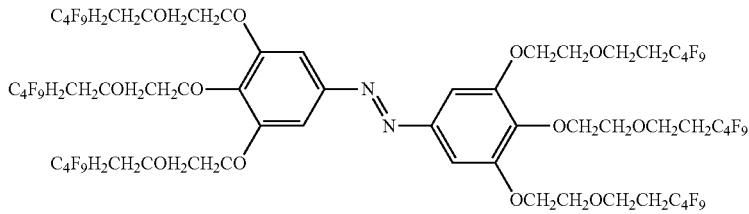
(29)
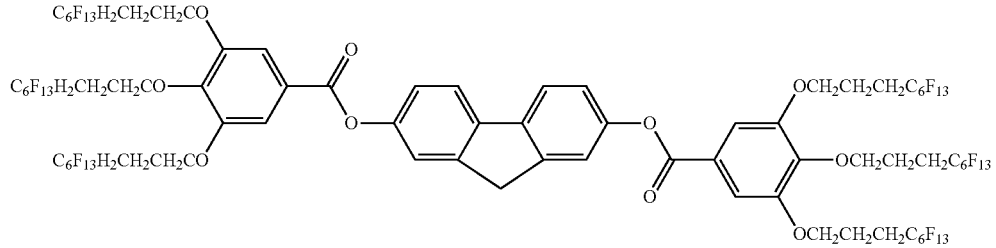
(30)
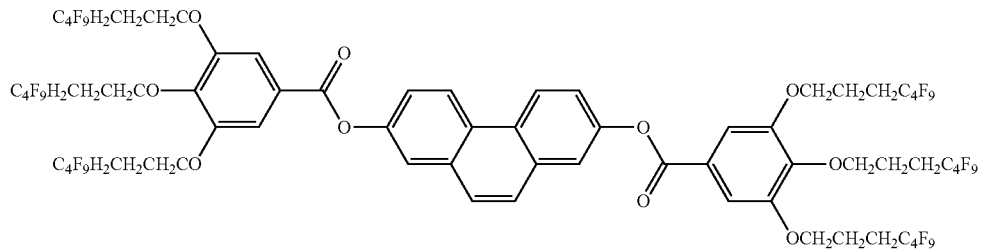
(31)
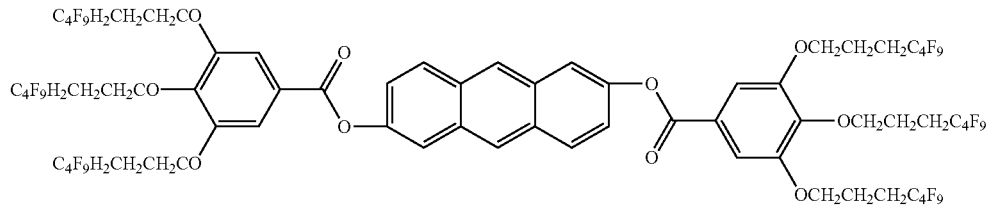
(32)
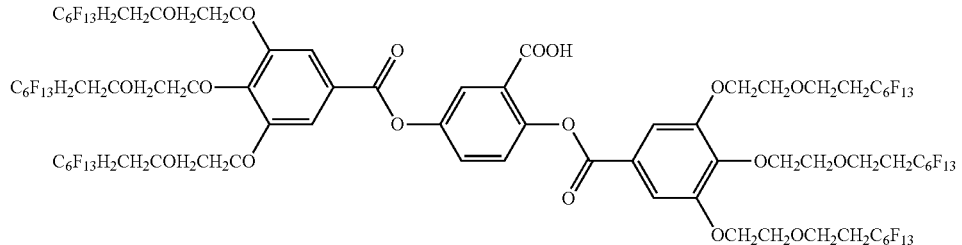
(33)
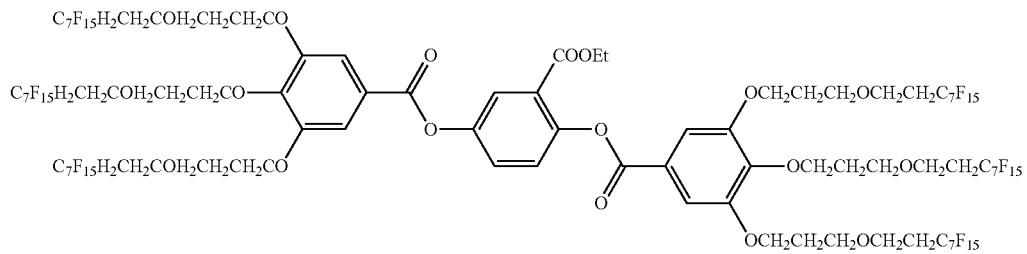
(34)

-continued
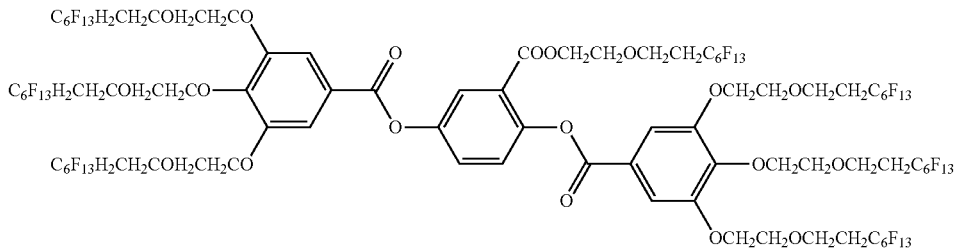
(35)
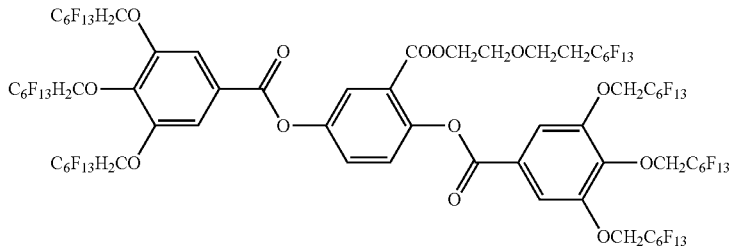
(36)
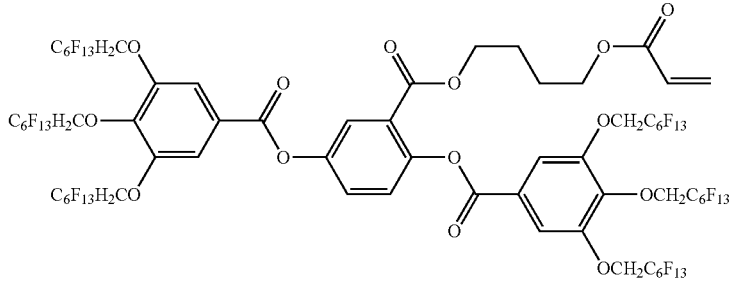
(37)
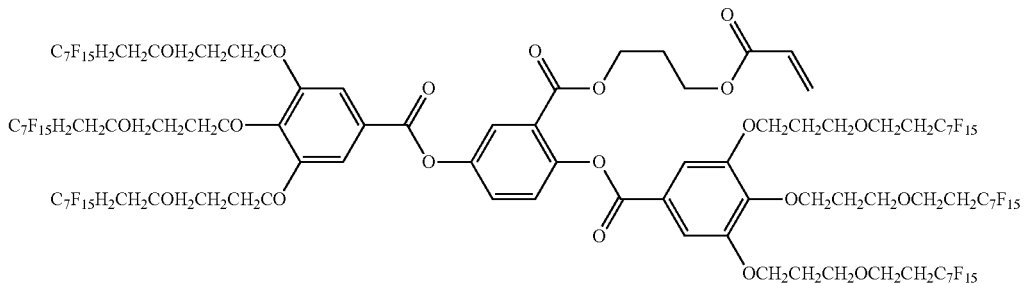
(38)
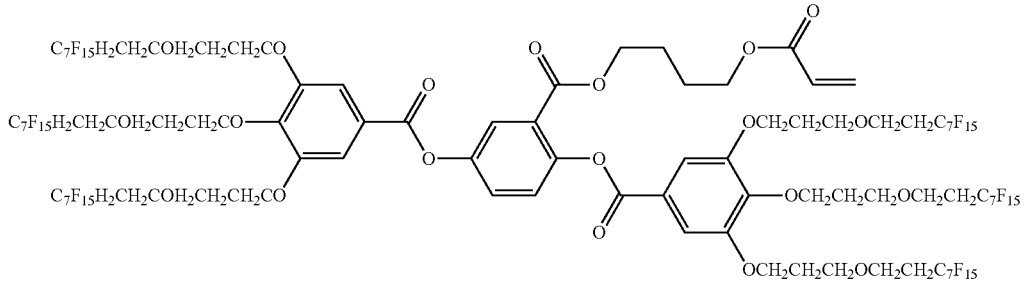
(39)
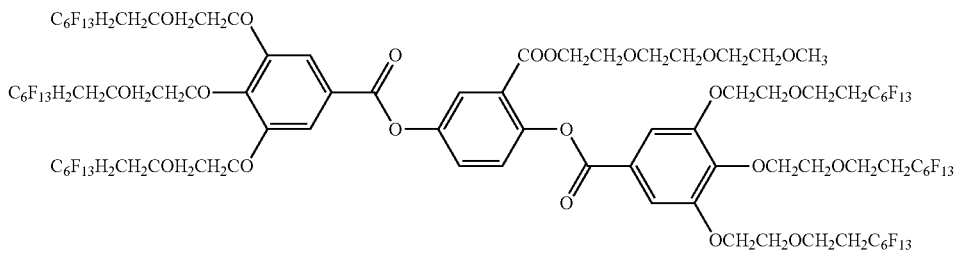
(40)

-continued
(41)
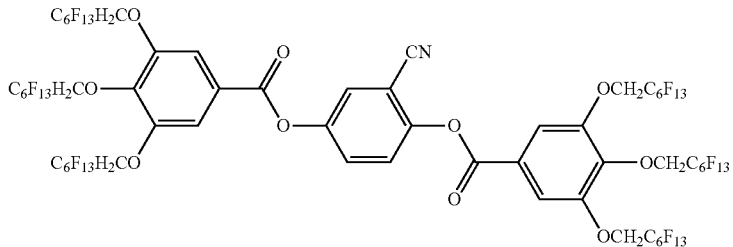
(42)
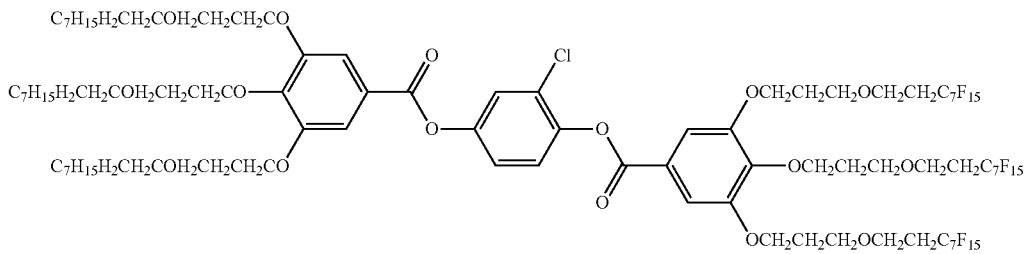
(43)
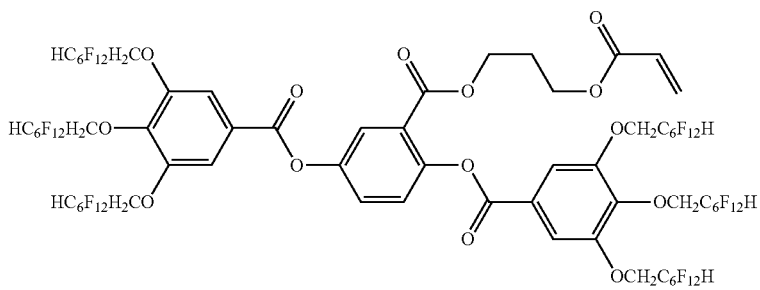
(44)
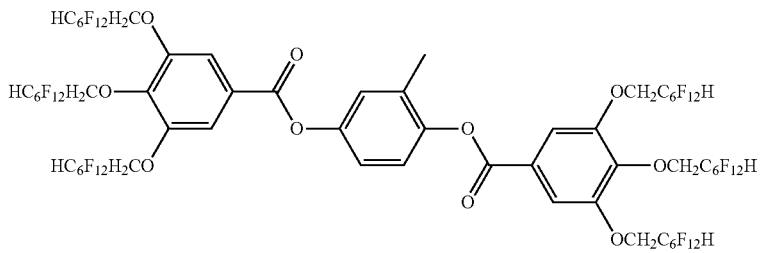
(45)
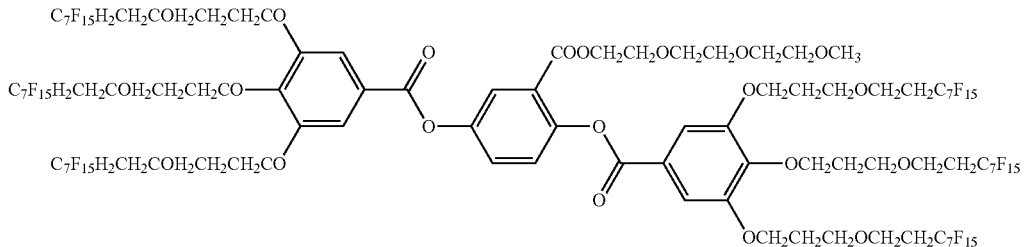
(46)
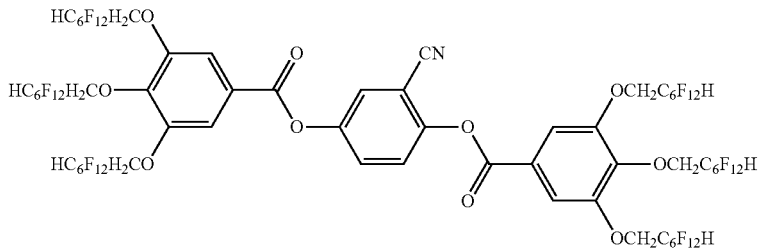

-continued
(47)
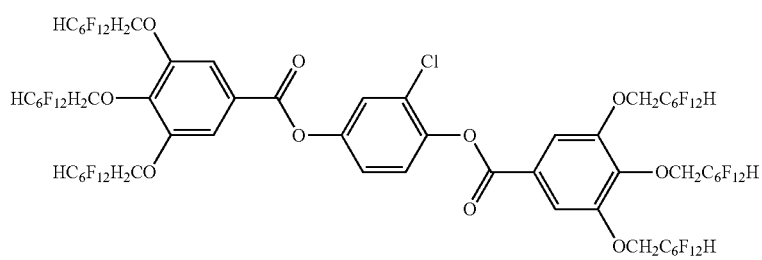
(48)
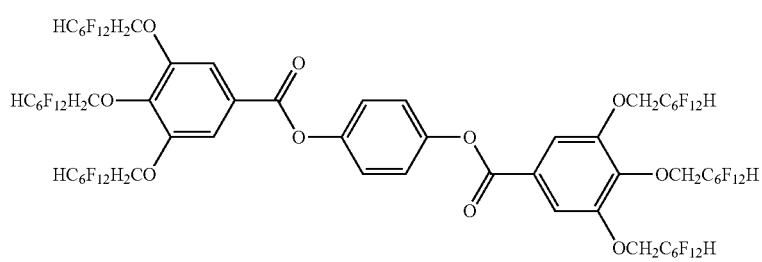
(49)
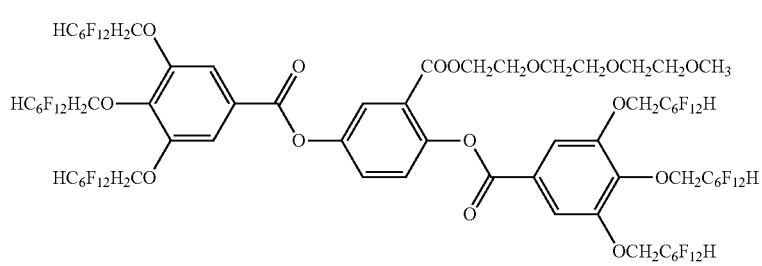
(50)
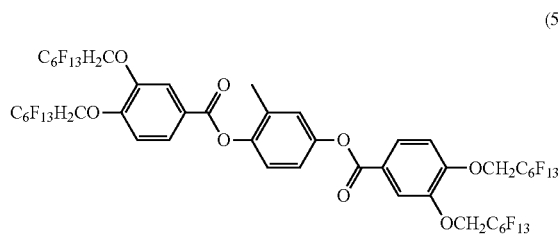
(51)
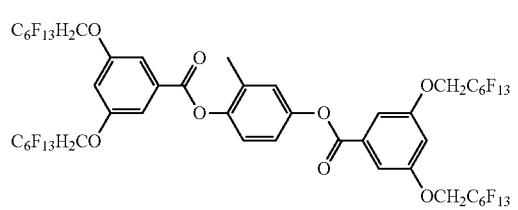
(52)
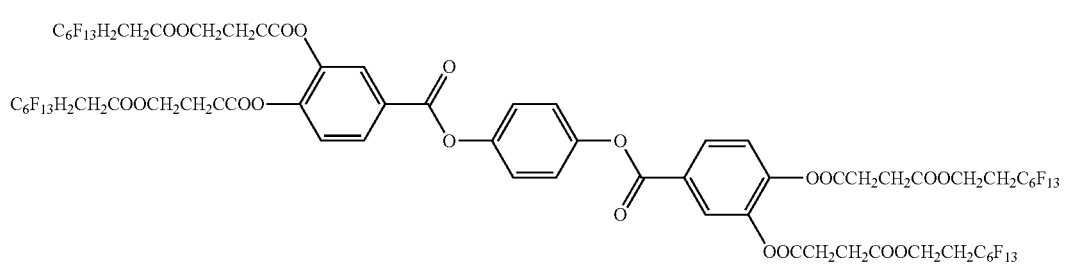
(53)
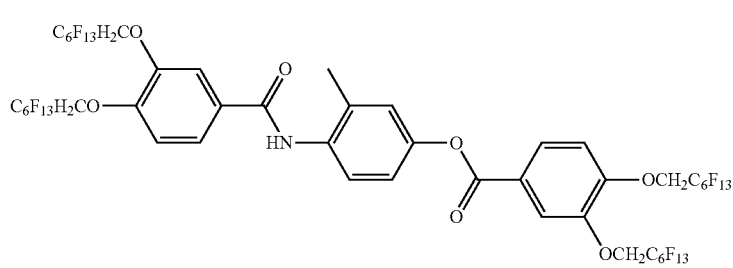

-continued
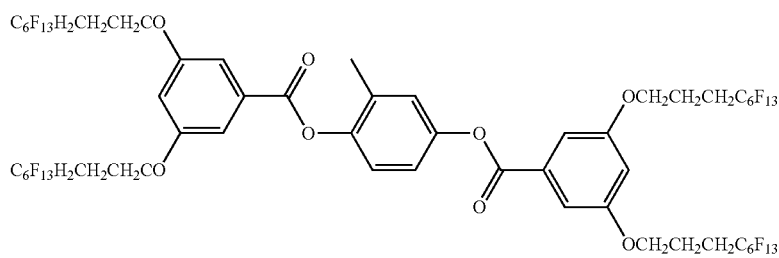
(54)
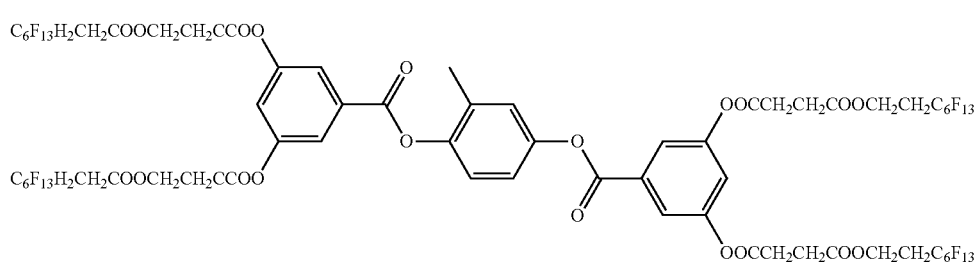
(55)
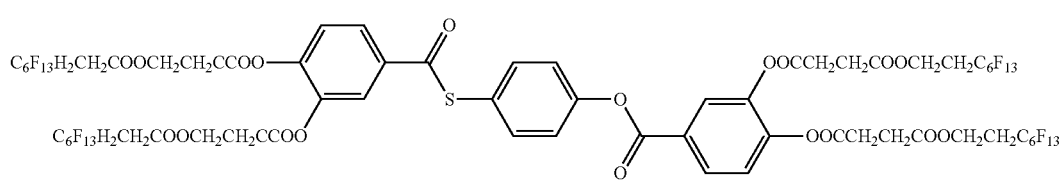
(56)
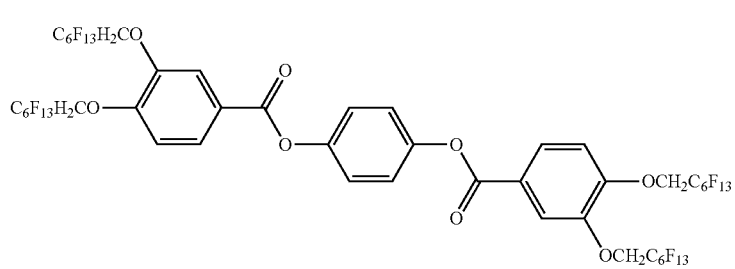
(57)
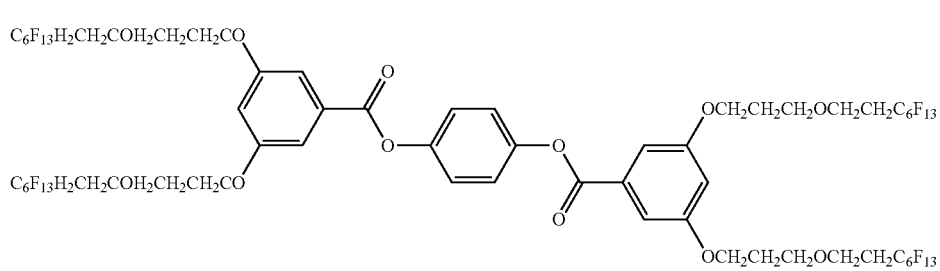
(58)
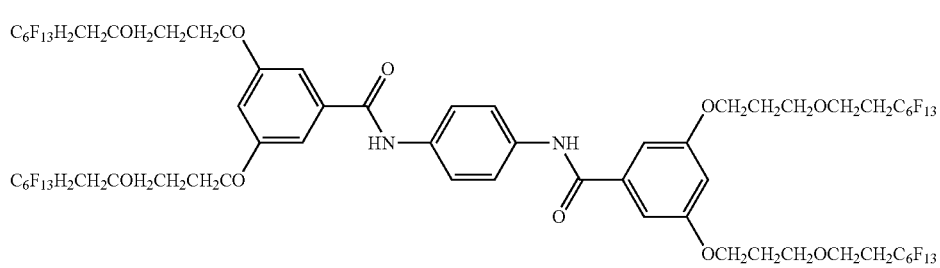
(59)

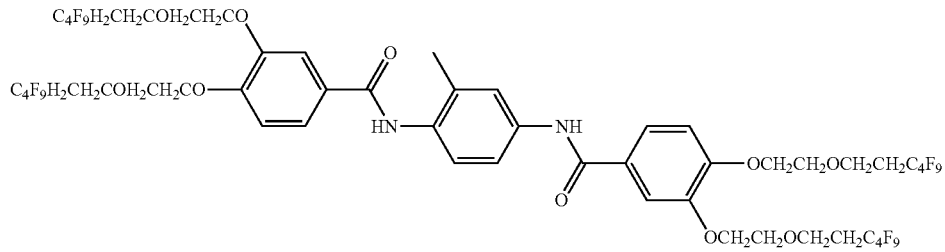
(60)
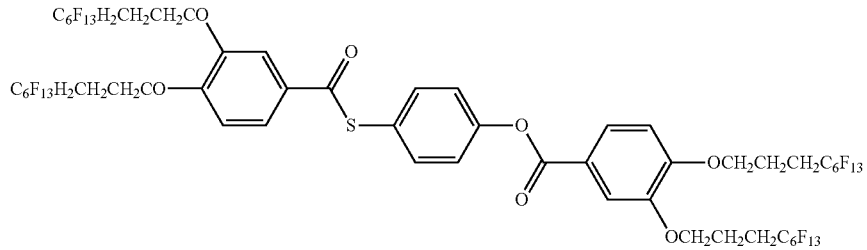
(61)
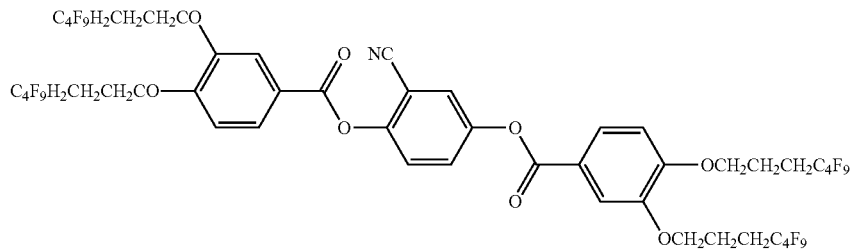
(62)
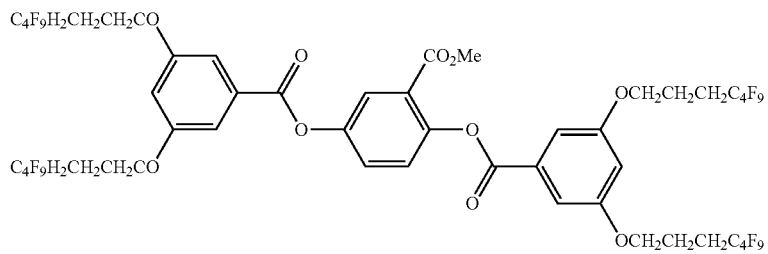
(63)
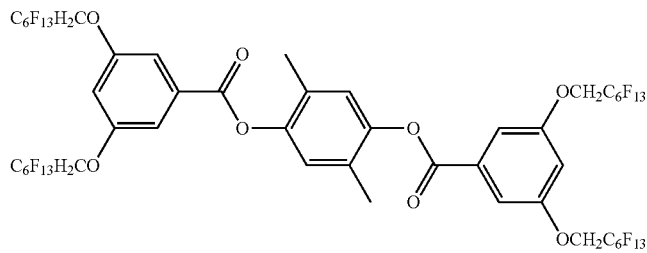
(64)
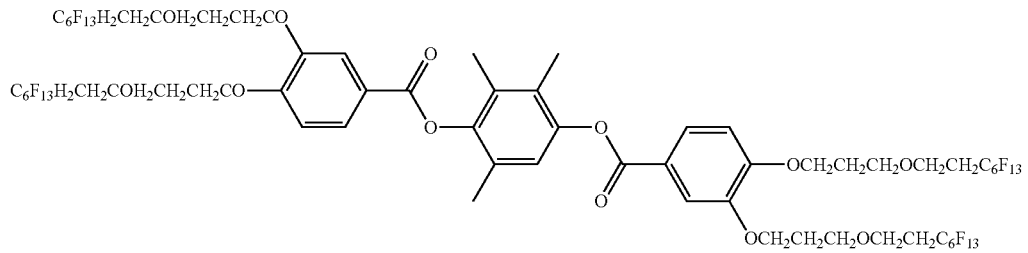
(65)

(66)
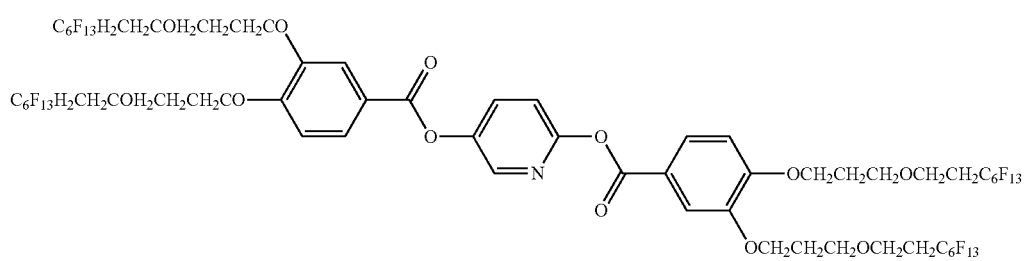
(67)
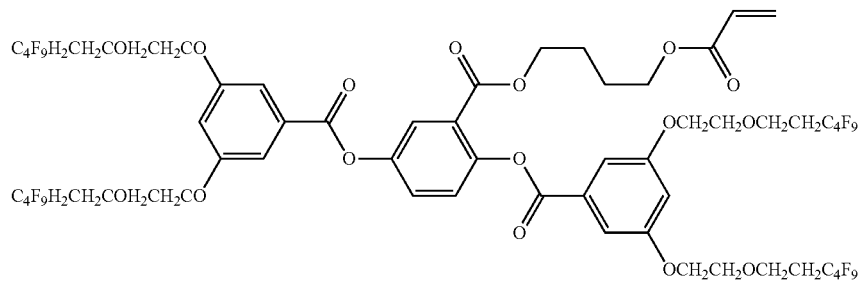
(68)
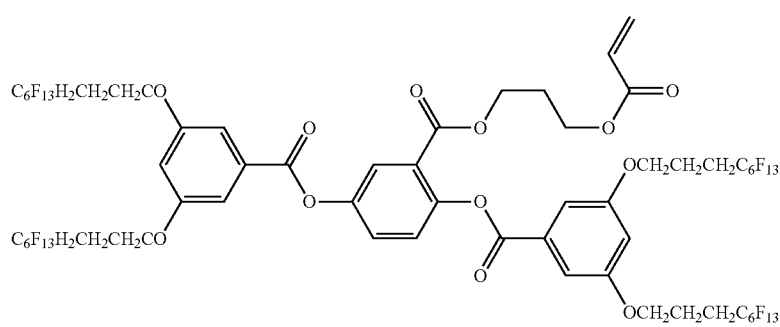
(69)
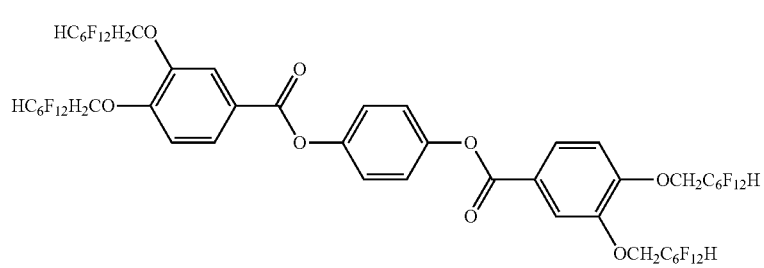
(70)
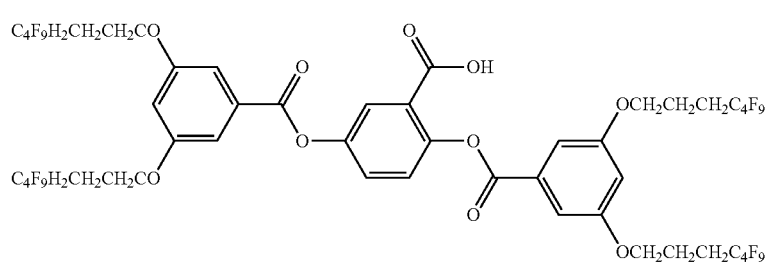
(74)
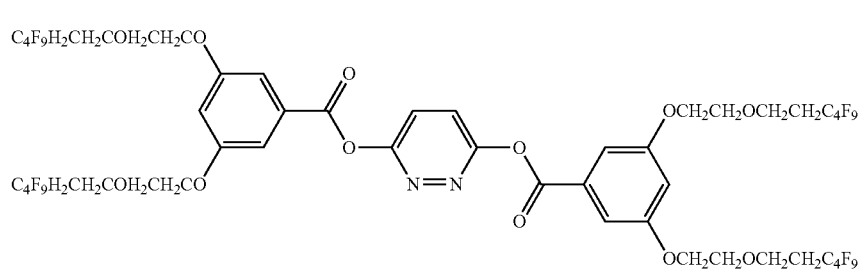

-continued

(75)
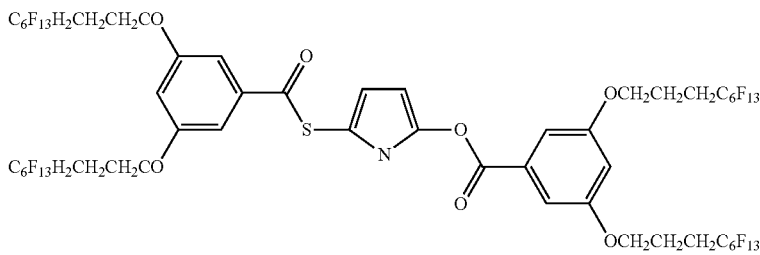

(76)
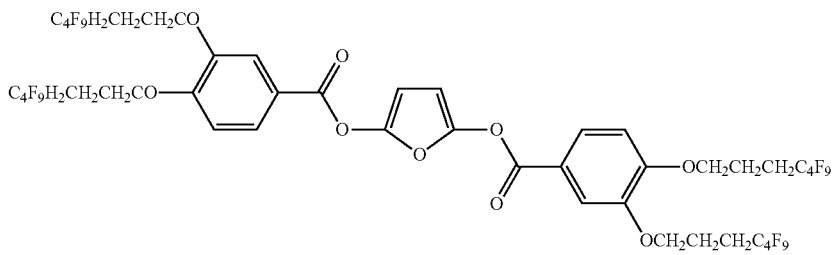

(77)
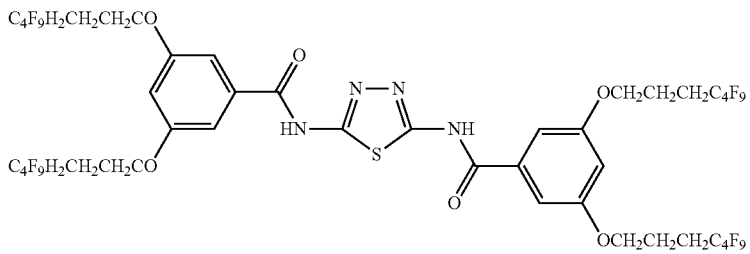

The compounds represented by formula (I) may be synthesized by appropriately selecting and combining the synthesis methods described in JP-A-2002-129162 and JP-A-2002-97170, and in literatures cited in these publications. Other known synthesis methods also may be used in combination, as required.

[Liquid Crystal Composition]

The liquid crystal composition of the present invention includes a polymerizable liquid crystal molecule, and the compound represented by formula (I). In the liquid crystal composition of the present invention, one or more polymerizable liquid crystal molecules and one or more unpolymerizable liquid crystal molecules may be used in combination. The compound represented by formula (I) may be used in a combination of two or more, or in combination with other compounds. The compound represented by formula (I) is used in preferably 0.01 to 20 mass % of the liquid crystal molecule. The compound represented by formula (I) is used in more preferably 0.1 to 10 mass % of the liquid crystal molecule. The polymerizable liquid crystal molecule is preferably a discotic liquid crystal molecule, or a rod-like liquid crystal molecule.

Discotic liquid crystal molecules are described in various literatures (C. Destrade et al., *Mol. Crysr. Liq. Cryst.*, vol. 71, page 111 (1981); The Chemical Society of Japan, *Kikan Kagaku Sousetsu*, No. 22, Liquid Crystal Chemistry, Chapter 5, Chapter 10, Section 2 (1994); B. Kohne et al., Angew. Chem. Soc. Chem. Comm., page 1794 (1985); and J. Zhang et al., J. Am. Chem. Soc., vol. 116, page 2655 (1994)). Polymerization of discotic liquid crystal molecules is described in JP-A-8-27284. Polymerizing and fixing a discotic liquid crystal molecule requires binding a substituent polymerizable group to the discotic core of the discotic liquid crystal molecule. However, directly binding a polymerizable group to the discotic core makes it difficult to maintain the alignment state in a polymerization reaction. This is counteracted by introducing a linking group between the discotic core and the polymerizable group. It is accordingly preferable that the discotic liquid crystal molecule having a polymerizable group be a compound represented by the following formula.

$$D(-L-Q)_d$$

In the formula, D is the discotic core; L is a divalent linking group; Q is a polymerizable group; and d is an integer of 4 to 12. Specific examples of the discotic core (D) in the formula are given below. In the following specific examples, LQ (or QL) means a combination of a divalent linking group (L) and a polymerizable group (Q). Triphenylene (D4) is particularly preferred in the following specific examples.

(D1)
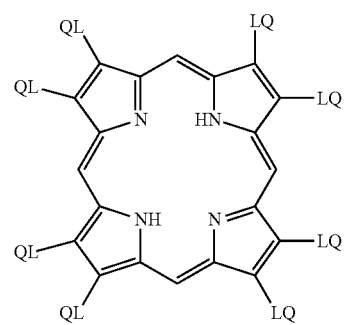

-continued
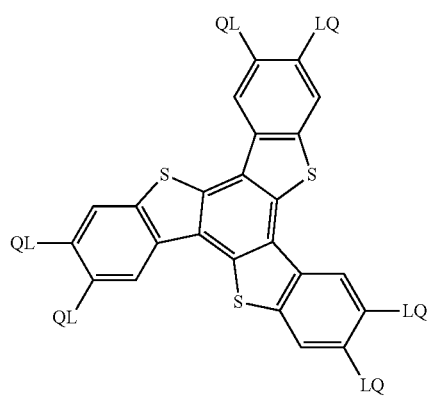
(D2)
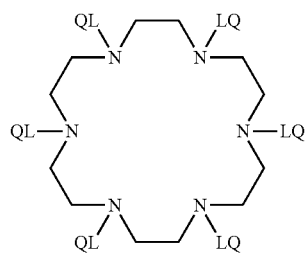
(D3)
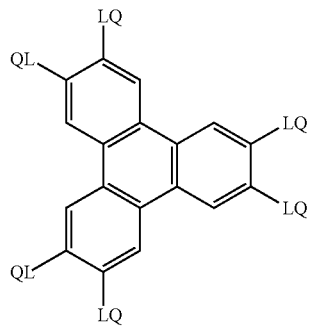
(D4)
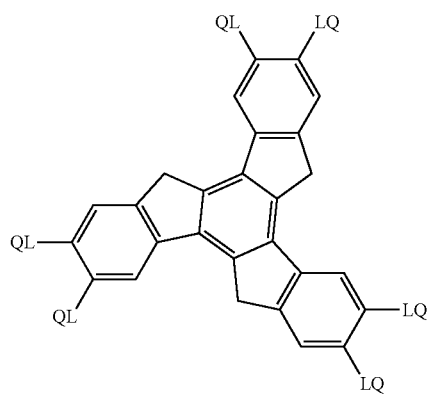
(D5)
-continued
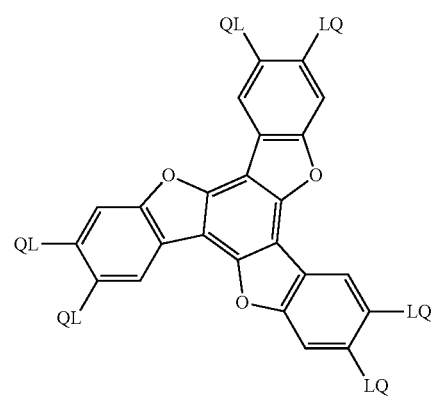
(D6)
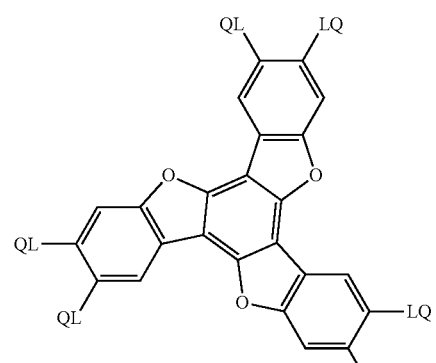
(D7)
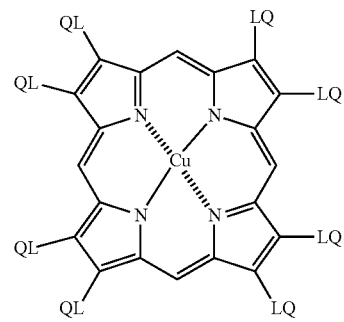
(D8)
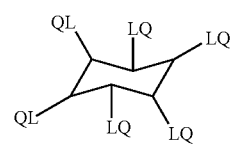
(D9)
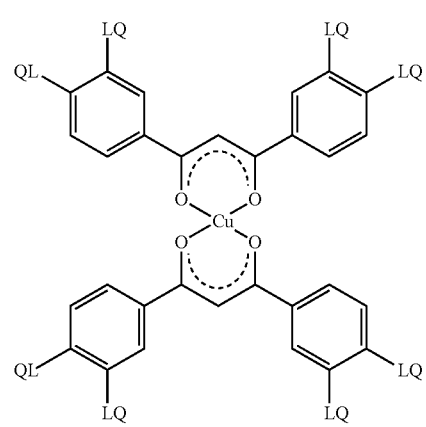
(D10)
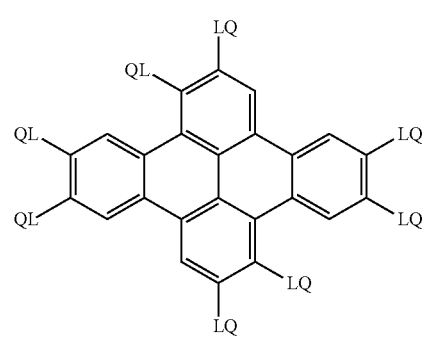

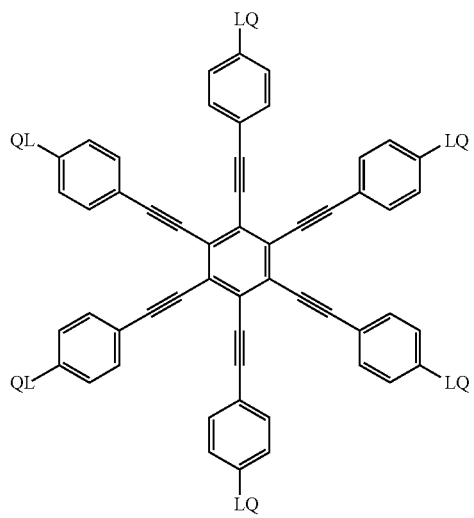

(D11)

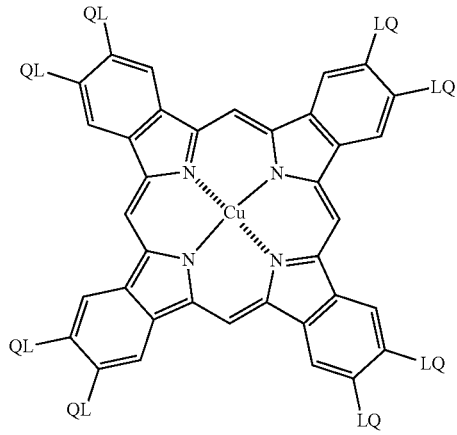

(D14)

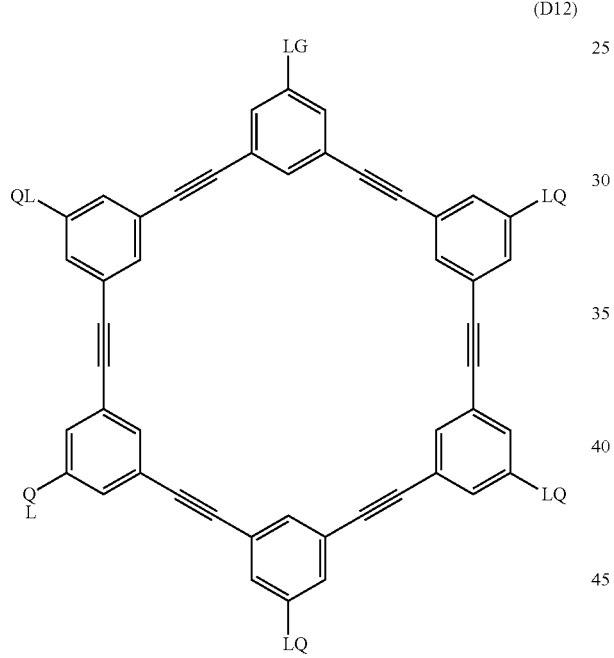

(D12)

(D13)

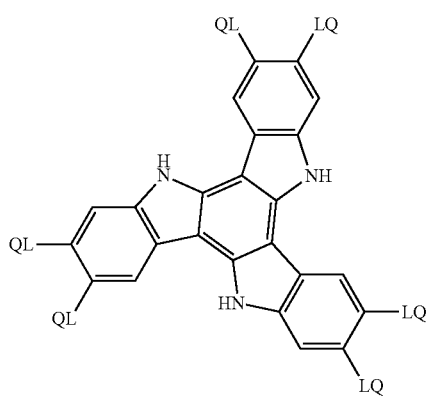

(D15)

Paragraphs [0161] to [0171] of JP-A-2002-129162 may be referred to for details and the preferred ranges of the linking group L and the polymerizable group Q.

Preferred for use as the rod-like liquid crystal molecule are, for example, azomethines, azoxys, cyanobiphenyls, cyanophenyl esters, benzoic acid esters, cyclohexane carboxylic acid phenyl esters, cyanophenyl cyclohexanes, cyano-substituted phenylpyrimidines, alkoxy-substituted phenylpyrimidines, phenyldioxanes, tolans, and alkenylcyclohexylbenzonitriles.

The birefringence of the rod-like liquid crystal molecule is preferably 0.001 to 0.7. Paragraph [0169] of JP-A-2002-129162 may be referred to for specific examples of the polymerizable group. The rod-like liquid crystal molecule preferably has a substantially symmetrical molecular structure with respect to the short axis direction. It is therefore preferable that the molecule has polymerizable groups at the both ends of the rod-like molecular structure. Specific examples of the rod-like liquid crystal molecule are given below.

(N1) 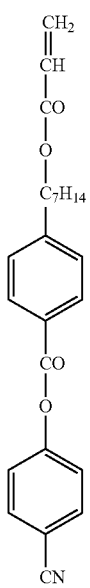
(N2) 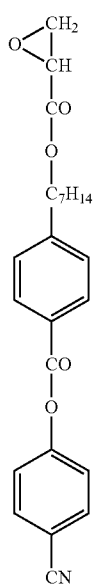
(N3) 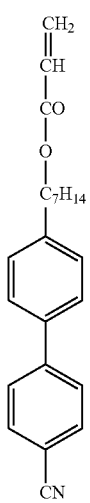
(N4) 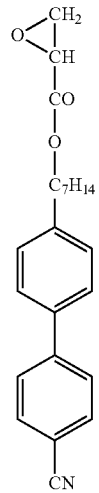
(N5) 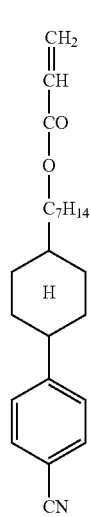
(N6) 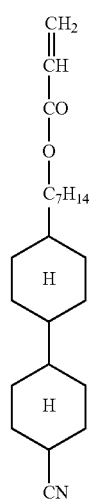

(N7)
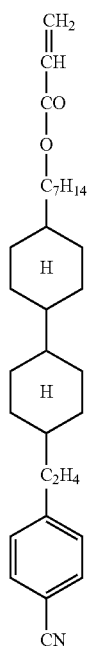
(N8)
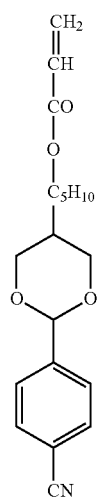
(N9)
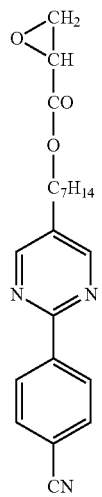
(N10)
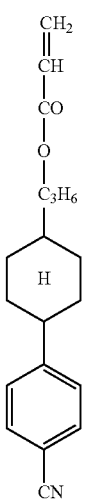
(N11)
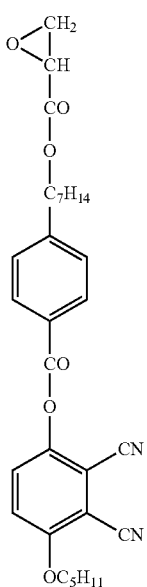
(N12)

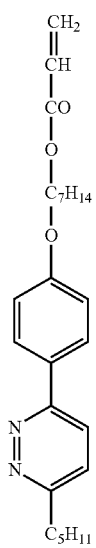 (N13)
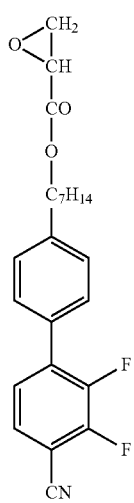 (N14)
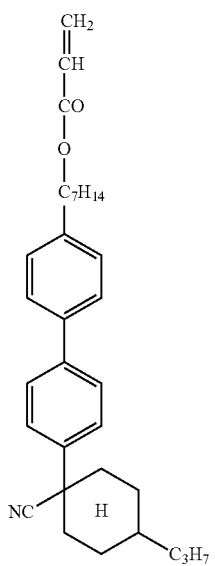 (N15)
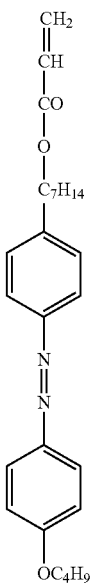 (N16)
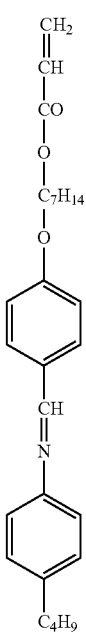 (N17)

(N18)
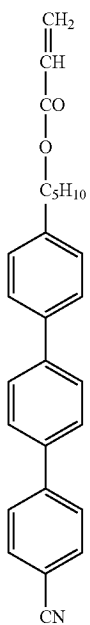
(N19)
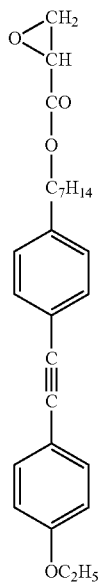
(N20)
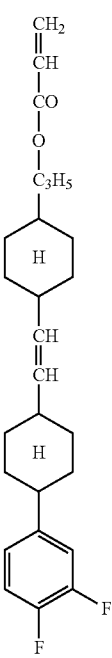
(N21)
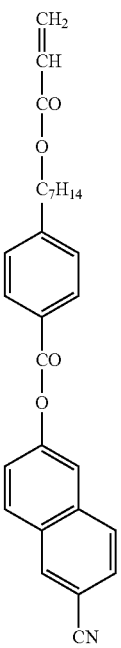

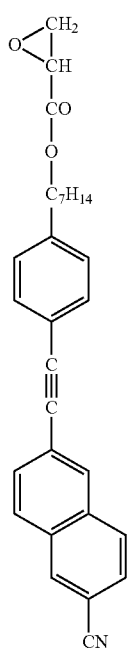 (N22)
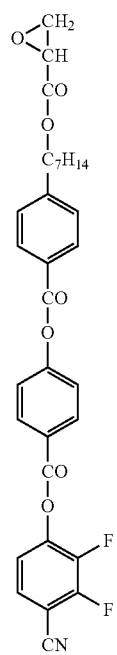 (N24)
 (N23)
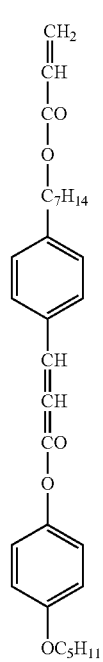 (N25)

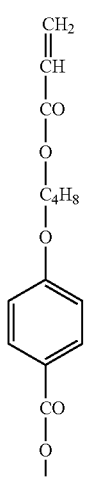
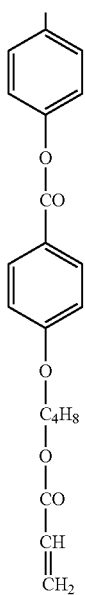
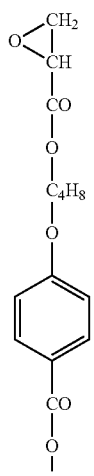
(N26)
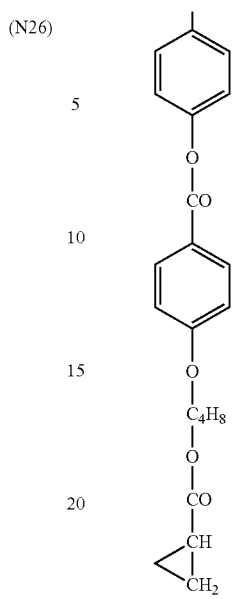
(N27)
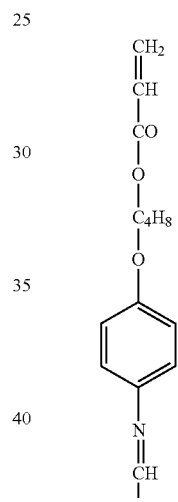
(N28)
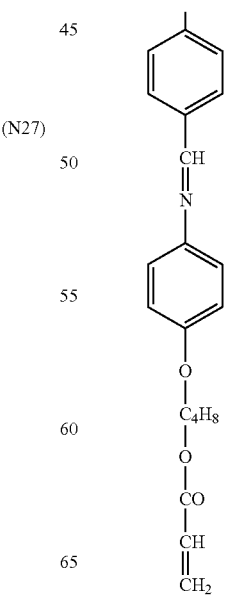

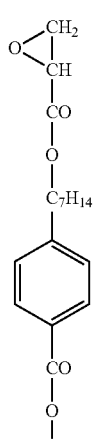
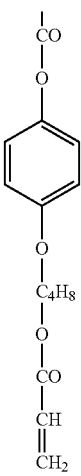
(N29)
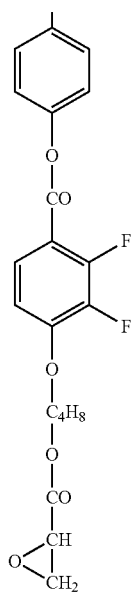
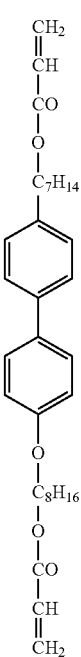
(N31)
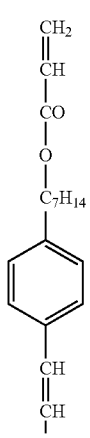
(N30)

(N32)
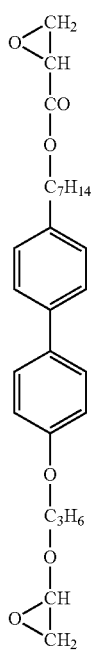
(N33)
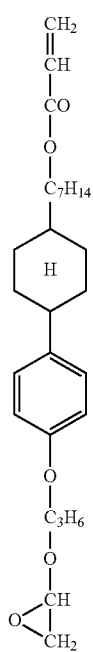
(N34)
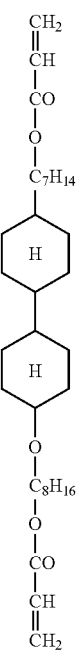
(N35)
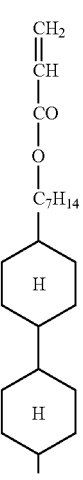
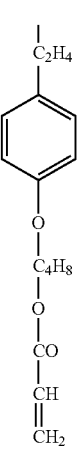

(N36)
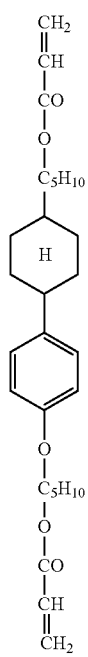
(N37)
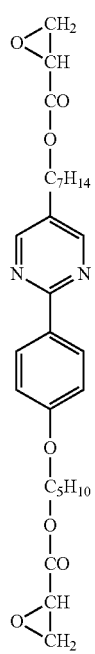
(N38)
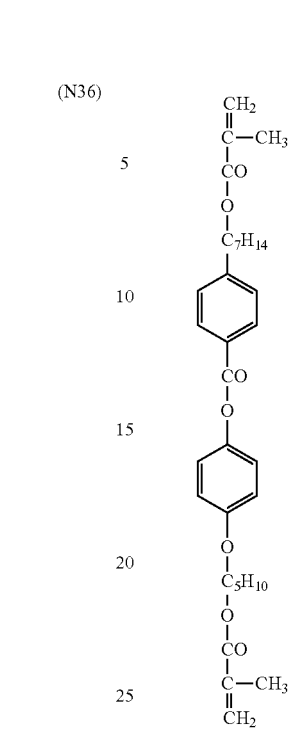
(N39)
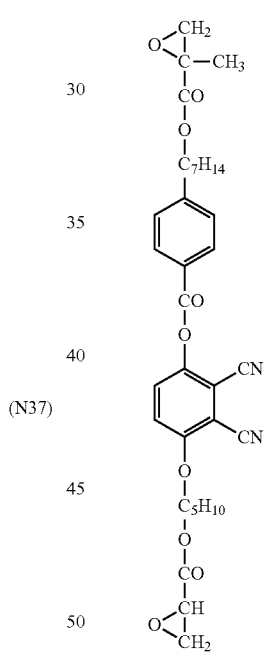
(N40)
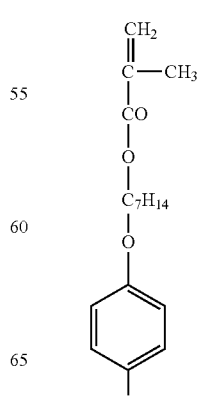

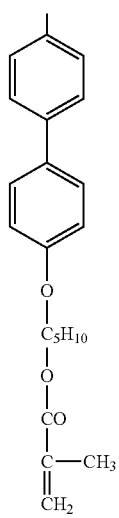
(N41)
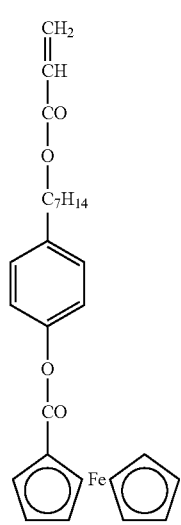
(N42)
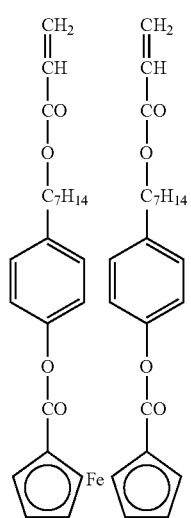
(N43)
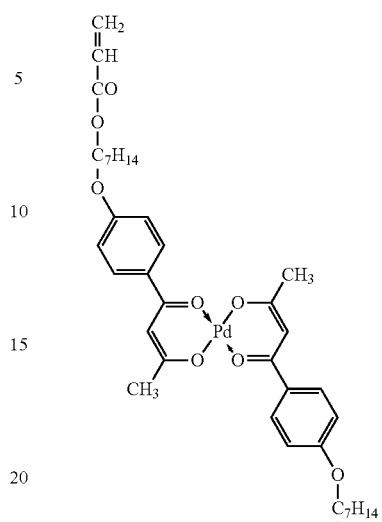
(N44)
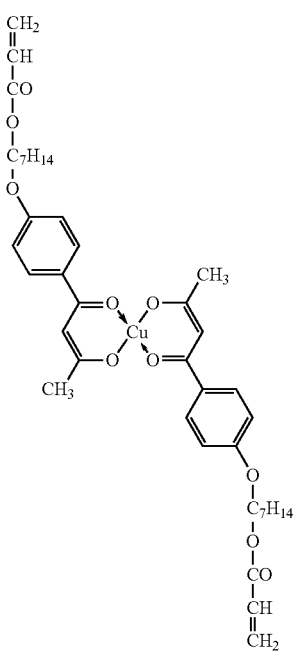

(N45)
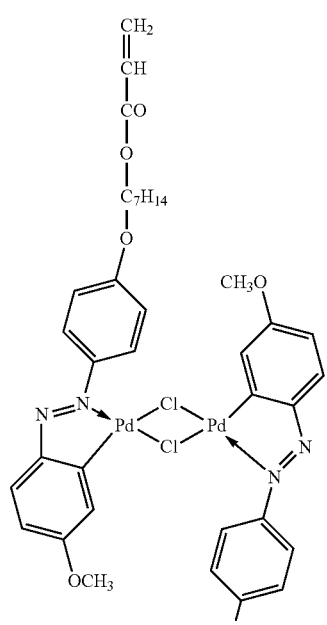
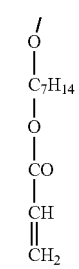
(N46)
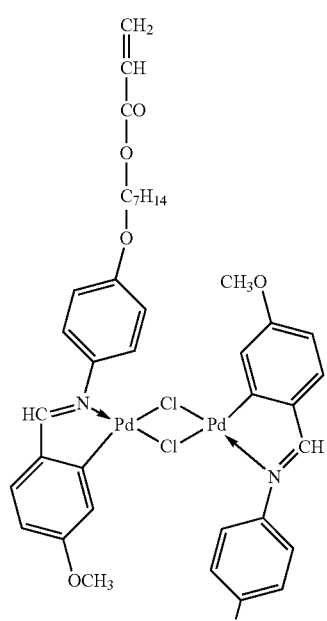
(N47)
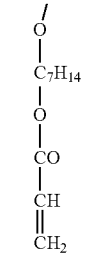
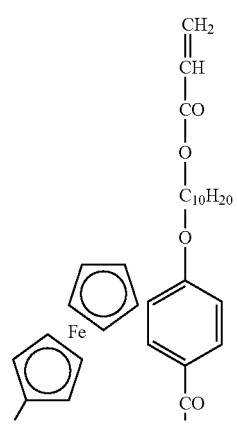
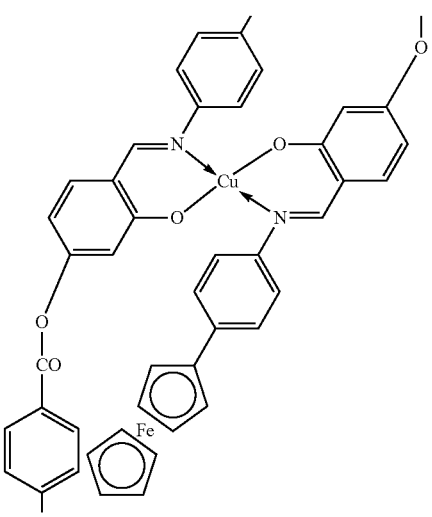

-continued
(N48)
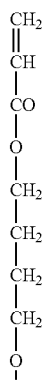
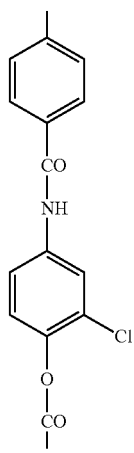
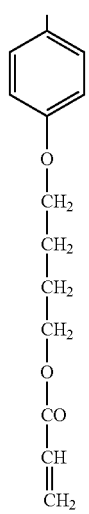
-continued
(N49)
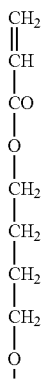
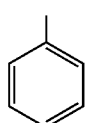
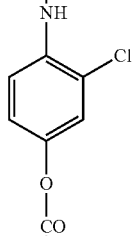
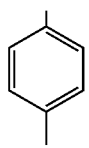
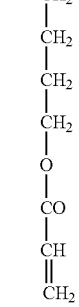
(N50)
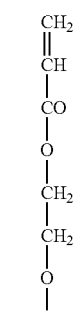

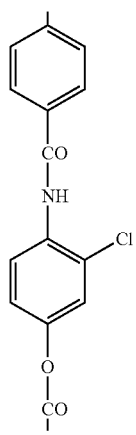
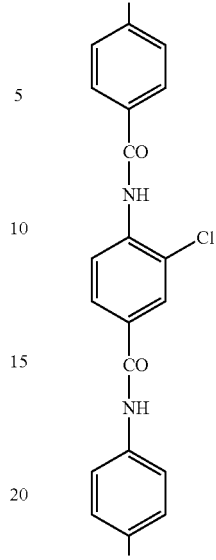
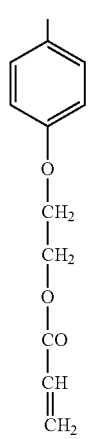
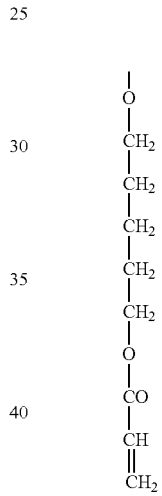
(N51)
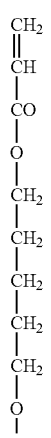
(N52)
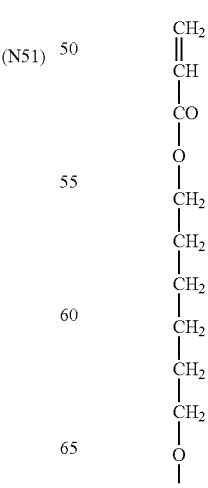

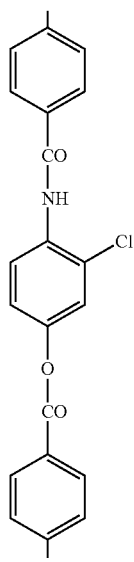
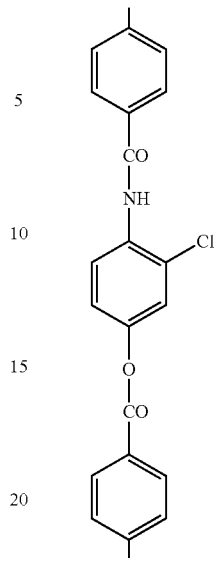
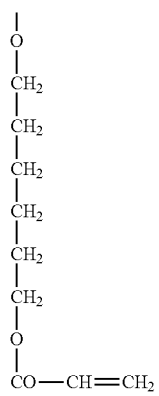
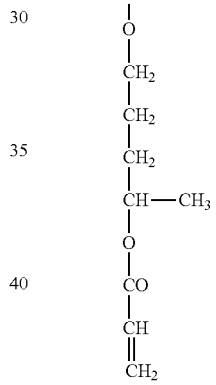
(N53)
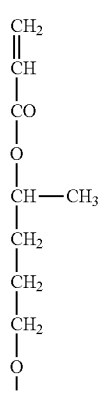
(N54)
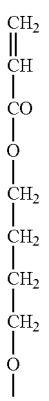

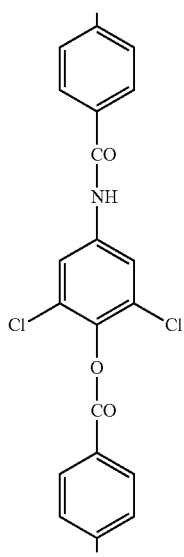
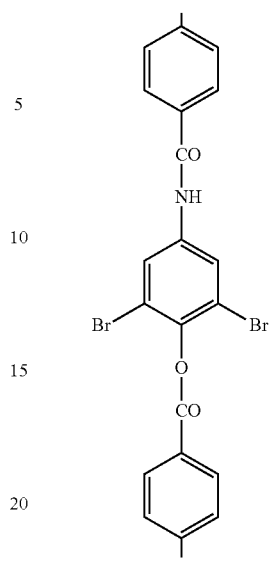
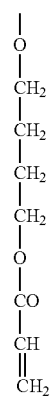
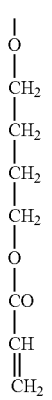
(N55)
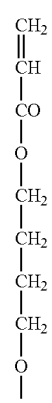
(N56)
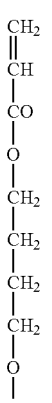

71
-continued
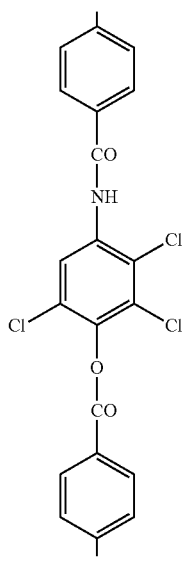
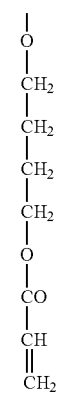
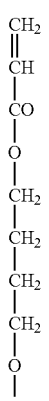
72
-continued
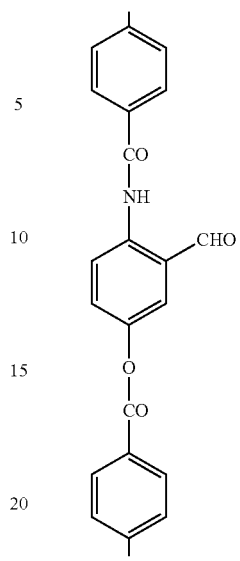
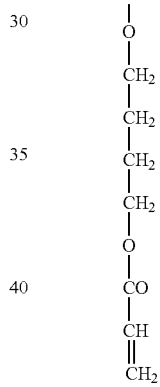
(N57)
(N58)

-continued
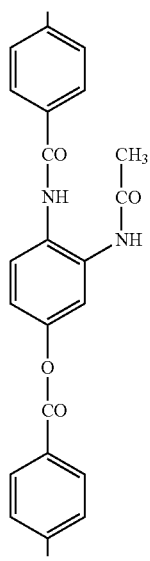
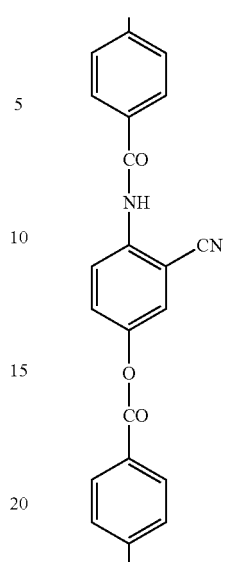
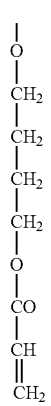
(N59)
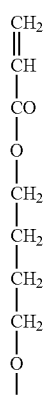
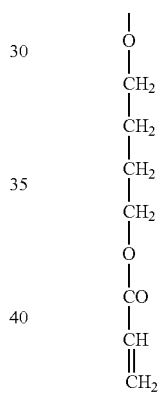
(N60)
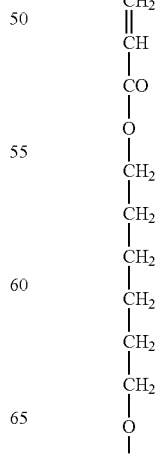

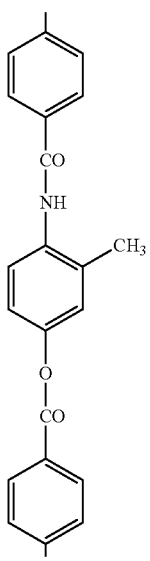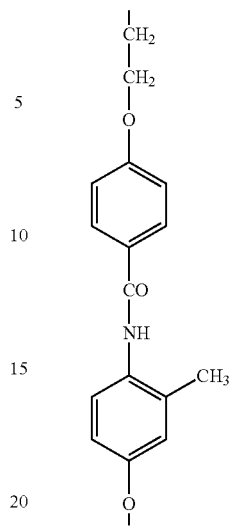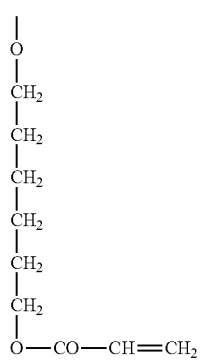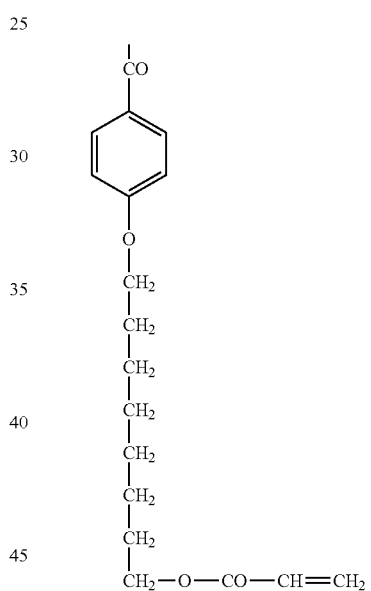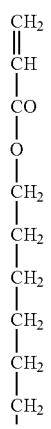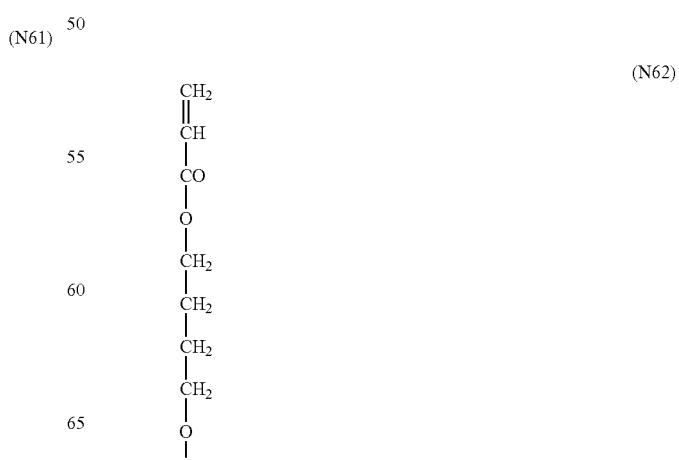

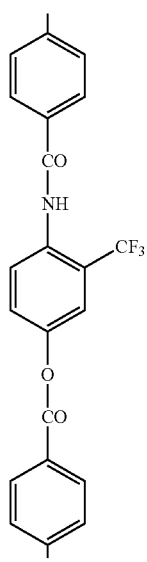
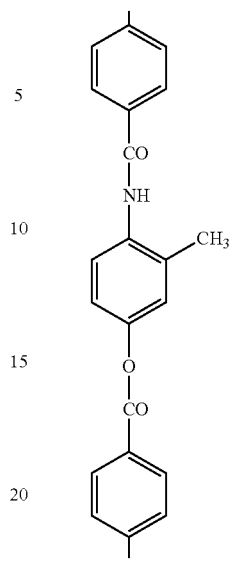
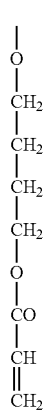
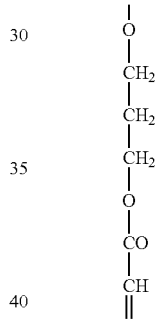
(N63)
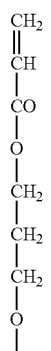
(N64)
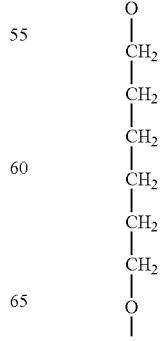

79
-continued
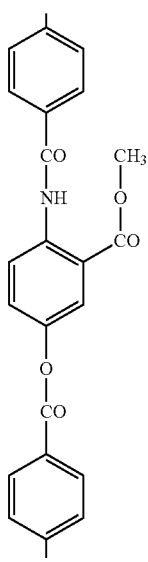
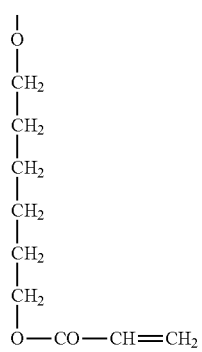
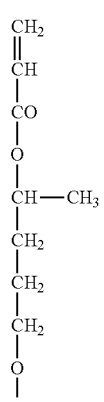
80
-continued
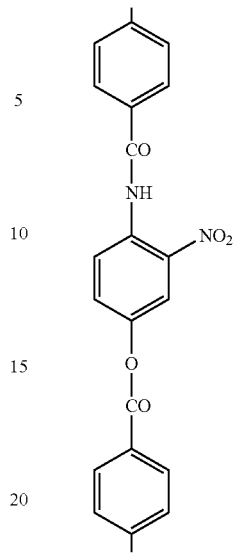
(N65)
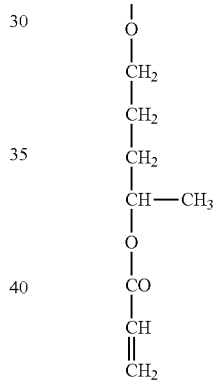
(N66)

81
-continued
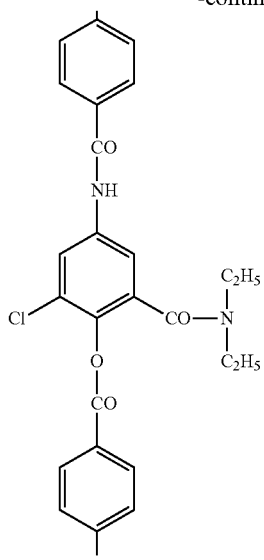
82
-continued
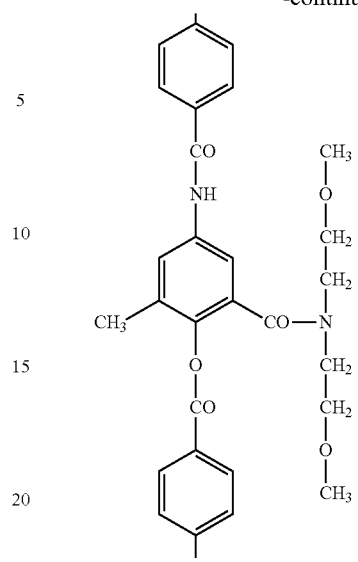
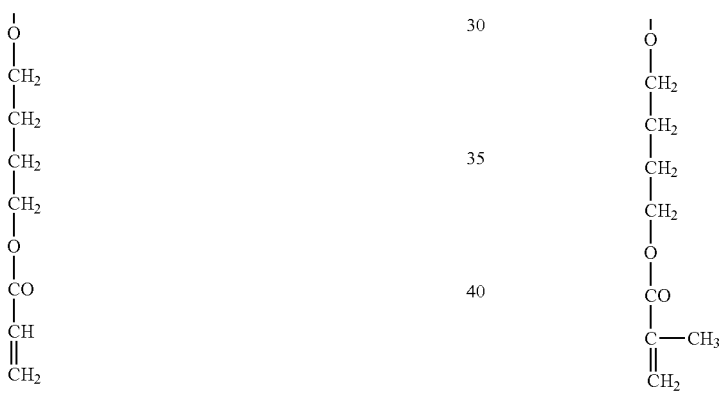
(N67)
(N68)
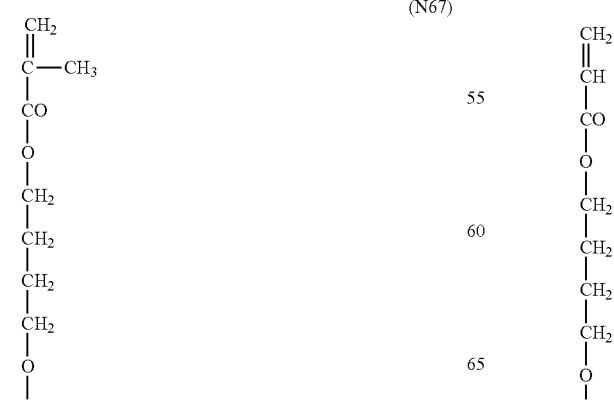

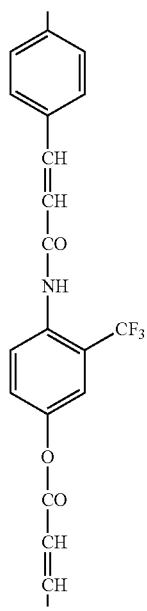
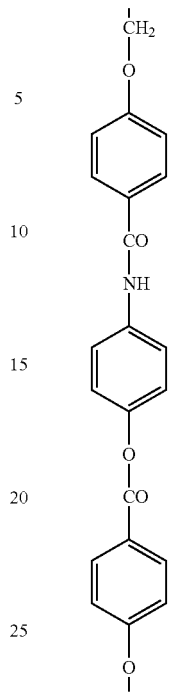
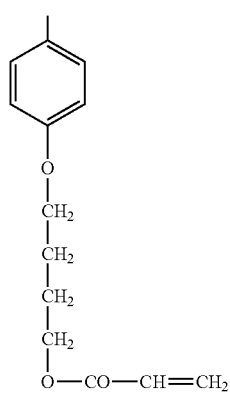
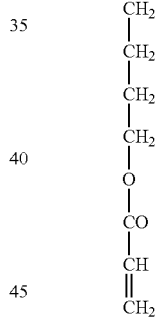
(N69)
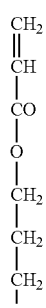
(N70)
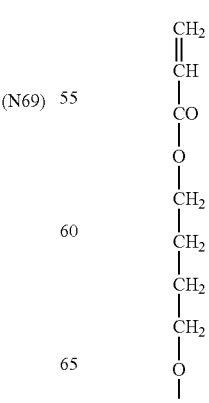

85
-continued
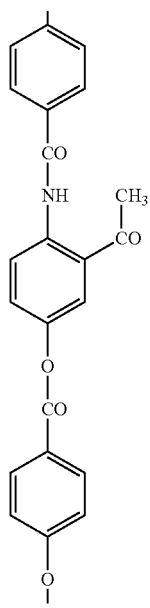
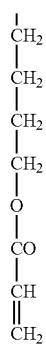
(N71)
86
-continued
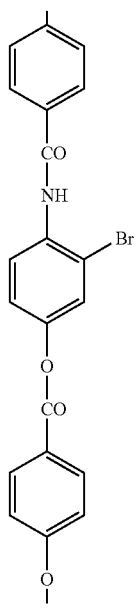
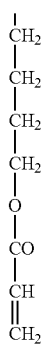
(N72)

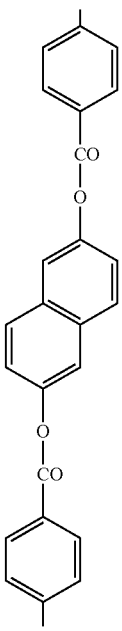

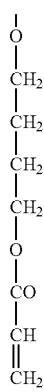

(N73)

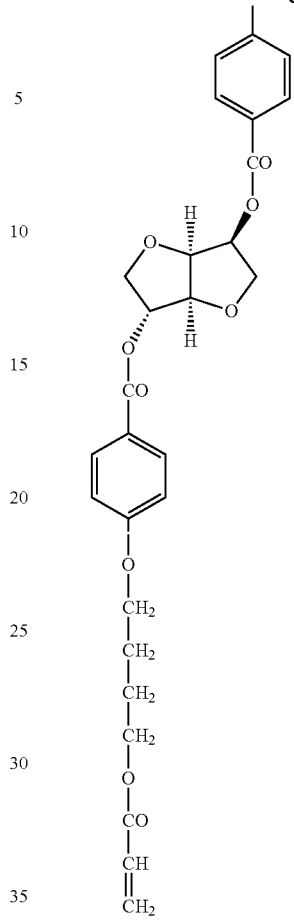

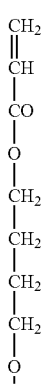

The liquid crystal composition may include a solvent, an asymmetric carbon atom-containing compound, a polymerization initiator (described later), and other additives (for example, cellulose ester), as required, in addition to the polymerizable liquid crystal molecule, and the compound represented by formula (I). An organic solvent is preferably used as the solvent of the liquid crystal composition. Examples of the organic solvent include amides (for example, N,N-dimethylformamide), sulfoxides (for example, dimethylsulfoxide), hetero ring compounds (for example, pyridine), hydrocarbon (for example, benzene, and hexane), alkyl halides (for example, chloroform, and dichloromethane), esters (for example, methyl acetate, and butyl acetate), ketones (for example, acetone, and methyl ethyl ketone), and ethers (for example, tetrahydrofuran, and 1,2-dimethoxyethane). Alkyl halides, and ketone are preferred. Two or more organic solvents may be used in combination.

[Film]

A film may be formed by depositing a liquid crystal composition containing the compound represented by formula (I), using a method such as coating. Further, an optically anisotropic element may be produced by forming a liquid crystal layer with a liquid crystal composition applied onto an alignment film.

The liquid crystal composition may be applied by using known methods (for example, extrusion coating, direct gravure coating, reverse gravure coating, die coating, and bar coating). Preferably, the liquid crystal molecules are fixed with the maintained alignment state. The liquid crystal molecules are preferably fixed through a polymerization reaction of the polymerizable group (Q) introduced to the liquid crystal molecules. The polymerization reaction includes a thermal polymerization reaction that uses a thermal polymerization initiator, and a photopolymerization reaction that uses a photopolymerization initiator. A photopolymerization reaction is preferred. Examples of the photopolymerization initiator include α-carbonyl compounds (described in the specifications of U.S. Pat. No. 2,367,661, and U.S. Pat. No. 2,367,670), acyloin ethers (described in the specification of U.S. Pat. No. 2,448,828), α-hydrocarbon-substituted aromatic acyloin compounds (described in the specification of U.S. Pat. No. 2,722,512), polynuclear quinone compounds (described in the specifications of U.S. Pat. No. 3,046,127 and U.S. Pat. No. 2,951,758), combinations of triarylimidazole dimer and p-aminophenylketone (described in the specification of U.S. Pat. No. 3,549,367), acridine and phenazine compounds (described in the specifications of JP-A-60-105667 and U.S. Pat. No. 4,239,850), oxadiazole compounds (described in the specification of U.S. Pat. No. 4,212,970), and acylphosphine oxide compounds (described in the specifications of JP-B-63-40799, JP-B-5-29234, JP-A-10-95788, and JP-A-10-29997).

The photopolymerization initiator is used in preferably 0.01 to 20 mass o, more preferably 0.5 to 5 mass % of the solid content of the coating liquid. Preferably, ultraviolet light is used for the polymerizing photoirradiation of the discotic liquid crystal molecules. Irradiation energy is preferably 20 mJ/cm$^2$ to 50 J/cm$^2$, more preferably 100 to 800 mJ/cm$^2$. The photoirradiation may be performed under heated conditions to promote the photopolymerization reaction. The thickness of the liquid crystal layer is preferably 0.1 to 50 μm, more preferably 1 to 30 μm, most preferably 5 to 20 μm. The applied amount of the compound represented by formula (I) in the liquid crystal layer is preferably 0.005 to 0.5 g/m$^2$, more preferably 0.01 to 0.45 g/m$^2$, further preferably 0.02 to 0.4 g/m$^2$, most preferably 0.03 to 0.35 g/m$^2$.

[Alignment Film]

The alignment film may be provided by using various means, including rubbing of an organic compound (preferably, a polymer), oblique vapor deposition of an inorganic compound, formation of a layer with microgrooves, and accumulation of an organic compound (for example, ω-tricosanoic acid, dioctadecyl methyl ammonium chloride, and methyl stearate) using the Langmuir-Blodgett technique (LB film). Alignment films that develop an alignment function under an applied electric field, an applied magnetic field, or photoirradiation are also known. An alignment film formed by rubbing a polymer is particularly preferable. Rubbing is performed by rubbing a polymer layer surface with a paper or a fabric in certain directions several times. The type of the polymer used for the alignment film is decided according to the alignment (particularly, the average tilt angle) of the liquid crystal molecules. A polymer (common alignment film polymer) that does not lower the surface energy of the alignment film is used to horizontally (average tilt angle: 0 to 50°) align the liquid crystal molecules, whereas a polymer that lowers the surface energy of the alignment film is used to vertically (average tilt angle: 50 to 90°) align the liquid crystal molecules. In order to lower the surface energy of an alignment film, preferably, a hydrocarbon group having 10 to 100 carbon atoms is introduced to the polymer side chain.

Specific polymers are described in literatures dealing with optical compensation sheets that use various liquid crystal molecules for different display modes. The thickness of the alignment film is preferably 0.01 to 5 μm, more preferably 0.05 to 1 μm. A liquid crystal layer may be transferred onto a transparent support after aligning the liquid crystal molecules of an optically anisotropic layer with an alignment film. The liquid crystal molecules fixed in the alignment state can remain aligned without the alignment film. Rubbing is not required, and the alignment film is unnecessary when the average tilt angle is less than 5°. However, an alignment film (JP-A-9-152509) that forms a chemical bond with the liquid crystal molecules at the interface may be used to improve the adhesion between the liquid crystal molecules and the transparent support. Rubbing may be omitted when such an alignment film is used to improve adhesion. When two liquid crystal layers are provided on the same side of the transparent support, the liquid crystal layer formed on the transparent support may serve as an alignment film for the overlying liquid crystal layer.

[Transparent Support]

The film of the present invention, and an optically anisotropic element having the film of the present invention may have a transparent support. The transparent support is a glass plate, or a polymer film, preferably a polymer film. The support being transparent means an optical transmittance of 80% or more. The transparent support is typically an optically isotropic polymer film. Specifically, by "optically isotropic", it means an in-plane retardation (Re) of preferably less than 10 nm, more preferably less than 5 nm. The optically isotropic transparent support has a thicknesswise retardation (Rth) of preferably less than 10 nm, more preferably less than 5 nm. The in-plane retardation (Re) and the thicknesswise retardation (Rth) of the transparent support are defined by the following equations.

$$Re=(nx-ny)\times d$$

$$Rth=[\{(nx+ny)/2\}-nz]\times d$$

In the formulae, nx and ny are the in-plane refractive indices of the transparent support, nz is the thicknesswise refractive index of the transparent support, and d is the thickness of the transparent support.

The transparent support may be an optically anisotropic polymer film. In this case, the transparent support preferably has an optically uniaxial property, or an optically biaxial property. In the case of an optically uniaxial support, the support may be optically positive (the refractive index of the optical axis direction being greater than the refractive index of the direction perpendicular to the optical axis), or negative (the refractive index of the optical axis direction being smaller than the refractive index of the direction perpendicular to the optical axis). In the case of an optically biaxial support, the refractive indices nx, ny, and nz in the foregoing formulae all take different values (nx≠ny≠nz). The in-plane retardation (Re) of the optically anisotropic transparent support is preferably 10 to 1,000 nm, more preferably 15 to 300 nm, most preferably 20 to 200 nm. The thicknesswise retardation (Rth) of the optically anisotropic transparent support is preferably 10 to 1,000 nm, more preferably 15 to 300 nm, further preferably 20 to 200 nm.

The material used to form the transparent support depends on whether the transparent support is provided as an optically isotropic support or an optically anisotropic support. In the case of an optically isotropic support, glass or cellulose ester is typically used. In the case of an optically anisotropic support, synthetic polymers (for example, polycarbonate, polysulfone, polyethersulfone, polyacrylate, polymethacrylate, norbornene resin) are used. An optically anisotropic (high retardation) cellulose ester film also may be produced by using the film producing methods described in the specification of European Patent No. 0911656A2, specifically by (1) using a retardation increasing agent, (2) lowering the degree of acetification of cellulose acetate, or (3) using a cooling dissolution method. The transparent support formed of a polymer film is preferably formed by using a solvent casting method.

Preferably, the optically anisotropic transparent support is obtained by drawing a polymer film. The optically uniaxial support may be produced by using a common uniaxial drawing process or a biaxial drawing process. The optically biaxial support is produced preferably through an unbalanced biaxial drawing process. In the unbalanced biaxial drawing, a polymer film is drawn in a certain direction at a certain rate (for example, 3 to 100%, preferably 5 to 30%), and in a direction perpendicular to this direction at a higher rate (for example, 6 to 200%, preferably 10 to 900). The drawing may be simultaneously performed in two directions. Preferably, the drawing direction (the direction with a higher drawing rate in the case of unbalanced biaxial drawing) and the in-plane slow axis of the drawn film direct in substantially the same direction. The angle between the drawing direction and the slow axis is preferably less than 10°, more preferably less than 5°, further preferably less than 3°.

The thickness of the transparent support is preferably 10 to 500 μm, more preferably 50 to 200 μm. The transparent support may be subjected to a surface treatment (for example, glow discharge process, corona discharge process, ultraviolet (UV) treatment, and flame treatment) to improve the adhesion between the transparent support and the overlying layer (adhesive layer, alignment film, or optically anisotropic layer). A ultraviolet absorber may be added to the transparent support. An adhesive layer (primer layer) may be provided on the transparent support. The adhesive layer is described in JP-A-7-333433. The thickness of the adhesive layer is preferably 0.1 to 2 μm, more preferably 0.2 to 1 μm.

EXAMPLES

The features of the present invention are described below in greater detail using Examples and Comparative Examples. Materials, amounts, proportions, and the contents and the procedures of the processes used in the following Examples may be appropriately varied, provided that such changes do not depart from the gist of the present invention. Accordingly, the scope of the present invention should not be narrowly interpreted within the limits of the concrete examples described below.

Synthesis Example 1

Compound (1) was synthesized by using the following route.

(1-1) Synthesis of Ester (1b)

Alcohol (1a; 70.0 g, 200 mmol) was added to 100 ml of methylene chloride, and triethylamine (29.2 ml, 210 mmol) was added to the mixture. The solution was dipped in ice-cold water, and a trifluoromethanesulfonic acid anhydride (35.3 ml, 210 mmol) was dropped to make the inner temperature 20° C. or less. The mixture was then allowed to react under ice-cooled condition for 1 hour. The reaction mixture was subjected to a separation procedure, and the organic layer was concentrated with an evaporator. The resulting liquid was distilled under reduced pressure to give a corresponding trifluoromethanesulfonic acid ester (1b; 85.0 g, yield 880).

$^1$H NMR (300 MHz, CDCl$_3$) δ 4.8 (t, 2H)

(1-2) Synthesis of Ester (1c)

Ester (1b; 22.4 g, 46.5 mmol), and methyl gallate ester (2.8 g, 15 mmol) were reacted in DMAc (15 ml) at 90° C. for 2 hours in the presence of potassium carbonate (6.4 g, 46.5 mmol). This was followed by separation and column purification to give an ester (1c; 15.0 g, 85%).

$^1$H NMR (300 MHz, CDCl$_3$) δ 3.9 (s, 3H), 4.4-4.6 (m, 6H), 7.4 (s, 2H)

(1-3) Synthesis of Carboxylic Acid (1d)

Ester (1c; 11.8 g, 10 mmol) was added to ethanol (30 ml) and water (3 ml). Potassium hydroxide (0.84 g, 15 mmol) was added to the solution, and the mixture was heated under reflux for 2 hours. The reaction mixture was dropped into a hydrochloric acid aqueous solution to precipitate a solid. Carboxylic acid (1d; 9.8 g, 84%) was obtained after suction filtration.

(1-4) Synthesis of Compound (1)

Carboxylic acid (1d; 2.3 g, 2.0 mmol) was reacted with thionyl chloride (0.22 ml, 3.0 mmol) in toluene (10 ml) and a catalytic amount of DMF to produce an acid chloride. After removing the excess thionyl chloride and toluene, a THF (5 ml) and a catalytic amount of DMAP were added to the system. THF (5 ml), and methylhydroquinone (124 mg, 1.0 mmol) dissolved in diisopropylethylamine (0.37 ml) were dropped into the mixture, and a reaction was allowed at room temperature for 3 hours. This was followed by separation, concentration with an evaporator, column purification, and recrystallization from methanol to give compound (1) (0.79 g, yield 33%).

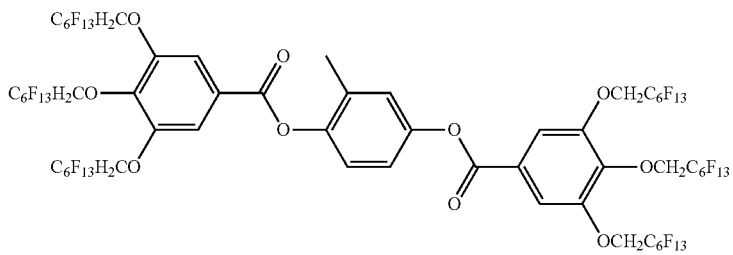

$^1$H NMR (400 MHz, CDCl$_3$) δ 2.3 (s, 3H), 4.5-4.7 (m, 12H), 7.0-7.2 (s×3, 3H), 7.6 (s×2, 4H)

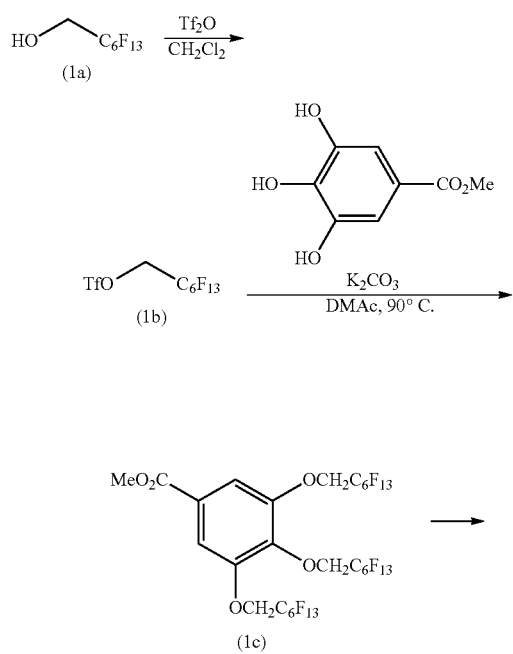
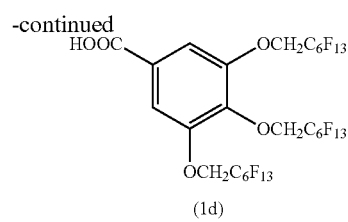
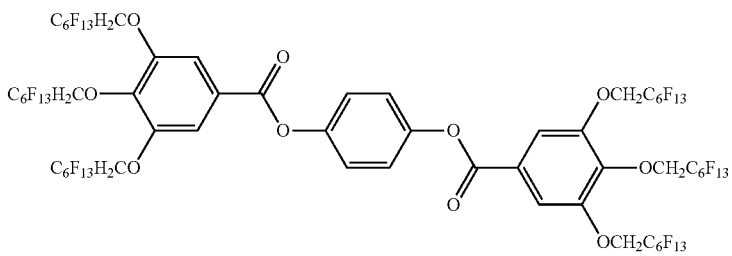
Synthesis Example 2
Synthesis of Compound (8)
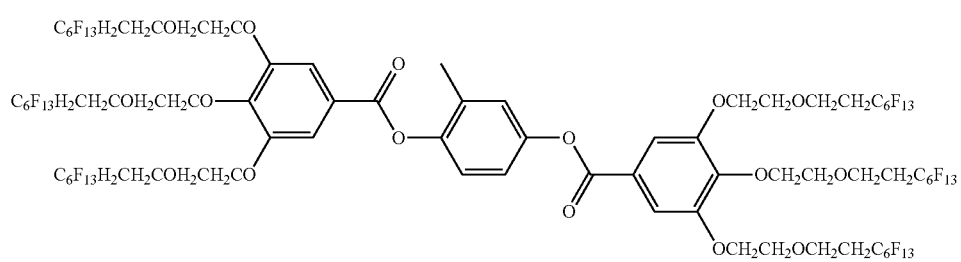
Compound (8) was obtained by using the same procedures used for the synthesis of compound (1), except that hydroquinone was used instead of methylhydroquinone.
$^1$H NMR (400 MHz, CDCl$_3$) δ 4.4-4.7 (m, 12H), 7.3 (s, 4H), 7.6 (s, 4H)
Synthesis Example 3
Synthesis of Compound (2)

Compound (2) was synthesized by using the following route.

(3-1) Synthesis of Tosyl Derivative (3b)

Alcohol (3a; 45.7 ml, 300 mmol) and para-toluenesulfonyl chloride (60.1 g, 315 mmol) were reacted in 120 ml of methylene chloride under ice-cooled condition for 1 hour. The reaction mixture was subjected to a separation procedure, and the organic layer was concentrated with an evaporator to obtain a tosyl ether (3b) as a crude yellow liquid. The product was directly used as raw material in the next step without being purified.

$^1$HNMR (300 MHz, CDCl$_3$) δ 2.4 (s, 3H), 3.6 (d, 2H), 4.2 (d, 2H), 4.4 (s, 2H), 7.1-7.4 (d×3, s×1, 7H), 7.8 (d, 2H)

(3-2) Synthesis of Fluoroalkyl Ether (3c)

Tosyl derivative (3b; 16.2 g, 50 mmol) and 2-(perfluorohexyl)ethanol (12.1 ml, 55 ml) were added to 100 ml of toluene, and a benzyltrimethylammonium hydroxide aqueous solution (105 ml) was added thereto. After heating the mixture to 70° C. and stirring the mixture for 30 min, a potassium hydroxide aqueous solution (3.1 g/water 20 ml) was added. The mixture was heated to 80° C., and a reaction was allowed for 5 hours. After adding ethyl acetate (100 ml) and water (50 ml) for separation, the resulting liquid was concentrated to obtain ether (3c) as a crude product. The product was directly used as raw material in the next step without being purified.

$^1$HNMR (300 MHz, CDCl$_3$) δ 2.5 (m, 2H), 3.8 (d, 2H), 4.0 (d, 2H), 4.4 (s, 2H), 7.1-7.4 (m, 5H)

(3-3) Synthesis of Alcohol (3d)

Ether (3c; 20.0 g, 40 mmol) was reacted with hydrogen in ethyl acetate (40 ml) in the presence of a palladium catalyst (1.2 g, 5% palladium/activated carbon, Degussa type E 101 O/W 5% Pd, Wako). After the reaction, the palladium catalyst was removed by celite filtration, and the resulting liquid was concentrated to obtain alcohol (2e) as a crude product. The product was directly used as raw material in the next step without being purified.

$^1$H NMR (400 MHz, CDCl$_3$) δ 2.4 (m, 2H), 3.6 (d, 2H), 3.7 (d, 2H), 3.8 (d, 2H)

(3-4) Synthesis of Methanesulfonic Acid Ester (3e)

Alcohol (3d; 18.0 g, 45 mmol) was added to 30 ml of ethyl acetate, and the mixture was ice-cooled. Methanesulfonyl chloride (3.8 ml, 49.5 mmol) was then dropped at the maintained temperature of 20° C. or less in the reaction system. Reaction was allowed at room temperature for 3 hours, and the mixture was separated with ethyl acetate and water. The resulting liquid was concentrated to give methanesulfonic acid ester (3e) as a crude product. The product was directly used as raw material in the next step without being purified.

(3-5) Synthesis of Gallic Acid Ester (3f)

Ester (3e; 10.6 g, 21.6 mmol) and methyl gallate ester (1.28 g, 7.0 mmol) were reacted in DMAc (40 ml) at 90° C. in the presence of potassium carbonate (3.0 g, 21.6 mmol). The mixture was subjected to a separation procedure in an ethyl acetate/water system, and the resulting liquid was column purified to obtain an oily gallic acid ester (3f; 8.0 g, 84%).

$^1$H NMR (400 MHz, CDCl$_3$) δ 2.3-2.6 (m, 6H), 3.7-4.0 (m, 15H), 4.2 (m, 6H), 7.4 (s, 2H)

(3-6) Synthesis of Carboxylic Acid (3g)

Ester (3f; 7.8 g, 5.8 mmol) was added to ethanol (40 ml) and water (4 ml). Potassium hydroxide (0.48 g, 8.6 mmol) was added to the solution, and the mixture was heated under reflux for 2 hours. The reaction mixture was separated in an ethyl acetate/water system, and the organic layer was concentrated and solidified to give carboxylic acid (3g; 5.6 g, 72%).

(3-7) Synthesis of Compound (2)

Carboxylic acid (3g; 2.0 g, 1.5 mmol) was reacted with thionyl chloride (0.16 ml, 2.2 mmol) in toluene (10 ml) and a catalytic amount of DMF to produce an acid chloride. After removing the excess thionyl chloride and toluene, THF (5 ml) and a catalytic amount of DMAP were added to the system. THF (5 ml), and methylhydroquinone (93 mg, 0.76 mmol) dissolved in diisopropylethylamine (0.28 ml) were then dropped into the mixture. After a separation procedure with an ethyl acetate/water system, the resulting liquid was concentrated with an evaporator, column purified, and recrystallized in an ethyl acetate/methanol system to give compound (2) (1.5 g, 71%).

$^1$H NMR (300 MHz, CDCl$_3$) δ 2.2 (s, 3H), 2.3-2.5 (m, 12H), 3.7-3.9 (m, 24H), 4.2 (m, 12H), 7.1 (m, 3H), 7.4-7.5 (s×2, 4H)

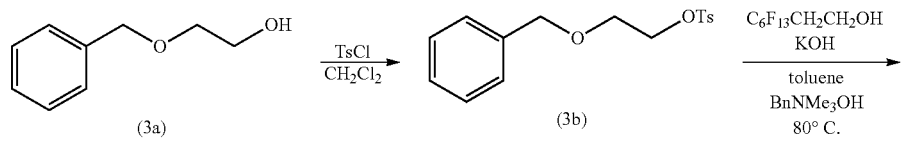

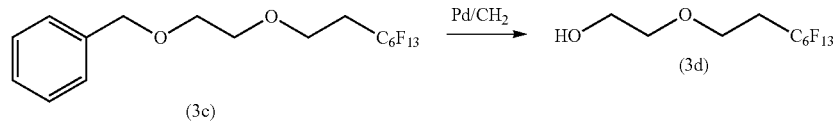

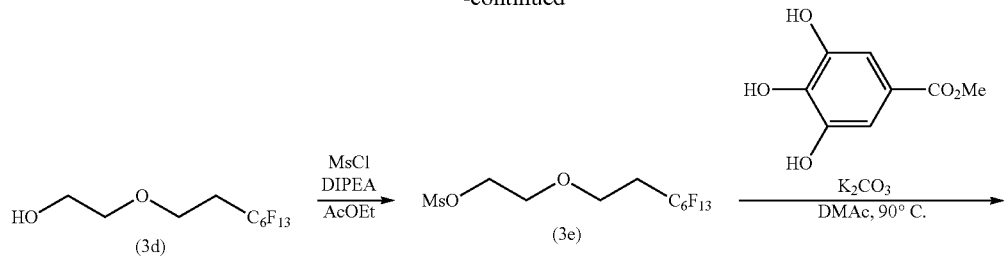
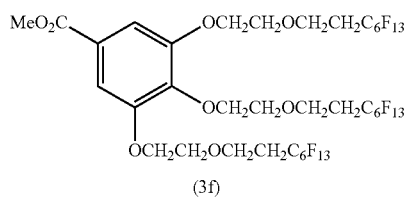
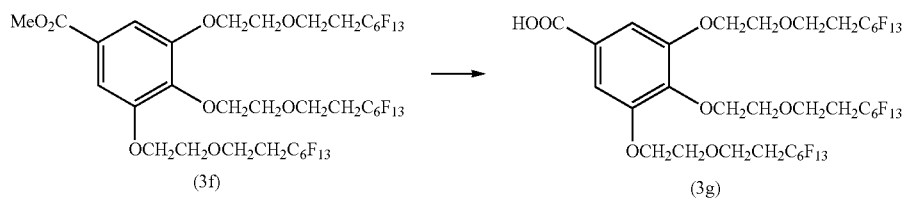
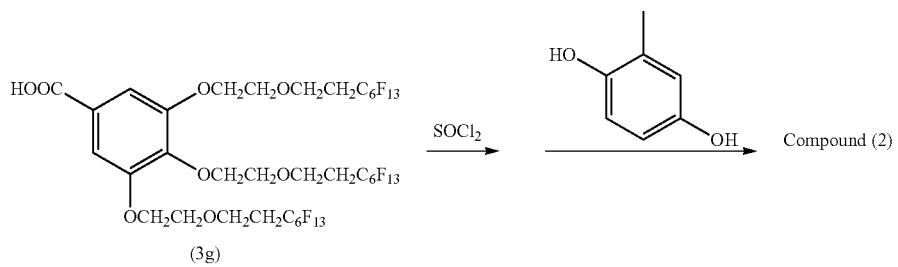
Synthesis Example 4
Synthesis of Compound (11)
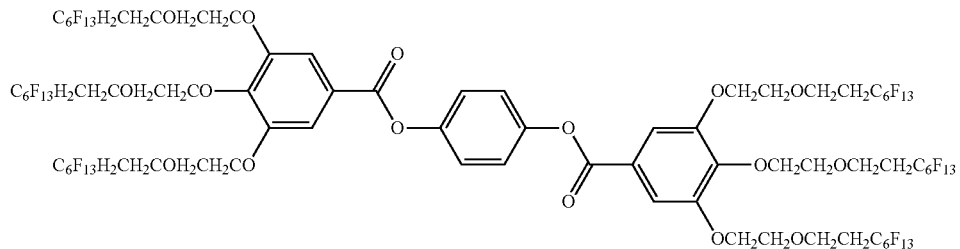

Compound (11) was obtained by using the same procedures used for the synthesis of compound (2), except that hydroquinone was used instead of methylhydroquinone.

$^1$H NMR (300 MHz, CDCl$_3$) δ 2.2-2.5 (m, 12H), 3.7-3.9 (m, 24H), 4.2 (m, 12H), 7.2 (s, 4H), 7.5 (s, 4H)

Synthesis Example 5

Synthesis of Compound (6)

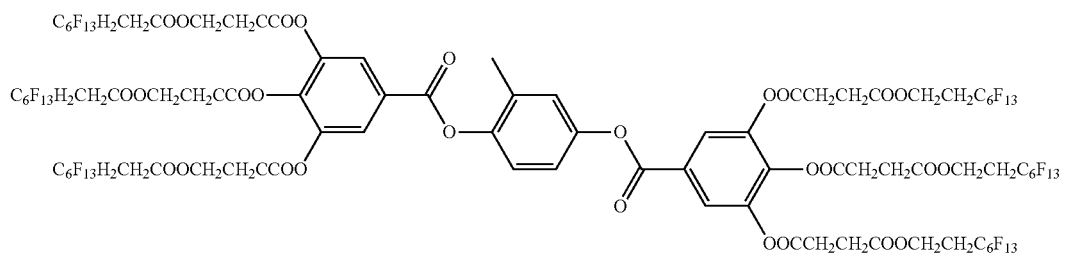

Compound (6) was synthesized by using the following route.

(5-1) Synthesis of Carboxylic Acid (5a)

A succinic anhydride (9.7 g, 49 mmol), tetrahydrofuran (10 ml), and triethylamine (0.2 mL) were added to 2-(perfluorohexyl)ethanol (33.3 g, 46 mmol). A reaction was allowed for 60 min at an increased temperature of 100° C. while stirring the mixture. Water (100 mL) was added after cooling the mixture to 30° C., and the precipitated crystals formed upon further cooling to 15° C. were filtered off to obtain carboxylic acid (5a; 39.7 g, 94%).

(5-2) Synthesis of Carboxylic Acid (5b)

Carboxylic acid (5a; 15 g, 32 mmol) was reacted with thionyl chloride (2.6 mL, 36 mmol) in toluene to prepare acid chloride 4b. Gallic acid monohydrate (1.5 g, 8 mmol) was heated under reflux to dehydrate in toluene (10 mL) After cooling the mixture to room temperature, tetrahydrofuran (12 mL) was added and dissolved, and the acid chloride 4b prepared in advance was added. After ice-cooling the reaction system, pyridine (4 mL) was slowly dropped, and a reaction was allowed at room temperature for 1 hour. After adding pyridine (2 mL) and water (20 mL), the mixture was stirred at 50° C. for 1 hour. The mixture was separated by addition of ethyl acetate, and the organic layer was washed with brine. The organic layer was then concentrated, and recrystallized from ethyl acetate/methanol (1/20) to give carboxylic acid (5b; 9.5 g, 84%).

$^1$H NMR (400 MHz, CDCl$_3$) δ 2.4-2.6 (m, 6H), 2.7-2.8 (m, 6H), 2.9-3.0 (m, 6H), 4.4-4.5 (m, 6H), 7.8 (s, 2H)

(5-3) Synthesis of Compound (6)

Compound (6) was obtained in the same manner as in the synthesis of compound (1), except that carboxylic acid (5b) was used instead of carboxylic acid (1d).

$^1$H NMR (300 MHz, CDCl$_3$) δ 2.2 (s, 3H), 2.4-2.6 (m, 12H), 2.7-2.8 (m, 12H), 2.9-3.0 (m, 12H), 4.4-4.5 (m, 12H), 7.0-7.2 (m, 3H), 7.9 (s×2, 4H)

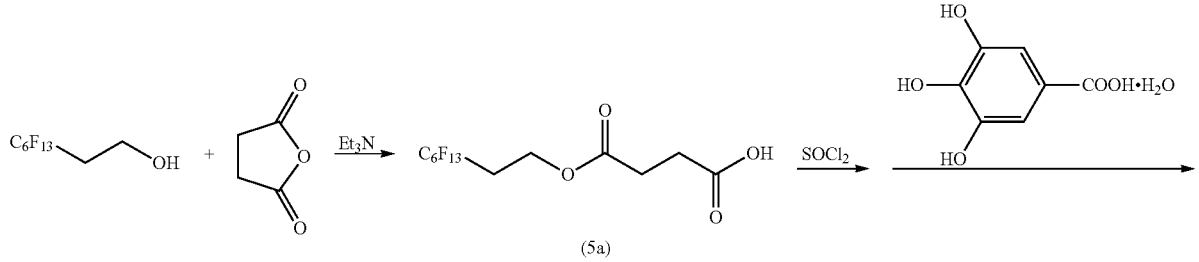

(5a)

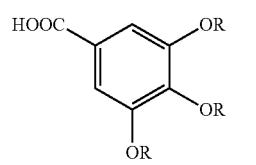

(5b)

R= OCCH$_2$CH$_2$COOCH$_2$CH$_2$C$_6$F$_{13}$

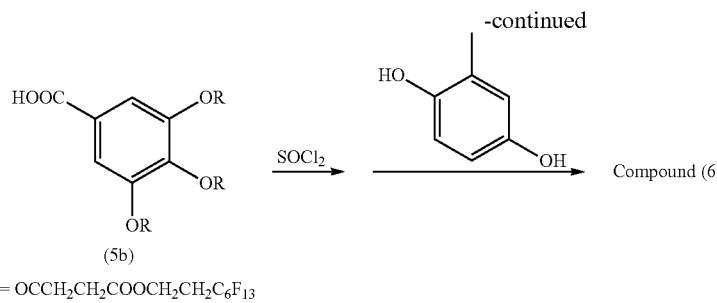

R= OCCH$_2$CH$_2$COOCH$_2$CH$_2$C$_6$F$_{13}$

Synthesis Example 6

Synthesis of Compound (7)

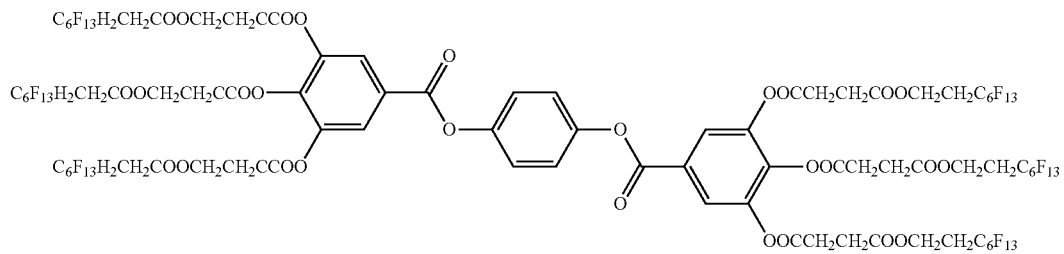

Compound (7) was obtained by using the same procedures used for compound (6), except that hydroquinone was used instead of methylhydroquinone.

$^1$H NMR (300 MHz, CDCl$_3$) δ 2.4-2.6 (m, 12H), 2.7-2.8 (m, 12H), 2.9-3.0 (m, 12H), 4.4-4.5 (m, 12H), 7.2 (s, 4H), 7.9 (s, 4H)

Synthesis Example 7

Synthesis of Compound (9)

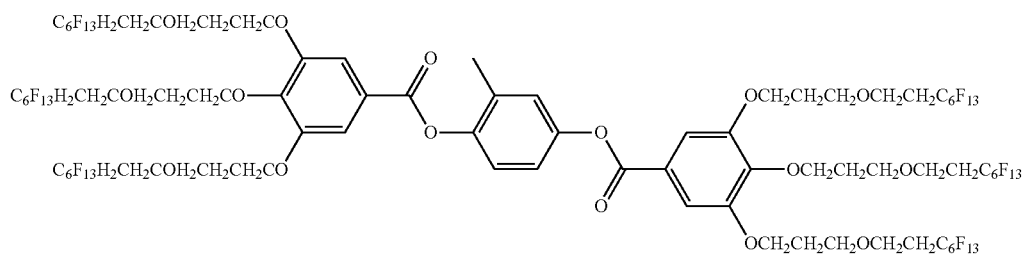

Compound (9) was synthesized by using the following route.

(7-1) Synthesis of Ester (7b)

2-(Perfluorohexyl)ethanol (18.2 g, 50 mmol) was added to toluene, and potassium hydroxide (3.5 g)/water (3.5 ml) was added to the mixture. Under ice-cooled condition, acrylic acid tert-butyl ester (10.3 ml, 70 mmol) and tetrabutylammonium bromide (1.61 g, 5 mmol) were added, and the mixture was stirred at room temperature for 3 hours. The reaction was quenched by addition of dilute hydrochloric acid. The mixture was separated in an ethyl acetate/water system, and the resulting liquid was concentrated with a rotary evaporator. After column purification, purified ester (7b; 19.0 g, yield 77%) was obtained.

(7-2) Synthesis of Alcohol (7c)

A bis(2-methoxyethoxy)aluminum hydride toluene solution (13.2 g, 42.5 mmol; Aldrich) was added to THF (100 ml), and the mixture was ice-cooled. Ester (7b; 19.0 g, 38.6 mmol) dissolved in THF (30 ml) was then dropped into the solution. The mixture with the dropped ester was stirred at room temperature for 1 hour. The reaction was quenched by addition of ethyl acetate. The mixture was separated by addition of dilute hydrochloric acid, and the resulting liquid was concentrated. After column purification, alcohol (7c; 9.0 g, yield 55%) was obtained.

(7-3) Synthesis of Compound (9)

After the production of alcohol (7c), compound (9) was synthesized by using the same synthesis methods used for the synthesis of compound (2), except that alcohol (7c) was used instead of alcohol (3d).

$^1$H NMR (300 MHz, CDCl$_3$) δ 1.9-2.1 (m, 12H), 2.2 (s, 3H), 2.3-2.5 (m, 12H), 3.6-3.8 (m, 24H), 4.1-4.2 (t, 12H), 7.0-7.2 (m, 3H), 7.4-7.5 (s×2, 4H)

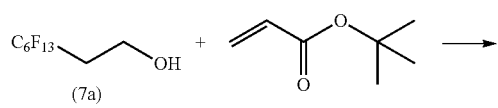
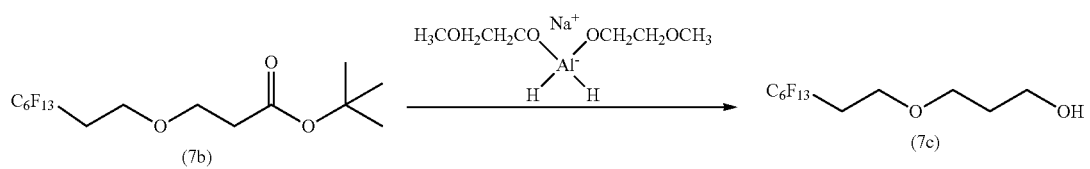
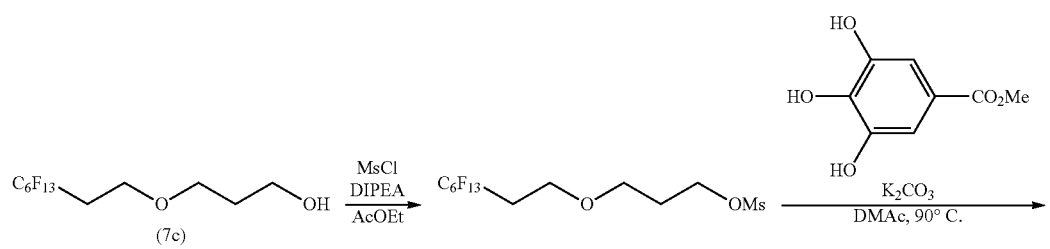
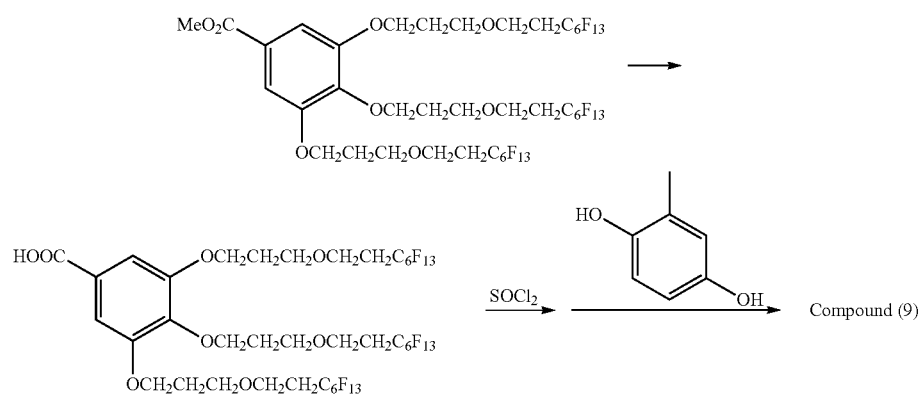
Synthesis Example 8
Synthesis of Compound (10)
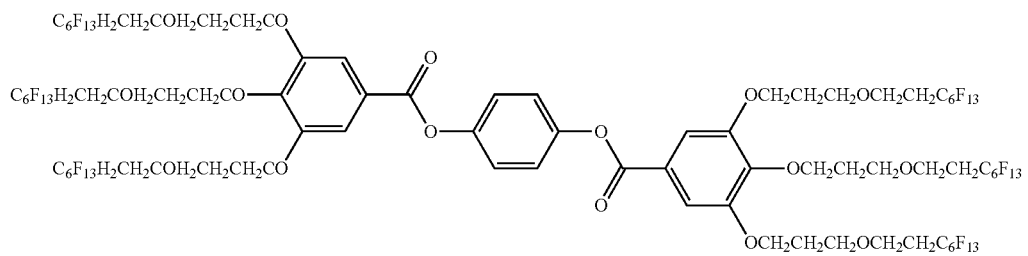

Compound (10) was synthesized in the same manner as in the synthesis of compound (9), except that hydroquinone was used instead of methylhydroquinone.

$^1$H NMR (300 MHz, CDCl$_3$) δ 1.9-2.2 (m, 12H), 2.3-2.5 (m, 12H), 3.6-3.8 (m, 24H), 4.1-4.2 (t, 12H), 7.2 (s, 4H), 7.4 (s, 4H)

Synthesis Example 9

Synthesis of Compound (5)

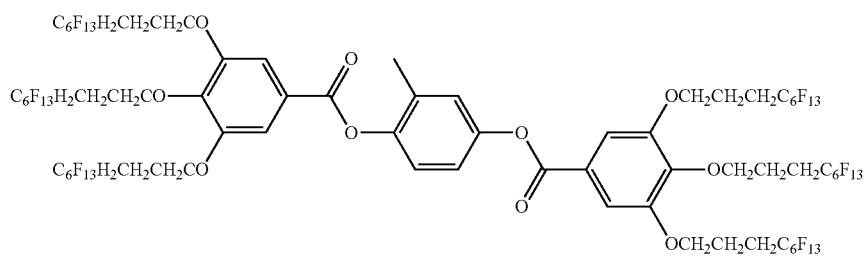

Compound (5) was synthesized by using the following route. Specifically, compound (5) was synthesized in the same manner as in the synthesis of compound (2), except that a commercially available reagent 3-(perfluorohexyl) propanol was used instead of alcohol (3d).

$^1$H NMR (300 MHz, CDCl$_3$) δ 2.0-2.5 (m, 27H), 4.0-4.2 (m, 12H), 7.0-7.2 (m, 3H), 7.4 (s×2, 4H)

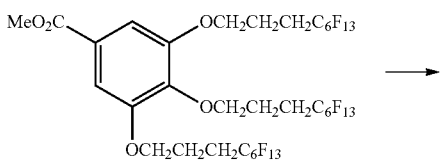

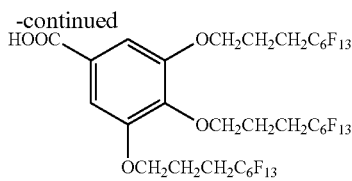

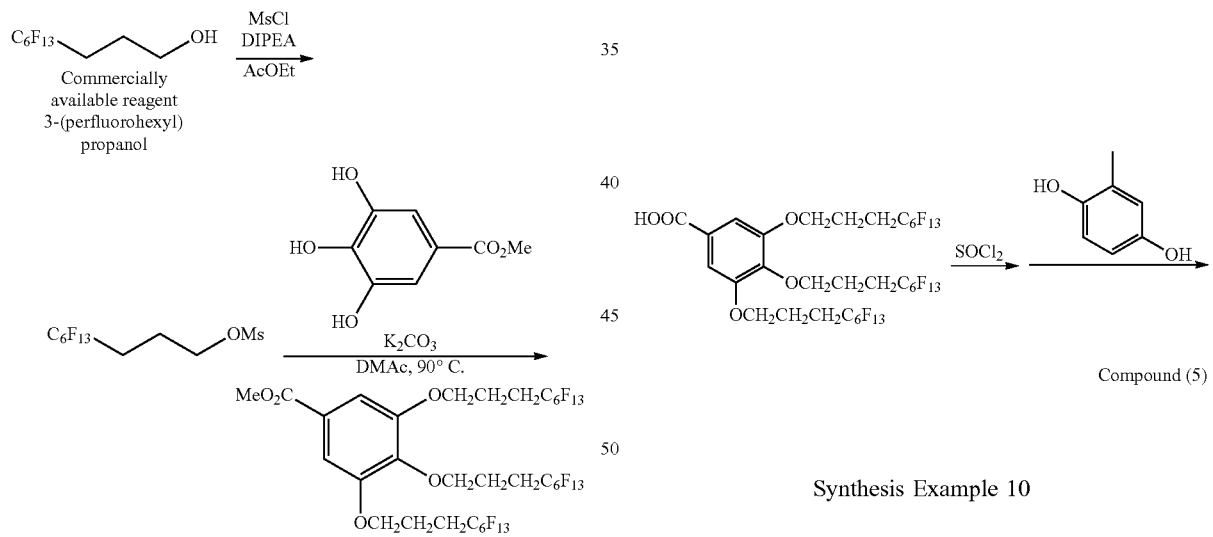

Compound (5)

Synthesis Example 10

Synthesis of Compound (14)

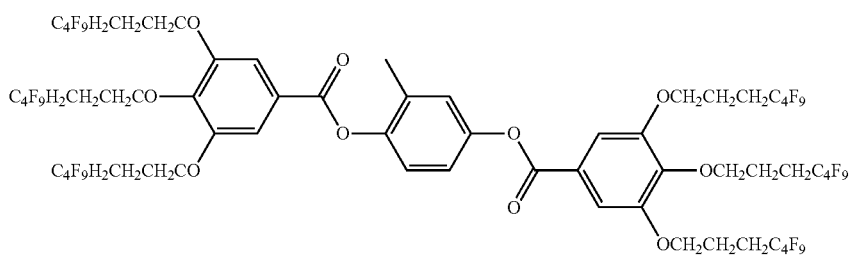

Compound (14) was synthesized by using the same methods used for the synthesis of compound (5), except that a commercially available reagent 3-(perfluorobutyl) propanol was used instead of the commercially available reagent 3-(perfluorohexyl)propanol.

$^1$H NMR (300 MHz, CDCl$_3$) δ 2.0-2.5 (m, 27H), 4.0-4.2 (m, 12H), 7.0-7.2 (m, 3H), 7.4-7.5 (s×2, 4H)

Synthesis Example 11

Synthesis of Compound (13)

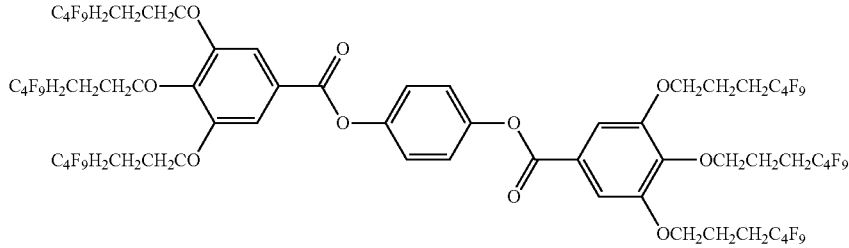

Compound (13) was synthesized by using the same methods used for the synthesis of compound (14), except that hydroquinone was used instead of methylhydroquinone.

$^1$H NMR (300 MHz, CDCl$_3$) δ 2.0-2.5 (m, 24H), 4.0-4.2 (m, 12H), 7.2 (s, 4H), 7.4 (s, 4H)

Synthesis Example 12

Synthesis of Compound (4)

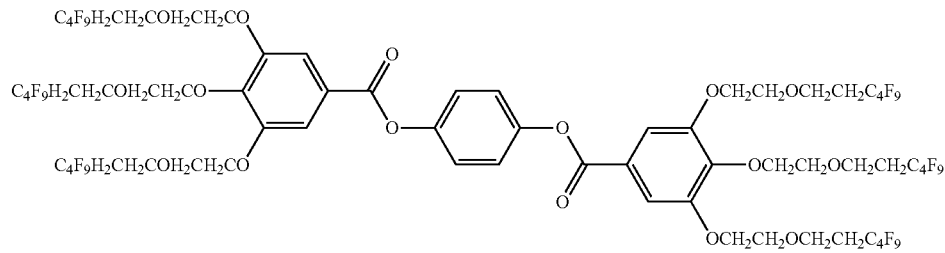

Compound (4) was synthesized by using the same methods used for the synthesis of compound (11), except that 2-(perfluorobutyl)ethanol was used instead of 2-(perfluorohexyl)ethanol.

$^1$H NMR (300 MHz, CDCl$_3$) δ 2.2-2.5 (m, 12H)), 3.7-3.9 (m, 24H), 4.2 (m, 12H), 7.2 (s, 4H), 7.5 (s, 4H)

Synthesis Example 13

Synthesis of Compound (50)

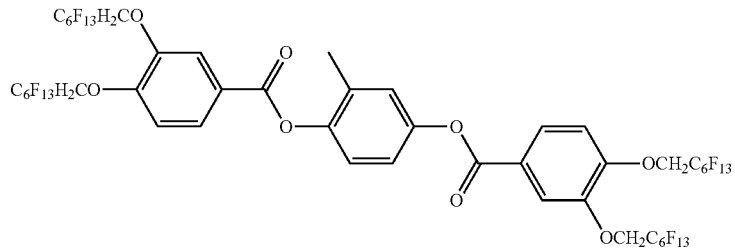

Compound (50) was synthesized by using the following route.

(13-1) Synthesis of Aldehyde (13a)

3,4-Dihydroxybenzaldehyde (2.1 g, 15 mmol) and potassium carbonate (4.3 g, 30.8 mmol) were added to DMAc (10 ml), and the mixture was heated to 90° C. in a nitrogen atmosphere. Ester (1b; 14.8 g, 30.8 mmol) synthesized in Synthesis Example 1 was dropped, and the mixture was stirred at 90° C. for 2 hours. After being cooled to room temperature, the mixture was separated in an ethyl acetate/water system. The resulting liquid was concentrated, and column purified to give aldehyde (13a; 10.8 g, yield 90%).

$^1$HNMR (300 MHz, CDCl$_3$) δ 4.4-4.7 (q, 4H), 7.1 (d, 1H), 7.5 (s, 1H), 7.6 (d, 1H), 9.9 (s, 1H)

(13-2) Synthesis of Carboxylic Acid (13b)

Aldehyde (13a; 10.8 g, 13.5 mmol) was induced to carboxylic acid (13b) according to the method described in paragraphs [0085] to [0087] in page 10 of JP-A-2002-97170 (6.9 g, yield 78%).

$^1$HNMR (300 MHz, DMSO-d$_6$) δ 4.8-5.0 (q, 4H), 7.2 (d, 1H), 7.6 (s, d, 2H), 12.8-13.0 (brs, 1H)

(13-3) Synthesis of Compound (50)

Carboxylic acid (13b; 2.45 g, 3.0 mmol) was reacted with thionyl chloride (0.33 ml, 4.5 mmol) in toluene (10 ml) and a catalytic amount of DMF to produce an acid chloride. After removing the excess thionyl chloride and toluene, THF (5 ml) and a catalytic amount of DMAP were added to the system. THF (5 ml), and methylhydroquinone (186 mg, 1.5 mmol) dissolved in diisopropylethylamine (0.57 ml) were then dropped into the mixture, and a reaction was allowed at room temperature for 3 hours. This was followed by separation, concentration with an evaporator, column purification, and recrystallization from methanol to give compound (50; 1.8 g, yield 69%).

$^1$H NMR (400 MHz, CDCl$_3$) δ 2.3 (s, 3H), 4.5-4.7 (m, 8H), 7.0-7.2 (s×3, d×2, 5H), 7.8 (s×2, 2H), 8.0 (d×2, 2H)

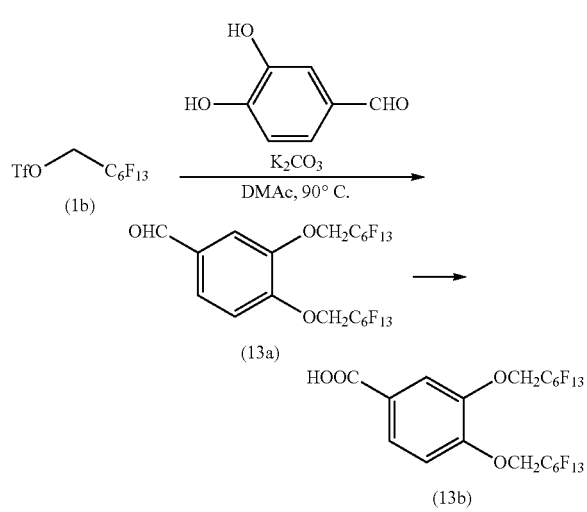

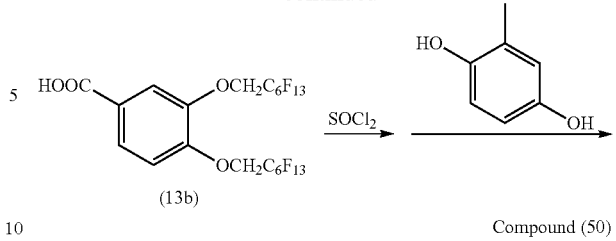

Compound (50)

Synthesis Example 14

Synthesis of Compound (51)

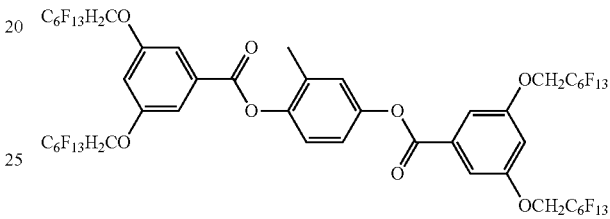

Compound (51) was synthesized by using the following route.

(14-1) Synthesis of Ester (14a)

3,5-Dihydroxybenzoic acid methyl ester (2.5 g, 15 mmol) and potassium carbonate (4.3 g, 30.8 mmol) were added to DMAc (10 ml) and the mixture was heated to 90° C. in a nitrogen atmosphere. Ester (1b; 14.8 g, 30.8 mmol) described in Synthesis Example 1 was dropped, and the mixture was stirred at 90° C. for 2 hours. After being cooled to room temperature, the mixture was separated in an ethyl acetate/water system. The resulting liquid was concentrated, and column purified to give aldehyde (14a; 11.6 g, yield 93%).

$^1$H NMR (300 MHz, CDCl$_3$) δ 4.0 (s, 3H), 4.4-4.7 (t, 4H), 6.8 (s, 1H), 7.3 (s, 2H)

(14-2) Synthesis of Carboxylic Acid (14b)

Ester (14a; 11.6 g, 13.9 mmol) was added to ethanol (30 ml) and water (3 ml), and potassium hydroxide (1.2 g, 20.9 mmol) was added. The mixture was heated under reflux for 2 hours. After being cooled to room temperature, the mixture was dropped into a hydrochloric acid aqueous solution. The resulting solid was suction filtered to obtain carboxylic acid (14b; 8.6 g, yield 76%).

(14-3) Synthesis of Compound (51)

Carboxylic acid (14b; 2.45 g, 3.0 mmol) was reacted with thionyl chloride (0.33 ml, 4.5 mmol) in toluene (10 ml) and a catalytic amount of DMF to produce an acid chloride. After removing the excess thionyl chloride and toluene, THF (5 ml) and a catalytic amount of DMAP were added to the system. THF (5 ml), and methylhydroquinone (186 mg, 1.5 mmol) dissolved in 0.57 ml of diisopropylethylamine were dropped into the mixture, and a reaction was allowed at room temperature for 3 hours. This was followed by separation, concentration with an evaporator, column purification, and recrystallization from methanol to give compound (51; 1.8 g, yield 690).

$^1$H NMR (300 MHz, CDCl$_3$) δ 2.3 (s, 3H), 4.5-4.7 (t, 8H), 6.9 (m, 2H), 7.0-7.2 (s×3, 3H), 7.5 (dd×2, 4H)

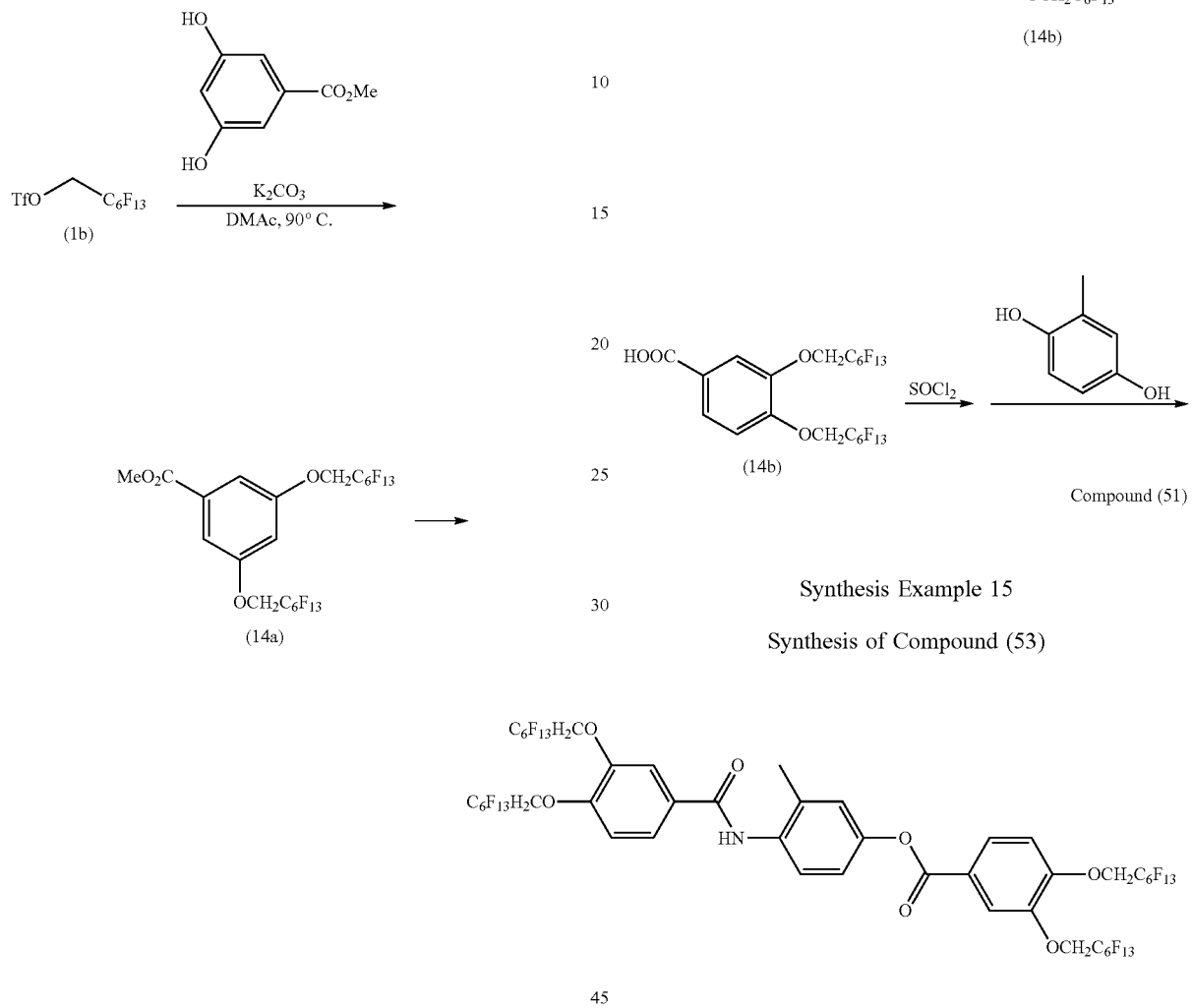

Synthesis Example 15

Synthesis of Compound (53)

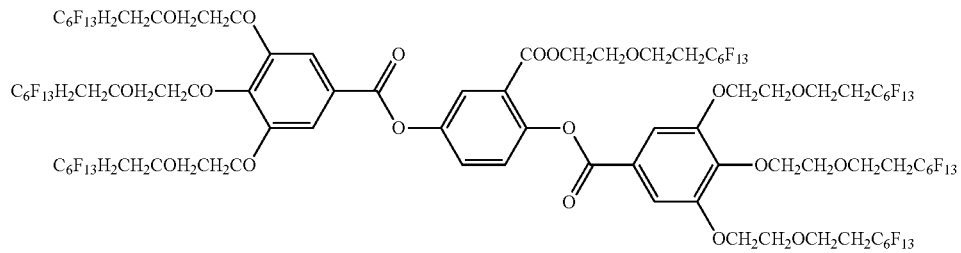

Compound (53) was synthesized in the same manner as for compound (50), except that 4-amino-m-cresol was used instead of methylhydroquinone.

$^1$H NMR (300 MHz, THF-d$_8$) δ 2.5 (s, 3H), 4.8-5.0 (m, 8H), 7.1 (d, 1H), 7.2 (s, 1H), 7.3-7.4 (d×2, 2H), 7.6 (d, 1H), 7.8 (d, 1H), 7.9 (s, 1H), 8.0 (s, 1H), 8.1 (d, 1H), 9.0 (s, 1H)

Synthesis Example 16

Synthesis of Compound (35)

Compound (35) was synthesized by using the following route.

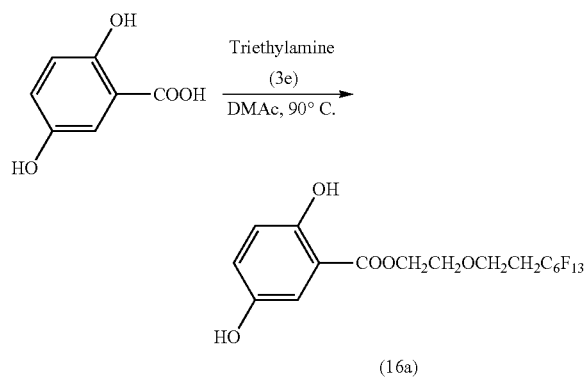

(16a)

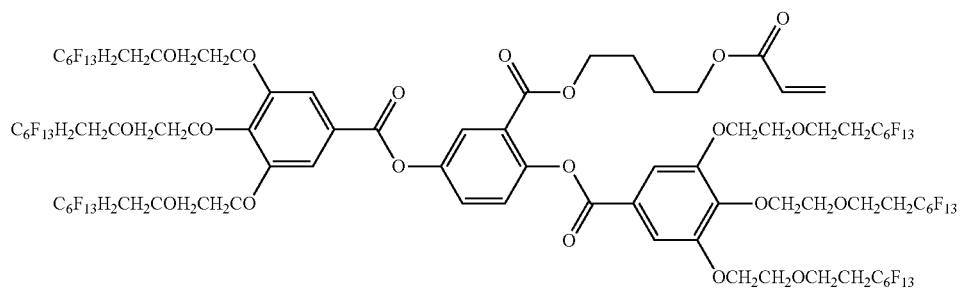

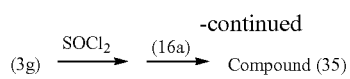

(16-1) Synthesis of Compound (16a)

2,5-Dihydroxybenzoic acid (800 mg, 5.19 mmol), triethylamine (731 μl, 5.20 mmol), and the product (3e) described in Synthesis Example 3 were added to DMAc (8 ml), and the mixture was stirred for 5 hours at an increased outer temperature of 90° C. Ethyl acetate was added after cooling the mixture to room temperature, and the mixture was separated by adding 1 mol/l of hydrochloric acid. After removing the aqueous layer, saturated brine was added to perform a separation procedure again, and the resulting liquid was concentrated with a rotary evaporator. Hexane was added, and the mixture was heated under reflux. Compound (16a) was obtained after suction filtration (1.5 g, yield 530).

(16-2) Synthesis of Compound (35)

Carboxylic acid (3 g; 1.0 g, 0.75 mmol) described in Synthesis Example 3 was dissolved in THF (1 ml) to which a catalytic amount of DMF had been added. Thionyl chloride (97.4 μl, 1.35 mmol) was then dropped into the mixture. After being stirred at room temperature for 1 hour, the mixture was heated to 50° C. to remove the thionyl chloride, and THF (1 ml) was added to prepare a solution (*). Separately, a THF (1 ml) solution of compound (16a; 194.3 mg, 0.36 mmol) was ice-cooled, and the solution (*), diisopropylethylamine (141.5 μl, 0.821 mmol), and a catalytic amount of N-methylimidazole were added in order at the maintained inner temperature of 10° C. or less. A reaction was allowed at room temperature for 1 hour, and the mixture was separated with ethyl acetate and water. The organic layer was dried over sodium sulfate, concentrated with a rotary evaporator, and column purified to obtain compound (35) (0.85 g, yield 75%)

$^1$H NMR (300 MHz, CDCl$_3$) δ 2.3-2.6 (m, 14H), 3.5 (t, 2H), 3.6 (t, 2H), 3.8-4.0 (m, 24H), 4.2-4.4 (m, 14H), 7.3 (s, 1H), 7.4-7.5 (m, 5H), 7.9 (s, 1H)

Synthesis Example 17

Synthesis of Compound (39)

Compound (39) was synthesized by using the following route, in the same manner as in the synthesis of compound (35), except that sulfonic acid ester (17a) was used instead of (3e). Sulfonic acid ester (17a) may be synthesized by using a known method, using 4-hydroxybutylacrylate as raw material.

$^1$H NMR (300 MHz, CDCl$_3$) δ 1.6-1.7 (brs, 4H), 2.3-2.6 (m, 12H), 3.7-3.9 (m, 24H), 4.1 (t, 2H), 4.2-4.3 (m, 14H), 5.8 (d, 1H), 6.0-6.1 (dd, 1H), 6.3-6.4 (d, 1H), 7.3 (1H), 7.4 (1H), 7.5 (s, 2, 4H), 7.9 (1H)

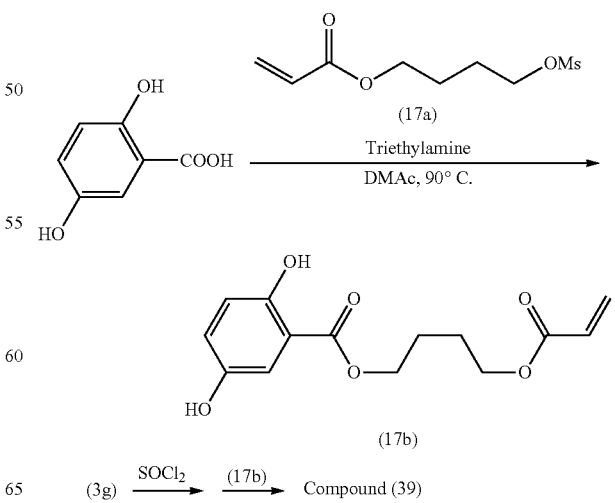

Synthesis Example 18

Synthesis of Compound (37)

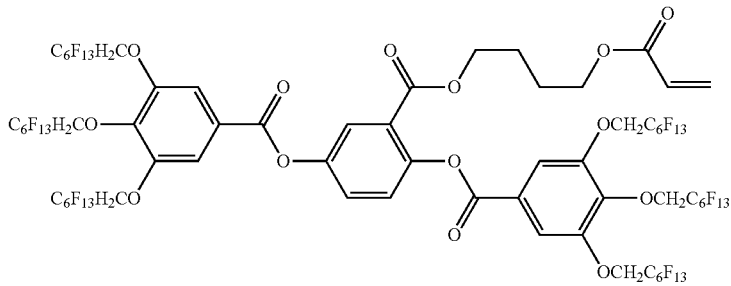

Compound (37) was synthesized in the same manner as in the synthesis of compound (39), except that carboxylic acid (1d) described in Synthesis Example 1 was used instead of carboxylic acid (3g).

$^1$H NMR (300 MHz, CDCl$_3$) δ 1.7-1.8 (brs, 4H), 4.1 (t, 3H) 4.3 (t, 2H), 4.5-4.7 (m, 12H), 5.8 (d, 1H), 6.0-6.1 (dd, 1H), 6.3-6.4 (d, 1H), 7.3 (1H), 7.4 (1H), 7.5 (s×2, 4H), 7.9 (1H)

Synthesis Example 19

Synthesis of Compound (40)

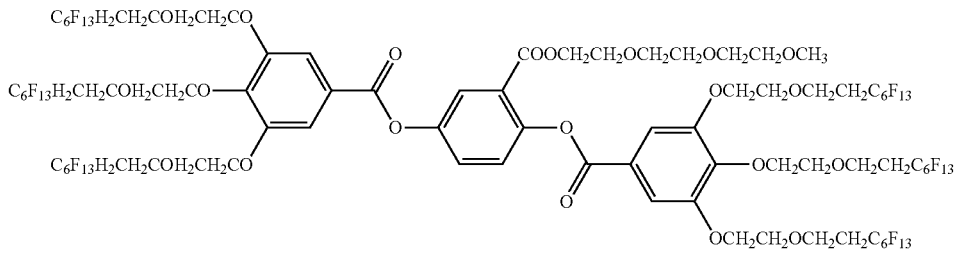

Compound (40) was synthesized by using the following route, in the same manner as in the synthesis of compound (35), except that sulfonic acid ester (19a) was used instead of (3e). Sulfonic acid ester (19a) may be synthesized by using a known method, using triethylene glycol monomethyl ether as raw material.

$^1$H NMR (300 MHz, CDCl$_3$) δ 2.3-2.6 (m, 12H), 3.3 (s, 3H), 3.5-3.7 (m, 10H), 3.8-4.0 (m, 24H), 4.2 (m, 12H), 4.3 (t, 2H), 7.3 (2H), 7.5 (s×2, 4H), 7.9 (1H)

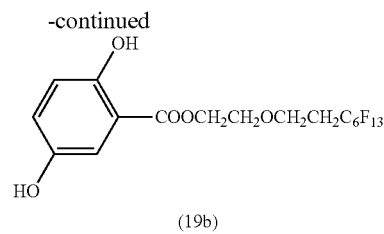

Synthesis Example 20

Synthesis of Compound (48)

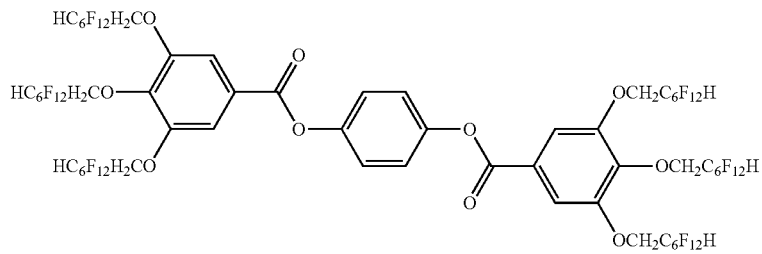

Compound (48) was synthesized in the same manner as in the synthesis of compound (1), except that 1H,1H,7H-dodecafluoro-1-heptanol was used instead of alcohol (1a).

$^1$H NMR (300 MHz, CDCl$_3$) δ 4.5-4.7 (m, 12H), 5.8-6.2 (m, 6H), 7.3 (s, 2H), 7.6 (s, 4H)

Synthesis Example 21

Synthesis of Compound (33)

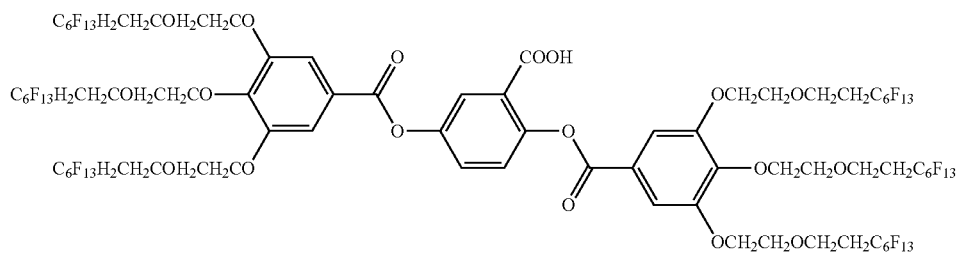

Compound (33) was synthesized by using the following route.

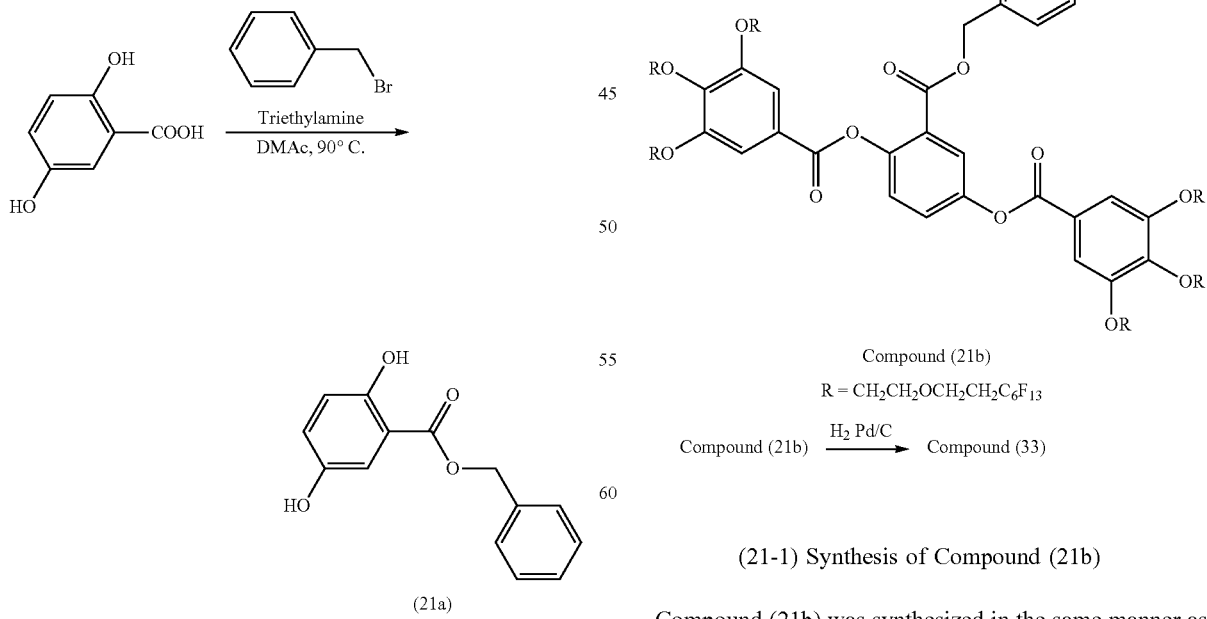

Compound (21b)
R = CH$_2$CH$_2$OCH$_2$CH$_2$C$_6$F$_{13}$

Compound (21b) $\xrightarrow{\text{H}_2\text{ Pd/C}}$ Compound (33)

(21-1) Synthesis of Compound (21b)

Compound (21b) was synthesized in the same manner as in the synthesis of compound (35), except that benzyl bromide was used instead of (3e).

(21-2) Synthesis of Compound (33)

Compound (21b; 457 mg, 0.158 mmol), and palladium carbon (33.5 mg, 0.0158 mmol) were added to ethyl acetate, and deaeration and hydrogen charging procedures were performed. The mixture was stirred at room temperature for 2 hours, celite filtered, and concentrated with a rotary evaporator. The resulting liquid was washed with hexane by being heated under reflux to obtain compound (33; 260 mg, yield 59%).

$^1$H NMR (300 MHz, CDCl$_3$) δ 2.3-2.6 (m, 12H), 3.7-3.9 (m, 24H), 4.2-4.3 (m, 12H), 7.3 (s, 1H), 7.4-7.5 (m, 5H), 7.9 (s, 1H)

Examples 1 to 34, and Comparative Examples 1 to 6

Optically anisotropic films were formed with the compounds shown in Table 1, and each film was evaluated. First, a coating liquid of the composition below was prepared. The compound concentration was 0.01 parts by mass, 0.02 mass %, 0.03 parts by mass, 0.05 mass %, 0.10 parts by mass, and 0.20 parts by mass with respect to the rod-like liquid crystal compound. Rod-like liquid crystal compound 1: 100 parts by mass
Chiral agent (A): 2.8 parts by mass
IRGACURE 819 (Ciba Japan): 3 parts by mass
Compounds shown in Tables 1 and 2: as above
Solvents shown in Tables 1 and 2: amounts that make the solute concentration 25 mass %
Rod-Like Liquid Crystal Compound 1

Fifty microliters of the coating liquid prepared was taken into a micropipetter, dropped onto an alignment film-attached glass (SE-130), and spin coated at a 2,000 rpm rotation speed. The sample was heated at 85° C. for 2 min, allowed to cool for 1 min, and irradiated with ultraviolet light in a nitrogen atmosphere (ultraviolet intensity: 500 mJ/m$^2$) to form an optically anisotropic film. The optically anisotropic film had a thickness of about 5 μm.

The orientation of each optically anisotropic film was evaluated by visual inspection and haze. Haze was measured with a haze mater NDH2000 (Nippon Denshoku).

The compounds' alignment promoting effect was evaluated according to the following criteria in an alignment promotion test, using the haze value of the optically anisotropic films that had the compound concentration of 0.01 mass %. At 0.01 mass % concentration, the compounds were completely dissolved in the solvent, and smaller haze values mean greater liquid crystal alignment promoting effects.
Excellent: less than 5.5
Good: 5.5 or more and less than 8.5
Acceptable: 8.5 or more and less than 10.0
Poor: 10.0 or more Dissolution and alignment promoting effect were evaluated according to the following criteria in a dissolution and alignment promotion test, using the haze value of the optically anisotropic films that had the compound concentrations of 0.02 mass %, 0.03 mass %, 0.05 mass %, 0.10 mass %, and 0.20 mass %. Samples with higher ratings have more desirable solubility and greater alignment promoting effects. Lower ratings basically mean poorer solubility.
Excellent: less than 0.15
Good: 0.15 or more and less than 0.35
Acceptable: 0.35 or more and less than 0.90
Poor: 0.90 or more

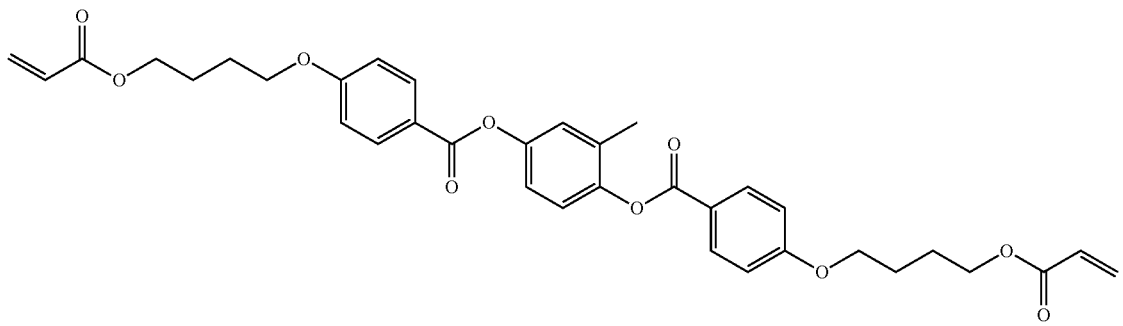

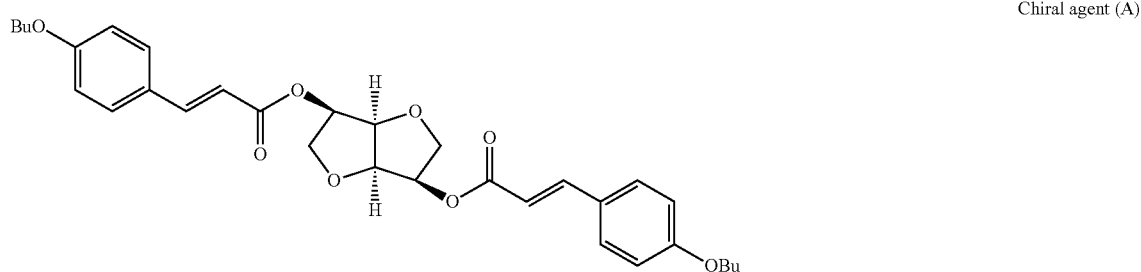

Chiral agent (A)

TABLE 1

| | Aligning agent | Solvent | Alignment Promotion test Concentration 0.01 mass % | Dissolution and alignment promotion test | | |
|---|---|---|---|---|---|---|
| | | | | Concentration 0.03 mass % | Concentration 0.10 mass % | Concentration 0.20 mass % |
| Ex. 1 | Compound 1 | Chloroform | Excellent | Excellent | Good | Good |
| Ex. 2 | Compound 2 | Chloroform | Excellent | Good | Good | Acceptable |
| Ex. 3 | Compound 11 | Chloroform | Excellent | Good | Good | Acceptable |
| Ex. 4 | Compound 6 | Chloroform | Excellent | Good | Good | Acceptable |
| Ex. 5 | Compound 10 | Chloroform | Excellent | Good | Good | Acceptable |
| Ex. 6 | Compound 5 | Chloroform | Excellent | Good | Good | Acceptable |
| Ex. 7 | Compound 14 | Chloroform | Excellent | Good | Good | Acceptable |
| Ex. 8 | Compound 4 | Chloroform | Excellent | Good | Good | Good |
| Ex. 9 | Compound 50 | Chloroform | Excellent | Excellent | Excellent | Acceptable |
| Ex. 10 | Compound 51 | Chloroform | Excellent | Excellent | Good | Good |
| Ex. 11 | Compound 35 | Chloroform | Excellent | Excellent | Excellent | Good |
| Ex. 12 | Compound 39 | Chloroform | Excellent | Good | Good | Acceptable |
| Ex. 13 | Compound 37 | Chloroform | Excellent | Good | Good | Acceptable |
| Ex. 14 | Compound 40 | Chloroform | Excellent | Good | Good | Acceptable |
| Ex. 15 | Compound 48 | Chloroform | Excellent | Good | Good | Acceptable |
| Com. Ex. 1 | Compound A | Chloroform | Acceptable | Good | Good | Poor |
| Ex. 16 | Compound 1 | Methyl ethyl ketone | Excellent | Excellent | Good | Good |
| Ex. 17 | Compound 2 | Methyl ethyl ketone | Excellent | Good | Good | Acceptable |
| Ex. 18 | Compound 11 | Methyl ethyl ketone | Excellent | Good | Good | Acceptable |
| Ex. 19 | Compound 6 | Methyl ethyl ketone | Excellent | Good | Good | Acceptable |
| Ex. 20 | Compound 10 | Methyl ethyl ketone | Excellent | Good | Good | Acceptable |
| Ex. 21 | Compound 5 | Methyl ethyl ketone | Excellent | Good | Good | Acceptable |
| Ex. 22 | Compound 14 | Methyl ethyl ketone | Excellent | Good | Good | Acceptable |
| Ex. 23 | Compound 4 | Methyl ethyl ketone | Excellent | Good | Good | Good |
| Ex. 24 | Compound 50 | Methyl ethyl ketone | Excellent | Good | Good | Acceptable |
| Ex. 25 | Compound 51 | Methyl ethyl ketone | Excellent | Excellent | Good | Good |
| Ex. 26 | Compound 35 | Methyl ethyl ketone | Excellent | Excellent | Excellent | Good |
| Ex. 27 | Compound 39 | Methyl ethyl ketone | Excellent | Good | Good | Acceptable |
| Ex. 28 | Compound 37 | Methyl ethyl ketone | Excellent | Good | Good | Acceptable |
| Com. Ex. 2 | Compound A | Methyl ethyl ketone | Good | Acceptable | Acceptable | Poor |
| Com. Ex. 3 | Compound B | Methyl ethyl ketone | Acceptable | Acceptable | Poor | Poor |

TABLE 2

| | Aligning agent | Solvent | Alignment Promotion test Concentration 0.01 mass % | Dissolution and alignment promotion test | | | | |
|---|---|---|---|---|---|---|---|---|
| | | | | Concentration 0.02 mass % | Concentration 0.03 mass % | Concentration 0.05 mass % | Concentration 0.10 mass % | Concentration 0.20 mass % |
| Ex. 31 | Compound 1 | Chloroform | Excellent | Good | Excellent | Excellent | Good | Good |
| Ex. 32 | Compound 51 | Chloroform | Excellent | Good | Excellent | Good | Good | Good |
| Ex. 33 | Compound 2 | Chloroform | Excellent | Good | Good | Good | Good | Acceptable |
| Ex. 34 | Compound 6 | Chloroform | Excellent | Good | Good | Good | Good | Acceptable |
| Com. Ex. 4 | Compound D | Chloroform | Excellent | Poor | Good | Good | Good | Good |
| Com. Ex. 5 | Compound E | Chloroform | Excellent | Poor | Good | Good | Good | Acceptable |
| Com. Ex. 6 | Compound F | Chloroform | Excellent | Poor | Poor | Good | Good | Acceptable |

Note:
0.01, 0.02, 0.03, 0.05, 0.10, and 0.20 in Tables 1 and 2 are the compound concentrations with respect to the rod-like liquid crystal compound.

[compound (30) of JP-A-2002-129162]                                                                 Compound (A)

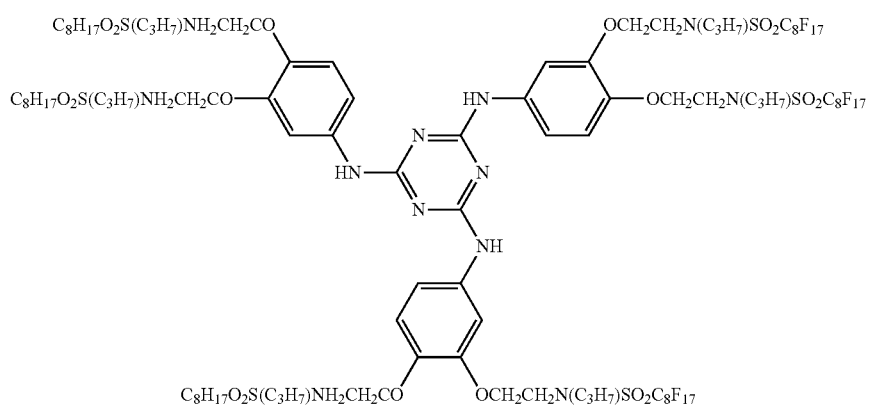

[compound (35) of JP-A-2002-129162]                                                                 Compound (B)

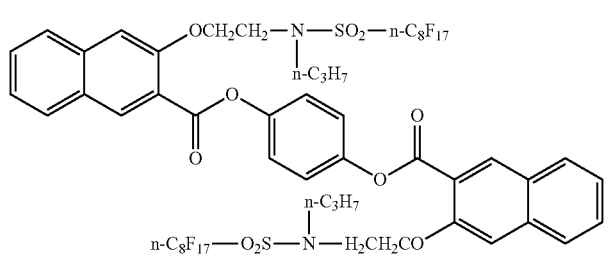

Compound (D)

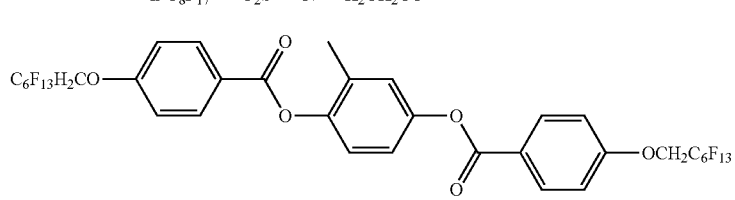

Compound (E)

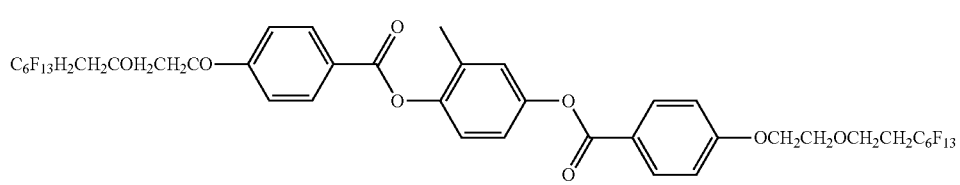

Compound (F)

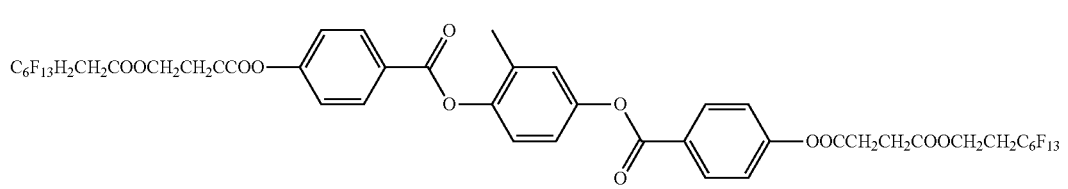

As shown in Table 1, it was confirmed that the compounds of the present invention had greater haze lowering effects, and higher solubility for the solvent even at increased concentrations. Though not being bound to any theory, such haze reductions are believed to be due to the large liquid crystal alignment effect of the compounds of the present invention providing desirable liquid crystal alignment also on the air interface side. Specifically, the compounds of the present invention are believed to be liquid crystal alignment promoting agents. The tendency remained the same with different solvents, confirming that the compounds of the present invention were applicable to a wide range of coating solvents, and were highly competent.

Further, as shown in Table 2, by comparing samples with backbones having the same fluoroalkyl side chains (Examples 31 and 32, and Comparative Example 4), it can be seen that the haze is lower at lower concentrations when there are two or three fluoroalkyl side chains (m=n=2, or m=n=3 in formula (I)) than when there is a single fluoroalkyl side chain (m=n=1 in formula (I)). By comparing Example 33 and Comparative Example 5, and Example 34 and Comparative Example 6, it can also be seen that the haze is lower at lower concentrations when there are three fluoroalkyl side chains (m=n=3 in formula (I)) than when there is a single fluoroalkyl side chain (m=n=1 in formula (I)). It can be seen from these results that more fluoroalkyl side chains increase the liquid crystal alignment effect, lower the haze also in low concentration ranges, and widen the competence range.

Example 35

Production of Infrared Reflecting Film

A composition liquid was prepared by using the following composition.
Rod-like liquid crystal compound 1: 100 parts by mass
Chiral agent (A): 5.0 parts by mass
IRGACURE 819 (Ciba Japan): 3.0 parts by mass
Compound (2) shown in Table 1: 0.03 parts by mass
Chloroform: amount that makes the solute concentration 25 mass %

Fifty microliters of the composition liquid was taken into a micropipetter, dropped onto an alignment film-attached glass (SE-130), and spin coated at a 2,000 rpm rotation speed. The sample was heated at 85° C. for 2 min, allowed to cool for 1 min, and irradiated with ultraviolet light in a nitrogen atmosphere (ultraviolet intensity: 500 mJ/m$^2$) to form an optically anisotropic film. The optically anisotropic film had a thickness of about 5 μm. The transmission spectrum of the optically anisotropic film was then measured with a spectrophotometer UV-3100PC (SHIMADZU). The result is shown in FIG. 1.

As shown in FIG. 1, the film produced in Example 35 was a selective reflecting film that had a center wavelength in the near-infrared region near 900 nm, and had optical anisotropy.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2012/066957, filed Jul. 3, 2012; Japanese Application No. 2011-164777, filed Jul. 27, 2011; and Japanese Application No. 2012-036512, filed Feb. 22, 2012, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A compound represented by the following formula (I):

(Hb-Sp$^1$-L$^1$-Sp$^2$-L$^2$)$_m$-A$^1$-L$^3$-T-L$^4$-A$^2$-(L$^5$-Sp$^3$-L$^6$-Sp$^4$-Hb)$_n$   Formula (I)

wherein L$^1$, L$^2$, L$^5$, and L$^6$ each independently represent a single bond, —O—, —S—, —CO—, —COO—, —OCO—, —COS—, —SCO—, —NRCO—, or —CONR—, L$^3$ is —COO— or —CONR—, L$^4$ is —OCO—, and T is

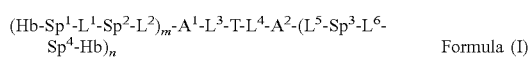

R in the formula (I) each independently represent a hydrogen atom or an alkyl group of 1 to 6 carbon atoms, Sp$^1$, Sp$^2$, Sp$^3$, and Sp$^4$ each independently represent a single bond or an alkylene group of 1 to 10 carbon atoms in which each of the hydrogen atoms of the alkylene group may be substituted with a fluorine atom, A$^1$ and A$^2$ represent a trivalent or tetravalent aromatic hydrocarbon group, wherein X represents an alkyl group of 1 to 8 carbon atoms, an alkoxy group, a halogen atom, a cyano group, or —COOR$^0$ in which R$^0$ represents a hydrogen atom, an alkyl or fluoroalkyl group in which each of the linking CH$_2$ may be substituted with O or S, or -Sp$^5$-P in which Sp$^5$ represents a single bond or an alkylene group of 1 to 10 carbon atoms in which each of the hydrogen atoms of the alkylene group may be substituted with a fluorine atom, and P represents a polymerizable group, Ya, Yb, Yc, and Yd each independently represent a hydrogen atom or an alkyl group of 1 to 4 carbon atoms, Hb's each independently represent a perfluoroalkyl or fluoroalkyl group of 2 to 30 carbon atoms, m and n are each independently 2 or 3, and the structures in a plurality of parentheses may be the same or different, o is an integer of 0 or more, and a plurality of X when o is 2 or more may be the same or different.

2. The compound according to claim 1, wherein, in the formula (I), L$^3$ is —COO—, L$^4$ is —OCO—, and A$^1$ and A$^2$ are each independently any one of the following:

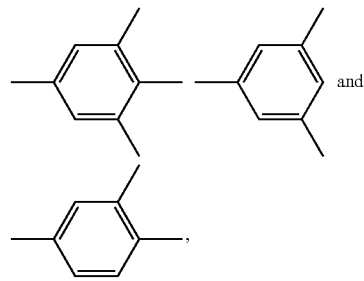

and
L$^2$ and L$^5$ are —O—.

3. The compound according to claim 1, wherein Hb's in the formula (I) are independently a perfluoroalkyl group of 2 to 30 carbon atoms.

4. A haze-lowering agent that comprises a compound represented by the following formula (I):

(Hb-Sp$^1$-L$^1$-Sp$^2$-L$^2$)$_m$-A$^1$-L$^3$-T-L$^4$-A$^2$-(L$^5$-Sp$^3$-L$^6$-Sp$^4$-Hb)$_n$   Formula (I)

wherein L$^1$, L$^2$, L$^5$, and L$^6$ each independently represent a single bond, —O—, —S—, —CO—, —COO—, —OCO—, —COS—, —SCO—, —NRCO—, or —CONR—, L$^3$ is —COO— or —CONR—, L$^4$ is —OCO—, and T is

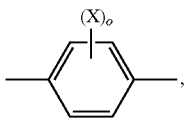

R in the formula (I) each independently represent a hydrogen atom or an alkyl group of 1 to 6 carbon atoms, $Sp^1$, $Sp^2$, $Sp^3$, and $Sp^4$ each independently represent a single bond or an alkylene group of 1 to 10 carbon atoms in which each of the hydrogen atoms of the alkylene group may be substituted with a fluorine atom, $A^1$ and $A^2$ represent a trivalent or tetravalent aromatic hydrocarbon group, wherein X represents an alkyl group of 1 to 8 carbon atoms, an alkoxy group, a halogen atom, a cyano group, or —COOR⁰ in which R⁰ represents a hydrogen atom, an alkyl or fluoroalkyl group in which each of the linking $CH_2$ may be substituted with O or S, or -Sp⁵-P in which $Sp^5$ represents a single bond or an alkylene group of 1 to 10 carbon atoms in which each of the hydrogen atoms of the alkylene group may be substituted with a fluorine atom, and P represents a polymerizable group, Ya, Yb, Yc, and Yd each independently represent a hydrogen atom or an alkyl group of 1 to 4 carbon atoms, Hb's each independently represent a perfluoroalkyl or fluoroalkyl group of 2 to 30 carbon atoms, m and n are each independently 2 or 3, and the structures in a plurality of parentheses may be the same or different, o is an integer of 0 or more, and a plurality of X when o is 2 or more may be the same or different.

5. A liquid crystal composition that comprises a polymerizable liquid crystal molecule, and a compound represented by the following formula (I):

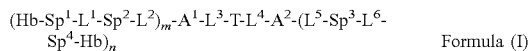

wherein $L^1$, $L^2$, $L^5$, and $L^6$ each independently represent a single bond, —O—, —S—, —CO—, —COO—, —OCO—, —COS—, —SCO—, —NRCO—, or —CONR—, $L^3$ is —COO— or —CONR—, $L^4$ is —OCO—, and T is

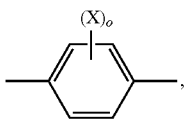

R in the formula (I) each independently represent a hydrogen atom or an alkyl group of 1 to 6 carbon atoms, $Sp^1$, $Sp^2$, $Sp^3$, and $Sp^4$ each independently represent a single bond or an alkylene group of 1 to 10 carbon atoms in which each of the hydrogen atoms of the alkylene group may be substituted with a fluorine atom, $A^1$ and $A^2$ represent a trivalent or tetravalent aromatic hydrocarbon group, wherein X represents an alkyl group of 1 to 8 carbon atoms, an alkoxy group, a halogen atom, a cyano group, or —COOR⁰ in which R⁰ represents a hydrogen atom, an alkyl or fluoroalkyl group in which each of the linking $CH_2$ may be substituted with O or S, or -Sp⁵-P in which $Sp^5$ represents a single bond or an alkylene group of 1 to 10 carbon atoms in which each of the hydrogen atoms of the alkylene group may be substituted with a fluorine atom, and P represents a polymerizable group, Ya, Yb, Yc, and Yd each independently represent a hydrogen atom or an alkyl group of 1 to 4 carbon atoms, Hb's each independently represent a perfluoroalkyl or fluoroalkyl group of 2 to 30 carbon atoms, m and n are each independently 2 or 3, and the structures in a plurality of parentheses may be the same or different, o is an integer of 0 or more, and a plurality of X when o is 2 or more may be the same or different.

6. The liquid crystal composition according to claim 5, wherein the polymerizable liquid crystal molecule is a rod-like liquid crystal molecule.

7. The liquid crystal composition according to claim 5, wherein said composition further contains at least one chiral compound.

8. A polymer material produced by polymerizing a liquid crystal composition, wherein the liquid crystal composition comprises a polymerizable liquid crystal molecule, and a compound represented by the following formula (I):

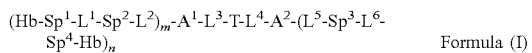

wherein $L^1$, $L^2$, $L^5$, and $L^6$ each independently represent a single bond, —O—, —S—, —CO—, —COO—, —OCO—, —COS—, —SCO—, —NRCO—, or —CONR—, $L^3$ is —COO— or —CONR—, $L^4$ is —OCO—, and T is

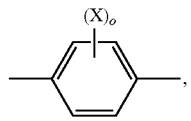

R in the formula (I) each independently represent a hydrogen atom or an alkyl group of 1 to 6 carbon atoms, $Sp^1$, $Sp^2$, $Sp^3$, and $Sp^4$ each independently represent a single bond or an alkylene group of 1 to 10 carbon atoms in which each of the hydrogen atoms of the alkylene group may be substituted with a fluorine atom, $A^1$ and $A^2$ represent a trivalent or tetravalent aromatic hydrocarbon group, wherein X represents an alkyl group of 1 to 8 carbon atoms, an alkoxy group, a halogen atom, a cyano group, or —COOR⁰ in which R⁰ represents a hydrogen atom, an alkyl or fluoroalkyl group in which each of the linking $CH_2$ may be substituted with O or S, or -Sp⁵-P in which $Sp^5$ represents a single bond or an alkylene group of 1 to 10 carbon atoms in which each of the hydrogen atoms of the alkylene group may be substituted with a fluorine atom, and P represents a polymerizable group, Ya, Yb, Yc, and Yd each independently represent a hydrogen atom or an alkyl group of 1 to 4 carbon atoms, Hb's each independently represent a perfluoroalkyl or fluoroalkyl group of 2 to 30 carbon atoms, m and n are each independently 2 or 3, and the structures in a plurality of parentheses may be the same or different, o is an integer of 0 or more, and a plurality of X when o is 2 or more may be the same or different.

9. A film that contains at least one polymer material produced by polymerizing a liquid crystal composition, wherein the liquid crystal composition comprises a polymerizable liquid crystal molecule, and a compound represented by the following formula (I):

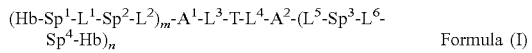

wherein $L^1$, $L^2$, $L^5$, and $L^6$ each independently represent a single bond, —O—, —S—, —CO—, —COO—, —OCO—, —COS—, —SCO—, —NRCO—, or —CONR—, $L^3$ is —COO— or —CONR—, $L^4$ is —OCO—, and T is

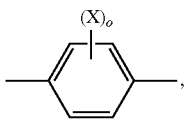

R in the formula (I) each independently represent a hydrogen atom or an alkyl group of 1 to 6 carbon atoms, $Sp^1$, $Sp^2$, $Sp^3$, and $Sp^4$ each independently represent a single bond or an alkylene group of to 10 carbon atoms in which each of the hydrogen atoms of the alkylene group may be substituted with a fluorine atom, $A^1$ and $A^2$ represent a trivalent or tetravalent aromatic hydrocarbon group, wherein X represents an alkyl group of 1 to 8 carbon atoms, an alkoxy group, a halogen atom, a cyano group, or —COOR$^0$ in which $R^0$ represents a hydrogen atom, an alkyl or fluoroalkyl group in which each of the linking $CH_2$ may be substituted with O or S, or -Sp$^5$-P in which $Sp^5$ represents a single bond or an alkylene group of 1 to 10 carbon atoms in which each of the hydrogen atoms of the alkylene group may be substituted with a fluorine atom, and P represents a polymerizable group, Ya, Yb, Yc, and Yd each independently represent a hydrogen atom or an alkyl group of 1 to 4 carbon atoms, Hb's each independently represent a perfluoroalkyl or fluoroalkyl group of 2 to 30 carbon atoms, m and n are each independently 2 or 3, and the structures in a plurality of parentheses may be the same or different, o is an integer of 0 or more, and a plurality of X when o is 2 or more may be the same or different.

10. A film with a fixed cholesteric liquid crystal phase of a liquid crystal composition, wherein the liquid crystal composition comprises a polymerizable liquid crystal molecule, and a compound represented by the following formula (I):

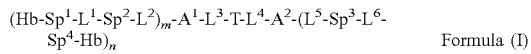

wherein $L^1$, $L^2$, $L^5$, and $L^6$ each independently represent a single bond, —O—, —S—, —CO—, —COO—, —OCO—, —COS—, —SCO—, —NRCO—, or —CONR—, $L^3$ is —COO— or —CONR—, $L^4$ is —OCO—, and T is

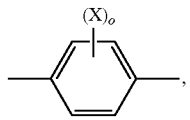

R in the formula (I) each independently represent a hydrogen atom or an alkyl group of 1 to 6 carbon atoms, $Sp^1$, $Sp^2$, $Sp^3$, and $Sp^4$ each independently represent a single bond or an alkylene group of 1 to 10 carbon atoms in which each of the hydrogen atoms of the alkylene group may be substituted with a fluorine atom, $A^1$ and $A^2$ represent a trivalent or tetravalent aromatic hydrocarbon group, wherein X represents an alkyl group of 1 to 8 carbon atoms, an alkoxy group, a halogen atom, a cyano group, or —COOR$^0$ in which $R^0$ represents a hydrogen atom, an alkyl or fluoroalkyl group in which each of the linking $CH_2$ may be substituted with O or S, or -Sp$^5$-P in which $Sp^5$ represents a single bond or an alkylene group of 1 to 10 carbon atoms in which each of the hydrogen atoms of the alkylene group may be substituted with a fluorine atom, and P represents a polymerizable group, Ya, Yb, Yc, and Yd each independently represent a hydrogen atom or an alkyl group of 1 to 4 carbon atoms, Hb's each independently represent a perfluoroalkyl or fluoroalkyl group of 2 to 30 carbon atoms, m and n are each independently 2 or 3, and the structures in a plurality of parentheses may be the same or different, o is an integer of 0 or more, and a plurality of X when o is 2 or more may be the same or different.

11. The film according to claim 9 having optical anisotropy.

12. The film according to claim 9 having a selective reflection property.

13. The film according to claim 12 having a selective reflection property in an infrared wavelength region.

\* \* \* \* \*